US010004834B2

(12) United States Patent
Hossainy et al.

(10) Patent No.: US 10,004,834 B2
(45) Date of Patent: Jun. 26, 2018

(54) BRAIDED SCAFFOLDS

(71) Applicant: Abbott Cardiovascular Systems Inc., Santa Clara, CA (US)

(72) Inventors: Syed Faiyaz Ahmed Hossainy, Hayward, CA (US); John E. Papp, Temecula, CA (US); Joel Harrington, Redwood City, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 185 days.

(21) Appl. No.: 14/484,943

(22) Filed: Sep. 12, 2014

(65) Prior Publication Data

US 2015/0081000 A1     Mar. 19, 2015

Related U.S. Application Data

(60) Provisional application No. 61/877,910, filed on Sep. 13, 2013, provisional application No. 61/945,745, filed on Feb. 27, 2014.

(51) Int. Cl.
| | |
|---|---|
| *A61F 2/06* | (2013.01) |
| *A61F 2/86* | (2013.01) |
| *A61L 31/14* | (2006.01) |
| *A61F 2/88* | (2006.01) |
| *A61F 2/90* | (2013.01) |
| *A61F 2/966* | (2013.01) |
| *A61F 2/82* | (2013.01) |
| *A61F 2/95* | (2013.01) |

(52) U.S. Cl.
CPC .............. *A61L 31/148* (2013.01); *A61F 2/88* (2013.01); *A61F 2/90* (2013.01); *A61F 2/966* (2013.01); *A61F 2002/826* (2013.01); *A61F 2002/9517* (2013.01); *A61F 2250/0018* (2013.01); *A61F 2250/0031* (2013.01); *A61F 2250/0039* (2013.01); *A61F 2250/0067* (2013.01)

(58) Field of Classification Search
CPC .. A61F 2230/0069; A61F 2/2418; A61F 2/90; A61F 2210/0004; A61F 2/06; A61F 2/07; A61F 2002/30062; A61F 2210/0014
See application file for complete search history.

(56) References Cited

U.S. PATENT DOCUMENTS

| | | | | |
|---|---|---|---|---|
| 5,718,159 | A | * | 2/1998 | Thompson ................ A61F 2/06 623/1.53 |
| 5,824,037 | A | * | 10/1998 | Fogarty ..................... A61F 2/07 623/1.13 |

(Continued)

FOREIGN PATENT DOCUMENTS

| | | |
|---|---|---|
| EP | 0 861 638 | 9/1998 |
| WO | WO 00/44308 | 8/2000 |
| WO | WO 03/057079 | 7/2003 |

OTHER PUBLICATIONS

International Search Report and Written Opinion for PCT/US2014/055363, dated Nov. 28, 2014, 13 pgs.

*Primary Examiner* — Ann Schillinger
(74) *Attorney, Agent, or Firm* — Squire Patton Boggs (US) LLP

(57) ABSTRACT

A braided polymeric scaffold, made at least in part from a bioresorbable material is deployed on a catheter that uses a push-pull mechanism to deploy the scaffold. A drug coating is disposed on the scaffold. A plurality of scaffold segments on a catheter is also disclosed.

11 Claims, 22 Drawing Sheets

(56) References Cited

U.S. PATENT DOCUMENTS

| | | | | |
|---|---|---|---|---|
| 5,980,564 A | * | 11/1999 | Stinson | A61F 2/90 |
| | | | | 606/191 |
| 6,083,257 A | * | 7/2000 | Taylor | A61F 2/90 |
| | | | | 623/1.46 |
| 8,814,927 B2 | * | 8/2014 | Shin | A61F 2/90 |
| | | | | 623/1.15 |
| 2003/0135265 A1 | * | 7/2003 | Stinson | A61F 2/90 |
| | | | | 623/1.16 |
| 2003/0153973 A1 | * | 8/2003 | Soun | A61F 2/90 |
| | | | | 623/1.16 |
| 2004/0249435 A1 | | 12/2004 | Andreas et al. | |
| 2005/0288763 A1 | | 12/2005 | Andreas et al. | |
| 2011/0264186 A1 | | 10/2011 | Berglung et al. | |

\* cited by examiner

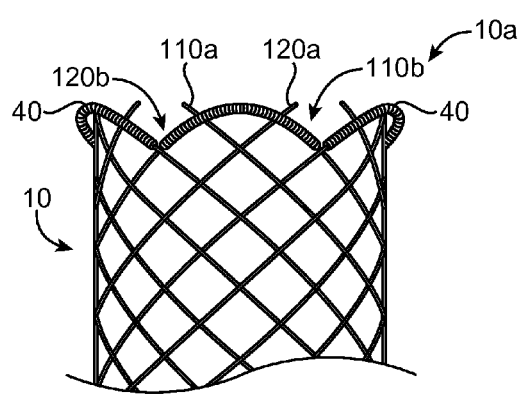 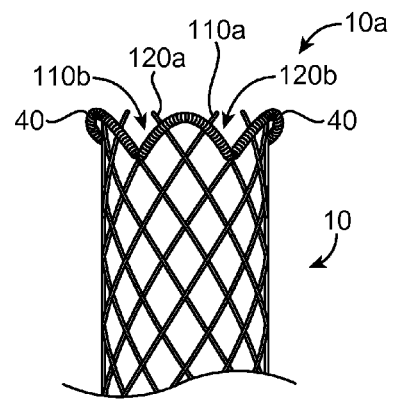
FIG. 18A  FIG. 18B
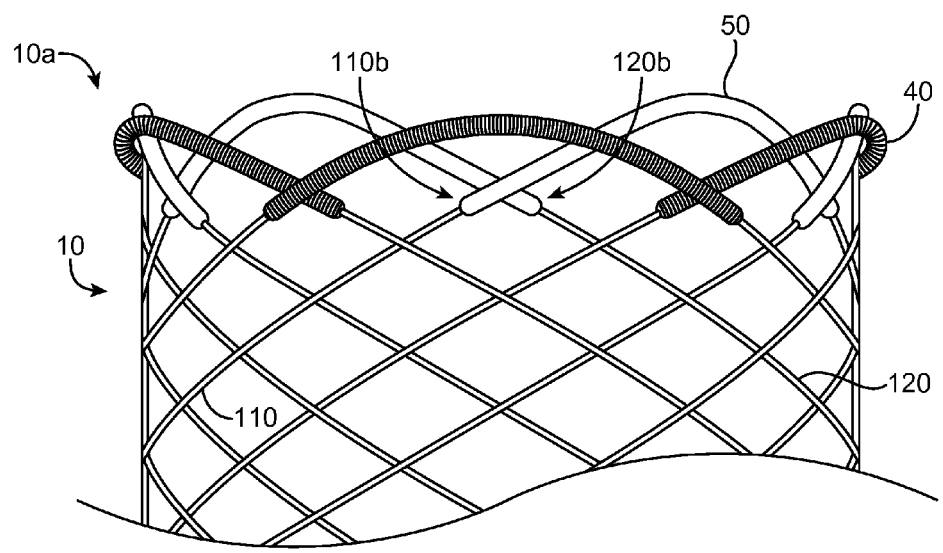
FIG. 18C

BRAIDED SCAFFOLDS

The application claims priority to U.S. Provisional application No. 61/877,910 filed Sep. 13, 2013 and U.S. Provisional application No. 61/945,745 filed Feb. 27, 2014, the entire contents of each of these provisional applications is hereby incorporated by reference for all purposes.

FIELD OF INVENTION

The present invention relates to braided or woven stents or scaffolds for treatment of peripheral vessels, such as the superficial femoral artery.

BACKGROUND OF THE INVENTION

Radially expandable endoprostheses are artificial devices adapted to be implanted or deployed in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen (one example of a stent is found in U.S. Pat. No. 6,066,167 to Lau et al). Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

A self-expanding stent is capable of expanding from a compressed or collapsed state to a radially expanded state. A delivery device which retains the stent in its compressed state is used to deliver the stent to a treatment site through vessels in the body. After the stent is positioned at the treatment site, the delivery device is actuated to release the stent which allows the stent to self-expand within the body vessel. The delivery device is then detached from the stent and removed from the patient. The stent remains in the vessel at the treatment site as an implant.

The stent must be able to satisfy a number of basic, functional requirements. The stent must be capable of withstanding the structural loads, for example, radial compressive forces, imposed on the stent as it supports the walls of a vessel after deployment. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

Radial strength, which is the ability of a stent to resist radial compressive forces, relates to a stent's radial yield strength around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation.

Even before the radial yield strength is exceeded there may be permanent deformation in the stent following a radial compressive load, but this degree of permanent deformation somewhere in the stent is not severe enough to have a significant effect on the stent's overall ability to radially support a vessel. Therefore, in some cases the art may view "radial yield strength" as the maximum radial loading, beyond which the scaffold stiffness changes dramatically. "Radial yield strength" units are sometimes force-divided-by-length, which is an expression of radial yield strength on a per-unit-length basis. Thus, for a radial yield strength per unit length, e.g., F N/mm, the radial load which, if it exceeds this value, would result in significant change in stiffness for a stent having two different lengths, L1 and L2, would therefore be the product F*L1 and F*L2, respectively. The value F, however, is the same in both cases, so that a convenient expression can be used to appreciate the radial yield strength independent of the length of the stent. Typically, the radial force that identifies the point where stiffness is lost does not change much on a per-unit-length basis when the stent length changes.

A radial "stiffness" refers to the amount net radial inward force (i.e., uniform radial inward pressure over the entire abluminal scaffold surface×the abluminal surface area) required to reversibly decrease a scaffold diameter by a certain amount. The slope of the curve from a force-deflection plot will be called the "absolute stiffness" or K. The units are N/mm and the stiffness is expressed for the linearly elastic range of response to the radial force. Thus, for a scaffold deployed to 6.5 mm and having a linear elastic range for radial compression between 6.5 mm and 5.5 mm and a radial stiffness of 20 N/mm, a net inward radial inward force of 10 N is needed to decrease the scaffold diameter from 6.5 mm to 6.0 mm. After the radial force is removed, the scaffold returns to the 6.5 mm diameter.

Alternatively, scaffold radial stiffness may be expressed as a stiffness normalized to the scaffold length, or "length-normalized stiffness" (K-Lnorm). First, the radial deflection is measured for an applied force. Next, for each recorded change in scaffold length, the corresponding applied force is divided by the length of the scaffold. This normalized force (e.g., N/mm) is then used with the displacements to compute a stiffness, rather than the actual force that produced the displacement. The resulting length-normalized stiffness has units of (N/mm per mm). The relationship between K and K-Lnorm for a scaffold with length L is $$K\text{-}Lnorm = [(F2/L - F1/L)*(D2 - D1)^{-1}]$$
$$= (1/L)*[(F2 - F1)*(D2 - D1)^{-1}]$$
$$= (1/L)*K$$

Where D2 is the measured scaffold diameter when uniform radial force F2 is applied and D1 is the measured scaffold diameter when uniform radial force F1 is applied. Hence, K is obtained by multiplying K-Lnorm by the scaffold length L.

Alternatively, scaffold radial stiffness may be normalized both with respect to the scaffold length (L) and the scaffold initial diameter (Do), or "Intrinsic stiffness" (K-norm). The relationships among the three types of radial stiffness are $$K\text{-norm}=(Do)*K\text{-Lnorm}=(Do/L)*K$$

Similar definitions are adopted for a pinching stiffness, which may be measured by a flat-plate test. Pinching stiffness is discussed in US20110190871. Thus, an absolute, length normalized and intrinsic pinching stiffness, denoted as KP, KP-Lnorm and KP-norm, respectively, for a scaffold of length L and initial height (diameter) Do are $$KP\text{-norm}=(Do)*KP\text{-Lnorm}=(Do/L)*KP$$

A polymer scaffold can be made from a biodegradable, bioabsorbable, bioresorbable, or bioerodable polymer. The terms biodegradable, bioabsorbable, bioresorbable, biosoluble, or bioerodable refer to the property of a material or stent to degrade, absorb, resorb, or erode away from an implant site. The polymer scaffold is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a polymer scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts or fibers must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed) inherent in the material, only compound this complexity in working with a polymer, particularly, bio-absorbable polymer such as PLLA or PLGA.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to provide mechanical support within the peripheral vessel for the duration needed. This is because a peripheral scaffold is placed in a significantly different environment from a coronary scaffold. The vessel size is larger. And there is much more movement of the vessel, especially when located close to an appendage. As such, a scaffold intended for a peripheral vessel will need to be able to sustain more complex loading, including a combination of axial, bending, torsional and radial loading. See e.g. Bosiers, M. and Schwartz, L., *Development of Bioresorbable Scaffolds for the Superficial Femoral Artery*, SFA: CONTEMPORARY ENDOVASCULAR MANAGEMENT ('Interventions in the SFA" section). These and related challenges facing peripherally implanted stents and scaffolds are also discussed in US2011/0190872.

There is a need to develop a prosthesis for treating peripheral blood vessels that can provide mechanical support for the vessel, until this support is no longer needed and then resorb away. There is a further need to develop such a prosthesis that minimizes late lumen loss and stenosis of the vessel, such as within the first month following implantation, thereby providing improved vascular patency.

SUMMARY OF THE INVENTION

In response to these needs disclosed herein are embodiments of braid, self-expanding scaffolds made at least partially from bioresorbable fiber material. According to the invention the concepts disclosed may be applied to a peripherally-implanted, bioresorbable scaffold. These concepts, however, are also useful for a wider variety of luminal indication such as coronary, intracranial vessels, carotid vessels, venous location such as AV fistula, IVC, airway obstruction, tracheal implant, biliary implant etc.

According to one aspect of the invention there is a scaffold or plurality of scaffold segments, method for deploying such scaffold(s) and medical device including a deployment mechanism for such scaffold(s) for supporting a non-uniform, tapered or narrowed vasculature without imposing a chronic outward force (COF) capable of causing damage to the vessel.

According to another aspect of the invention a scaffold or scaffold segment may have radial strength or stiffness that decreases with time to a selected residual value that persists for an indefinite time post-deployment. This may be advantageous in treatments where it is desirable to have a residual stiffness in the treated vessel.

According to another aspect of the invention a peripherally-implantable braided scaffold or scaffold segment may be made completely from a bioresorbable material or a hybrid where some braids are made from a bioresorbable material while other braids are made from a non-degrading material, such as Nickel Titanium (NiTi) or Nickel-Chromium. The Bioresorbable material may be poly(L-lactide) ("PLLA"), poly(L-lactide-co-glycolide) ("PLGA").

According to another aspect of the invention one or more scaffolds or scaffold segments are used to a support a vessel having a narrowed or varied lumen size over a lesion length. The scaffolds are sized for different vessel sizes and while avoiding a chronic outward force (COF) condition on the vessel, or compensating for by varying the relative radial stiffness. In view of the foregoing there are the following non-limiting examples of variations on a plurality of segmented scaffold designs for treating a vasculature having narrowed portions:

Equal deployment lengths (L), freestanding lengths (Zi) and freestanding radii (Ri) and vary the fiber length (S) for all or a portion of the plurality of segments to account for changes in the vasculature and/or avoid COF.

Equal deployment lengths (L), fiber lengths (S) and freestanding radii (Zi) and vary the freestanding length (Zi) for all or a portion of the plurality of segments to account for changes in the vasculature and/or avoid COF.

Equal deployment lengths (L) and vary S/Zi for all or a portion of the plurality of segments to account for changes in the vasculature and/or avoid COF.

For all or a portion of the plurality of segments L, S, Zi, Ri are the same or vary, and additionally different numbers of filaments, or different cross-section filaments among the segments to account for the changes in vasculature and/or avoid COF.

For all or a portion of the plurality of segments L, S, Zi, Ri are the same or vary, and additionally different filament types having increased/decreased cross-sectional area to account for the changes in vasculature and/or avoid COF.

For all or a portion of the plurality of segments L, S, Zi, Ri are the same or vary, and additionally vary the picks/inch or brad angle from proximal to distal end to account for the changes in vasculature and/or avoid COF.

According to another aspect of invention there is a hybrid braided scaffold having a radial strength or stiffness decreasing to a residual value may include non-degradable filaments and degradable filaments woven to form a tubular configuration. At deployment, the scaffold has a radial stiffness or radial strength having contributions from the non-degradable and degradable filaments. The radial stiffness or radial strength of the scaffold decreases with time due to decrease in the contribution to the radial strength or stiffness of the degradable filaments. Eventually, the contribution of the degradable filaments becomes negligible or zero and the scaffold has a residual radial strength or stiffness provided by the non-degradable filaments.

According to the invention, there is a braided scaffold, a medical device, method for making such a scaffold, a method of treatment, a method of loading a scaffold, a kit, or method for assembly of a medical device comprising such a scaffold or scaffold segments and/or catheter having one or more, or any combination of the following items (1)-(36):

(1) A peripherally-implanted medical device, comprising: a first plurality of fibers, strands or ribbons comprising a polymer a first weaving using the first plurality of fibers, strands or ribbons and being braided to each other to form a tubular body, a second weaving at a first end, and a third weaving the second end, wherein the first weaving is different from the second and third weaving. The device may or may not also include: wherein the second weaving includes a higher picks per inch than the first weaving or higher cross-over angle than the first weaving; and/or wherein the second and third weaving extend over about 5, 10, 15, 2, 4, 8 percent of the length of the scaffold when in the free-standing or compressed state.

(2) A peripherally-implanted medical device, comprising: a catheter having an axis, a distal end and a proximal end; a woven scaffold having threads made from a polymer material; the catheter distal end further comprising: the scaffold in a compressed form, a first member, comprising: a first tube received within a bore of the scaffold, a tip located at a distal end of the first tube, and a second tube proximal of the scaffold and having a stop abutting the scaffold proximal end, the first tube being received and axially movable within a lumen of the second tube, wherein the first tube is configured for being displaced towards the distal or proximal end by a first mechanism coupled to the first member and located at the proximal end, a second member comprising: a restraining sheath disposed over the scaffold, wherein the sheath is configured for being displaced towards the distal or proximal end by a second mechanism coupled to the second member and located at the proximal end; and wherein the catheter proximal end is configured for pulling the second member towards the catheter proximal end while the first member is pushed towards the catheter distal end using the respective second and first mechanisms, and wherein the first and second mechanisms are operable either separately or together to provided, in the latter case, a pre-determined % push to pull of the first and second members.

(3) The device may include any combination of the following: the catheter further comprising one or more gears coupled to, or comprising the first and second mechanisms; or the first and second mechanisms comprise at least one gear and two racks connected to the respective first and second members; wherein the first and second mechanisms each comprise one or more gears coupled to the respective first and second members; and/or wherein the catheter proximal end includes a handle comprising the first and second mechanisms, (i) wherein the first and second mechanisms are enabled to adjust a push and pull of the first member and second member respectively, wherein when the scaffold is deployed the push % is about 10%, 20%, 30%, 40%, 50%, 60%, 70%, 80%, 90%, or 20-40%, 40-80%, 30-60%, up to 50%, up to %80% or between about 30% and 70% with respect to the corresponding % pull whereby the % pull and % push sum to %100; (ii) wherein the first mechanism comprises a gear that has a diameter the same size as, greater than, or less than a gear size(s) of the second mechanism, or the gear size of the first mechanism is 0.5, 0.3, 0.7, 1.5, 2, 2.5, 1.2, 1.3, or 3 times the size of a gear for the second mechanism such that the pull can be different from the % push; (iii) the first and second mechanisms are coupled to each other and operated by a single knob, selectively coupled by a lock; (iv) the first and/or second mechanism include a clutch or construction to enable the respective first and second members to be moved from a gear having a larger and smaller diameter, or to de-couple one mechanism form the other to allow independent push or pull; (v) any combination of (i) through (iv).

(4) A peripherally-implanted medical device, comprising: a tubular body formed from a plurality of threads, the threads comprising a polymer, wherein the threads are woven together to provide radial stiffness to the tubular body, and a marker comprising a single, helically wound ribbon comprising a radiopaque material.

(5) A method for applying a composition to a braided scaffold having ends and a plurality of threads/strands/fibers braided together to form a tubular body, comprising: placing the scaffold on a mandrel, and applying the composition to the scaffold, while applying the composition, bringing the ends closer and farther apart from each other on a periodic basis during the coating.

(6) The method may include any combination of the following: a drying step comprising placing the scaffold before a forced air dryer; and/or further including moving ends closer or farther apart at a rate of about 0.5, 1, 2, 5, 10, 5-10, 3-14 or about 10-20 cycles per second as the scaffold rotates either when the composition is applied or when dried before a forced air dryer.

(7) A method for treating a calcified lesion, comprising the steps of 1) measuring the calcification; 2) adjusting a catheter's push-to-pull ratio for deployment according to a desired deployed diameter in a vessel, wherein the push-to-pull ratio is adjusted according to chart containing a correlation between push-to-pull ratio and deployed diameter for the braided scaffold, wherein the push to pull ratio adjusts the amount the scaffold is pushed distally to the amount a constraining sheath is pulled proximally, and 3) deploying the braided scaffold according to the selected push-to-pull ratio.

(8) A method for deploying a scaffold from a catheter, comprising the steps of: determining artery length and diameter at and near the lesion determining lesion hardness and diameter needed to hold the lesion open; selecting from among a plurality of deployment protocols for the scaffold based on the above information and a chart correlating a balloon pressure or radial force for maintaining lumen ID to the plurality of deployment protocols; and deploying the scaffold using the selected deployment protocol to achieve the desired deployed diameter.

(9) The method may include any combination of the following: a method of treating a calcified lesion requiring expansion of the lumen diameter to maintain patency by selectively increasing the diameter of the braided scaffold including axially constraining the scaffold using the catheter; and/or a method of increasing the radial force applied by a deployed braided scaffold by restraining the scaffold axially during deployment. Separately or in combination an apparatus for performing a medical procedure, comprising a catheter and indications enabling the practice of the method.

(10) A medical device, comprising a braided, self-expanding scaffolding formed by threads comprising a biodegradable polymer; a catheter comprising a distal end, proximal end, and a handle disposed at the proximal end; the scaffold being stowed at the distal end and contained within a retractable sheath operable from the proximal end handle; the catheter further including, a second member comprising the sheath, a first member comprising a stop, and a third member comprising a tube including a tip; wherein the handle comprises a means for pulling the sheath, pushing the stop and not moving the tip; and/or wherein the third member comprises one of a balloon or compliant surface wherein when the scaffold is being deployed material of a balloon membrane and/or compliant surface is at least partially embedded between threads of the scaffolding to provide increased axial stiffness to the scaffold ends or raise the buckling force.

(11) A kit for performing a medical procedure, comprising: (a) a catheter; (b) a braided scaffold comprising a polymer; and (c) providing indications for use. The indications for use including in any combination: i. a plurality of forces or balloon pressures corresponding to the force or balloon pressure, respectively, for maintaining a desired inner diameter of a diseased native vessel; ii. a scaffold diameter in a free-standing state, compressed state, or as-delivered state correlated to i., and/or iii. a scaffold diameter in a free-standing state, compressed state, or as-delivered state correlated to i., and iv. a % push to a pull of a member abutting the scaffold proximal end and a sheath circumscribing the scaffold, respectively correlated to i. The kit may include in any combination: wherein item (a) comprises the scaffold contained within a tube in its free-standing state, and a tool for loading the scaffold into the catheter; and/or wherein in item (c) "providing" means providing an address for accessing the indications for use over a network.

(12) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer, and wherein the scaffold comprises a middle axial section and two end axial sections and the end axial sections have a radial strength 10%, 20%, or 30% higher than the middle axial sections so that the end sections reduce or prevent migration of a scaffold in a vessel when deployed, a length of the end axial sections being 1 to 5 mm.

(13) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer, and wherein the scaffold comprises a middle axial section and two end axial sections and the end axial sections are flared radially outward in the free state so that a radial strength of the end axial sections is higher than the middle axial section in a deployed state so that the end sections reduce or prevent migration in a vessel when deployed.

(14) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer, and wherein the scaffold comprises a middle axial section and two end axial sections and the end axial sections have picks per inch 10% to 30% or 30% to 50% higher than the middle axial section so that a radial strength of the end axial section is 10% to 20%, 20% to 30%, or 30% to 40% higher than the middle axial sections which reduces or prevents migration of the scaffold in a vessel when deployed, a length of the end axial section being 1 to 5 mm.

(15) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer including poly(L-lactide), and wherein ends of the filaments at both ends of the scaffold have loops and when the scaffold is expanded, the loops at both ends of the scaffold expand to a higher diameter compared to a middle axial section of the scaffold which provides a higher radial strength at the ends than the middle axial section which reduces or prevents migration of the scaffold deployed in a vessel.

(16) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer, and wherein the filaments have a ribbon cross-section with a width and thickness with opposing flat surfaces forming an inner and outer surface of the scaffold and a ratio of width to thickness between 2.5 and 3. The scaffold may include in any combination: wherein the scaffold comprises properties selected from the group consisting of wherein a width is between 0.02 in and 0.025 in; wherein the filaments include two sets extending in an opposed helix configuration along a longitudinal dimension of the implant and the sets cross each other at a braid angle between 60 and 100 degrees; wherein a crystallinity of the filaments of the scaffold is 10% to 40%; wherein a ratio of a diameter in the free state to a diameter in the collapsed state is 2.5 to 3; wherein the scaffold is self-expandable from the collapsed state to the deployed state and a ratio of the diameter in the free state to a diameter in the deployed state is 1.3 to 1.7; wherein the diameter in the free state is 6 to 10 mm; wherein a picks per inch of the braided scaffold is 15 to 20; wherein the filaments have a tensile modulus along the fiber axis of 2.5 GPa to 8 GPa; wherein a radial strength of the scaffold when the ends are 100% restrained is 0.7 to N/mm; wherein a crush recovery of the scaffold is greater than 95% of the deployed diameter after being crushed by a pinching load 80% from the deployed diameter; wherein the bioresorbable polymer includes poly(L-lactide), and any combination thereof.

(17) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer, and wherein a ratio of the diameter in the free state to the diameter in the collapsed state is 2.5 to 3. The scaffold may include in any combination: wherein the scaffold comprises properties selected from the group consisting of: wherein the filaments have a ribbon cross-section with a width and thickness with opposing flat surfaces forming an inner and outer surface of the scaffold and a ratio of width to thickness between 2.5 and 3 and a width between 0.02 in and 0.025 in, wherein the filaments include two sets extending in an opposed helix configuration along a longitudinal dimension of the implant and the sets cross each other at a braid angle between 60 and 100 degrees, wherein a crystallinity of the filaments of the scaffold is 10% to 40%, wherein the scaffold is self-expandable from the collapsed state to the deployed state and a ratio of the diameter in the free state to a diameter in the deployed state is 1.3 to 1.7, wherein the diameter in the free state is 6 to 10 mm, wherein a picks per inch of the braided scaffold is 15 to 20, wherein the filaments have a tensile modulus along the fiber axis of 2.5 GPa to 8 GPa, wherein a radial strength of the scaffold when the ends are 100% restrained is 0.7 to N/mm, wherein a crush recovery of the scaffold is greater than 95% of the deployed diameter after being crushed by a pinching load 80% from the deployed diameter, wherein the bioresorbable polymer includes poly(L-lactide), or any polymer composition comprising poly(L-lactide) ("PLLA") or poly(L-lactide-co-glycolide) ("PLGA").

(18) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer, wherein a picks per inch of the braided scaffold is 15 to 20, and wherein a radial strength of the scaffold when the ends are 100% restrained is 0.7 to 2 N/mm. The scaffold may include in any combination wherein the scaffold comprises properties selected from the group consisting of: wherein the filaments have a ribbon cross-section with a width and thickness with opposing flat surfaces forming an inner and outer surface of the scaffold and a ratio of width to thickness between 2.5 and 3 and a width between 0.02 in and 0.025 in, wherein the filaments include two sets extending in an opposed helix configuration along a longitudinal dimension of the implant and the sets cross each other at a braid angle between 60 and 100 degrees, wherein a crystallinity of the filaments of the scaffold is 10% to 40%, wherein the ratio of a diameter in the free state to a diameter in the collapsed state is 2.5 to 3, wherein the scaffold is self-expandable from the collapsed state to the deployed state and a ratio of a diameter in the free state to a diameter in the deployed state is 1.3 to 1.7, wherein the diameter in the free state is 6 to 10 mm, wherein the filaments have a tensile modulus along the fiber axis of 2.5 GPa to 8 GPa, wherein a crush recovery of the scaffold is greater than 95% of the deployed diameter after being crushed by a pinching load 80% from the deployed diameter, wherein the bioresorbable polymer includes poly(L-lactide), and any combination thereof.

(19) A self-expanding scaffold for treating a peripheral vessel comprising: a braided scaffold comprising filaments braided to form a tubular configuration, wherein the scaffold has a free state and a collapsed state, wherein the scaffold is self-expandable from the collapsed state to a deployed state in a patient, wherein the filaments comprise a bioresorbable polymer, wherein a ratio of a diameter in the free state to a diameter in the collapsed state is 2.5 to 3, and wherein the scaffold is self-expandable from the collapsed state to the deployed state and a ratio of the diameter in the free state to a diameter in the deployed state is 1.3 to 1.7. The scaffold may include in any combination: wherein the scaffold comprises properties selected from the group consisting of wherein the filaments have a ribbon cross-section with a width and thickness with opposing flat surfaces forming an inner and outer surface of the scaffold and a ratio of width to thickness between 2.5 and 3 and a width between 0.02 in and 0.025 in; wherein the filaments include two sets extending in an opposed helix configuration along a longitudinal dimension of the implant and the sets cross each other at a braid angle between 60 and 100 degrees; wherein a crystallinity of the filaments of the scaffold is 10% to 40%; wherein the diameter in the free state is 6 to 10 mm; wherein a picks per inch of the braided scaffold is 15 to 20; wherein the filaments have a tensile modulus along the fiber axis of 2.5 GPa to 8 GPa; wherein a radial strength of the scaffold when the ends are 100% restrained is 0.7 to N/mm; wherein a crush recovery of the scaffold is greater than 95% of the deployed diameter after being crushed by a pinching load 80% from the deployed diameter; wherein the bioresorbable polymer includes poly(L-lactide), and any combination thereof.

(20) A tubular body, e.g., a coil 40 or tube 42 illustrated in FIG. 41C, that caps, connects, covers or encapsulates a pair of terminal ends of filaments forming a braided scaffold or stent is included with a braided scaffold. The ends of a first and second filament are fit within the opposing ends of the tubular body after the scaffold is made. When the ends are securely held within the ends of the tubular body there is formed a continuous segment connecting a first filament to a second filament at distal and/or proximal ends of the scaffold.

(21) Some or all open or terminal ends of filaments of a polymeric, braided scaffold are encapsulated from a polymer tubing, e.g., polycaprolactone (PCL).

(22) The scaffold is woven from filaments that are ribbons made from PLLA and the weave pattern is half diamond or full diamond.

(23) A medical device having a proximal and distal end includes an expandable anchor or cage that presents a stop or barrier when deployed. The stop or barrier is distal of a stowed scaffold. The anchor or cage prevents or inhibits an adjacent braided scaffold from displacing distally of an intended deployment site in vessel. The anchor or cage may be made from Nitinol memory-shaped wires attached to guide wire or guidewire lumen.

(24) A retrieval device, e.g., a tube, passed through deployed scaffold and pushed over a deployed cage or anchor.

(25) An anchor having 2, 3, 4 or a plurality of arms. Each arm has one end affixed to a tube or guidewire and the other end extends outward when a radial restraint is withdrawn.

(26) A scaffold comprising a unitary braided scaffold having a proximal or distal end; or a braided scaffold including at least one filament extending from a proximal to distal end of the scaffold.

(27) A scaffold comprising a plurality of scaffold segments; or a scaffold

(28) A cage forming a circular or rectangular barrier when deployed. The cage may have collar that allow each end to rotate about the supporting lumen or guide wire. One of the collars is located between proximal and distal stops to hold the cage in a fixed position to resist distal movement of the deployed scaffold.

(29) A medical device including a scaffold and anchor or cage contained within a sheath, and a pusher member.

(30) A method of deploying a scaffold including using the anchor or cage to define a distal location for the deployed scaffold.

(31) A self-expanding stent for treating a peripheral vessel comprising: a braided scaffold comprising non-degradable filaments and degradable filaments woven to form a tubular configuration, wherein the scaffold is self-expandable from a collapsed state to a deployed state, wherein upon deployment to the deployed state, the biodegradable filaments degrade and a radial strength or stiffness of the scaffold decreases with time after deployment, and wherein when the biodegradable filaments are completely degraded, the scaffold has a residual stiffness provided by the non-degradable filaments. This additional aspect of the invention has one or more, or any combination of the following items (a)-(h): (a) the non-degradable filaments are Nitinol; (a) the degradable filaments comprise a polymer selected from the group consisting of poly(L-lactide), poly(L-lactide-co-glycolide), poly(DL-lactide), and polyglycolide; (c) the bioabsorbable filaments comprise a bioabsorbable polymer; (d) a stiffness of the scaffold decreases by no greater than 60% during the first 3 months after deployment; (e) a radial strength or stiffness of the scaffold decreases by at least about 50% during the first 3 months after deployment; (f) a stiffness of the scaffold decreases to 40 to 60% of a stiffness at deployment during the first 3 months after deployment; (g) stiffness of the scaffold decreases to the residual stiffness which is less 40% to 60% of the deployed stiffness by at least 3 months after deployment; (h) the stiffness or radial strength of the scaffold varies along an axial length of the scaffold. Item (h) has one or more, or any combination of the following items (h.1)-(h.3): (h.1) the residual stiffness is axially uniform and the stiffness at deployment varies axially; (h.2) at deployment the scaffold has a higher initial stiffness at proximal and distal ends of the scaffold which decreases to the residual stiffness when the polymer filaments are completely degraded; (h.3) at deployment proximal and distal end sections of the scaffold have a lower stiffness than a middle section, wherein the stiffness at the ends decreases faster to the residual stiffness than the middle section which reduces compliance mismatch between the scaffold and the vessel at the proximal and distal end sections.

(32) A self-expanding stent for treating a peripheral vessel comprising: a segmented braided scaffold including a plurality of braided scaffold segments configured to be deployed end to end in a vessel, at least two of the braided scaffold segments are hybrid segments comprising non-degradable filaments and degradable filaments woven to form a tubular configuration, wherein upon deployment from a collapsed state to a deployed state, the degradable filaments degrade and a radial strength or stiffness of the hybrid scaffold segments decreases with time after deployment, and wherein when the biodegradable filaments are completely degraded, each hybrid segment comprises a residual stiffness provided by the non-degradable filaments. This additional aspect of the invention has one or more, or any combination of the following items (a)-(g): (a) selected hybrid segments have a higher radial strength or stiffness at deployment than other segments while having the same or different residual stiffness as the other segments; (b) a hybrid proximal end segment and a hybrid distal end segment of the scaffold have a higher radial strength or stiffness at deployment than middle segments while having the same or different residual radial strength or stiffness as the middle segments; (c) selected hybrid segments have a lower radial strength or stiffness at deployment than other segments while having the same or different residual radial strength or stiffness than the other segments; (d) a hybrid proximal end segment and a hybrid distal end segment have a lower radial strength or stiffness at deployment than middle segments while having the same or different residual stiffness than the other segments; (e) polymer filaments of selected hybrid segments have a higher degradation than other segments so that a rate a decrease to the residual stiffness is faster than other segments; (f) degradable filaments of a hybrid proximal end segment and a distal end segment have a higher degradation rate than hybrid middle segments so that a decrease in the residual stiffness is faster than in hybrid middle segments; (g) the degradable filaments comprise a polymer selected from the group consisting of poly(L-lactide), poly(L-lactide-co-glycolide), poly(DL-lactide), and polyglycolide.

(33) A medical device, comprising: a catheter; and a plurality of disconnected self-expanding scaffold segments arranged on the catheter, the plurality of segments including at least a first segment having a first ratio of fiber length to free-standing length (S/Z1), and a second segment having a second ratio of fiber length to free-standing length (S/Z2), wherein S/Z1 is less than S/Z2.

(34) Item (33) may further include one or more, or any combination of the following things a) through s):
a) wherein S/Z1 is about 4, S/Z2 is about 3 and both of Z1 and Z2 is greater than 50 mm; wherein S/Z1 is equal to about 4, a free-standing radius and deployed length for the first segment is about 6.5 mm and about 50 mm respectively, and wherein S/Z2 is equal to about 3, and a free-standing radius and deployed length for the second segment is about 5 mm and about 50 mm respectively;
b) wherein the first segment deployed radius is about equal to the second segment deployed radius and the first segment has less braids than the second segment, or the second segment has less braids than the first segment;
c) further including a deployment mechanism and sheath containing the first and second segments, wherein the deployment mechanism is pre-arranged to remove the first and second segments from the sheaths such that the first and second segments assume a pre-determined deployed length and deployed radius, and wherein the first segment deployed radius is higher than, less than, or about equal to the second segment deployed radius, and/or the first segment deployed length is higher than, less than or about equal to the second segment deployed length;
d) wherein the deployment mechanism is pre-arranged to remove the first and second segments from the sheaths such that the first segment deployed radius is about 5-10%, 15-20%, 20-30% or about 30-35% greater or less than the second segment deployed radius;
e) wherein the deployment mechanism is pre-arranged to remove the first and second segments from the sheaths such that the first segment deployed length is about 5-10%, 15-20%, 20-30% or about 30-35% greater or less than the second segment deployed length, or equal to the deployed length;
f) wherein the deployment mechanism is pre-arranged to remove the first and second segments from the sheaths such that the first segment supports a vessel at a first diameter with a substantially zero chronic outward force (COF) and the second segment supports a vessel at a second diameter with a substantially zero chronic outward force (COF) and the first diameter is greater than the second diameter;
g) wherein the deployment mechanism is pre-arranged to remove the first and second segments from the sheaths such that the first segment supports a vessel at a first diameter with at least a portion of the support being provided by a chronic outward force (COF) and the second segment supports a vessel at a second diameter with a substantially zero chronic outward force (COF) and the first diameter is greater than, less than or equal to the second diameter;
h) wherein the second segment has a total of m braids each having a cross-sectional area (A2), wherein the first segment has a total of n braids each having a cross-sectional area (A1), at least one of m is greater than n, and A2 is greater than A1, and the two scaffolds when deployed and in response to a radially compressive force exert about the same force on the vessel walls;
i) the deployment mechanism further including a distal cage;
j) the deployment mechanism further including a gearing and/or threads for deploying the first and second scaffolds to a predetermined deployment length, wherein the first and second scaffolds are deployed to different radii at the predetermined length;
k) the deployment mechanism further including a first member coupled to a sheath and a second member coupled to a pusher, the gearing and/or threads being disposed at a proximal handle portion of the catheter;
l) further including means for adjusting a push/pull ratio for selectively deploying the first and second scaffolds and comprising the deployment mechanism;
m) further including a catheter comprising means for deploying the at least first and second scaffolds to have a different or about equal deployed length and/or deployed radius;
n) wherein the first segment has a free-standing length is higher than, lower than or equal to the second segment free-standing length;
o) wherein the first segment free-standing length is about 5-10%, 15-20%, 20-30% or about 30-35% greater or less than the second segment free-standing length;
p) wherein the first segment has a free-standing radius higher than, lower than or equal to the second segment free-standing radius;
q) wherein the first segment free-standing radius is about 5-10%, 15-20%, 20-30% or about 30-35% greater or less than the second segment free-standing radius;
r) wherein the first segment has a braid length higher than, lower than or equal to the second segment free-standing radius; and/or
s) wherein the first segment braid length is about 5-10%, 15-20%, 20-30% or about 30-35% greater or less than the second segment braid length.

(35) According to an additional aspect of the invention, there is a method for making a medical device of any of the claims and comprising the steps of making one or more scaffolds or scaffold segments according to any combination of the items (1) through (34).

(36) According to an additional aspect of the invention, there is method for treating a vasculature, comprising the steps of deploying any of the scaffolds or plurality of scaffold segments according to any combination of the items (1) through (34).

BRIEF DESCRIPTION OF THE DRAWINGS

FIG. 18A-18C show embodiments of capped or encapsulated ends for a braided stent or scaffold.

INCORPORATION BY REFERENCE

Figure 1:
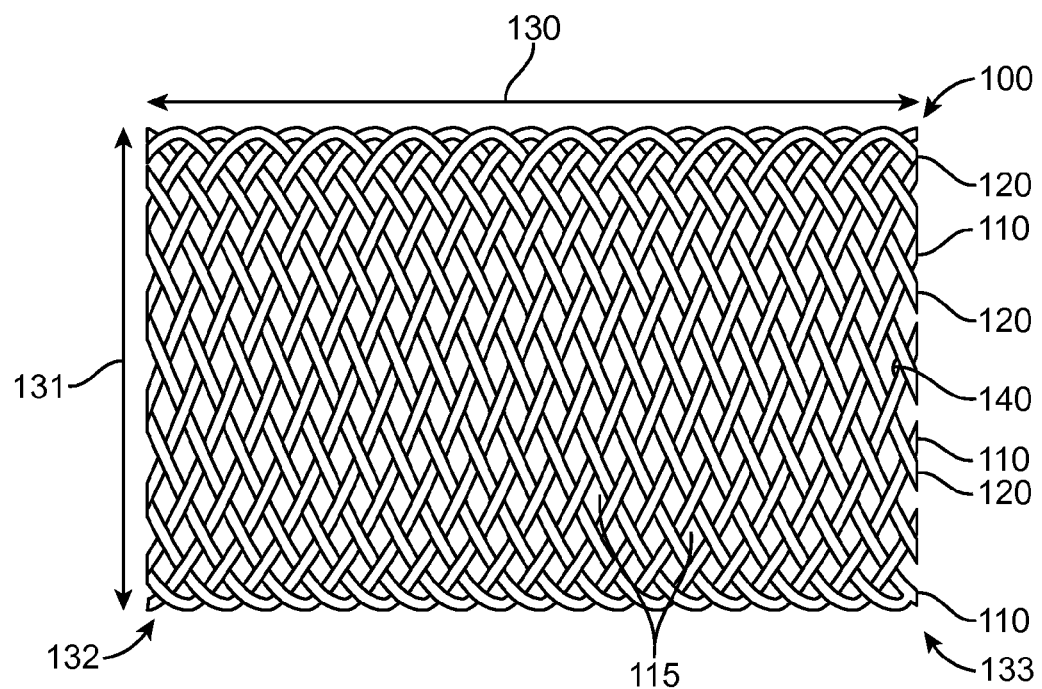
FIG. 1 depicts an exemplary braided scaffold which illustrates features of a braided or woven scaffold.

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF EMBODIMENTS

According to the disclosure there are examples applied specifically to a peripherally-implanted, bioresorbable scaffold. The concepts disclosed, however, are useful for a wider variety of luminal indication such as coronary, intracranial vessels, carotid vessels, venous location such as AV fistula, IVC, airway obstruction, tracheal implant, biliary implant etc.

For purposes of this disclosure, the following terms and definitions apply:

When reference is made to a "stent", this term may refer to a permanent structure, usually comprised of a metal or metal alloy, generally speaking, while a "scaffold" will refer to a structure comprising a bioresorbable or biodegrading polymer and capable of radially supporting a vessel for a limited period of time, e.g., 3, 6 or 12 months following deployment. It is understood, however, that the art sometimes uses the term "stent" when referring to either type of structure. A "hybrid braided scaffold" refers to a woven or braided scaffold where there are non-degradable filaments and degradable filaments woven to form a tubular configuration.

The word "weave", e.g., weaving, interwoven, as used in the disclosure, carries the same meaning and is interchangeable with forms of the word "braid."

The term "thread" means a long, thin strand of material. Threads include a ribbon, which has a rectangular cross section. A thread can also have an elliptical cross section, such as a circular cross section.

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, or between 1-2%, 1-3%, 1-5%, or 0.5%-5% different from d2. If d1 is a mean value, then d2 is about d1 means d2 is within a one-sigma, two-sigma, or three-sigma variation from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

A structure X "configured for being implanted within a living body" means X is placed within a living body in use or X is capable of being placed within the body, e.g., delivered intraluminally through the vasculature of a living body. A structure Y not suited, capable or configured for being placed within a living body means if placed within the living body in a proscribed manner would pose serious health risks to the living body. A structure Z "configured for implantation only after . . . " means Z is placed within a living body in use or X is capable of being placed within the living body and delivered intraluminally through the vasculature of a living body only after a specific step is undertaken to convert Z to X. Thus, for example, an apparatus comprising a catheter, a scaffold mounted on a balloon and a two-piece sheath on the scaffold "configured for implantation in a living body only after . . . " the two-piece sheath is pulled distally to remove it from the scaffold (Z) means (Z) is converted to X only after "the two-piece sheath is pulled distally to remove it from the scaffold." In this example, a tearing, ripping or destruction of the sheath when removing it does not convert Z to X because the sheath was not pulled distally of the catheter to remove it from the catheter. Moreover, it will be understood, referring to preferred embodiments as examples, that when a two-piece sheath according to the disclosure is positioned over a scaffold there is no way available for the sheaths to be removed using the catheter proximal end handle. As such, it will be readily appreciated the meaning of "configured for implantation in a living body only after the sheath is removed" as there is no way other than sheath removal to configure the medical device for being implanted within a body.

"Reference vessel diameter" (RVD) is the diameter of a vessel in areas adjacent to a diseased section of a vessel that appear either normal or only minimally diseased.

"Minimal lumen diameter" (MLD) is the diameter of a diseased section of a vessel at the site of maximal reduction in the diameter.

% "Diameter restenosis" (% DS) is the percent difference between the reference vessel diameter and the minimal lumen diameter: (RVD−MLD)/RVD.

"Acute gain" is defined as the difference between pre- and post-procedural minimal lumen diameter.

"Late loss" is defined as the difference between minimal luminal diameter after the procedure or post-percutaneous vessel intervention and minimal luminal diameter at follow-up.

In a balloon assisted delivery, "inflated diameter" or "expanded diameter" refers to the diameter the scaffold attains when its supporting balloon is inflated to expand the scaffold from its delivery configuration to implant the scaffold within a vessel. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

The term "polymer" may refer to a homopolymer (e.g., poly(L-lactide) or a combination of two or more types of polymers (e.g., poly(L-lactide and polycaprolactone). A combination of polymers can be a copolymer, mixture, or blend of two or more types of polymers. A copolymer can be random copolymer, alternating polymer, block copolymer, graft, or segmented polymer.

"Deployed diameter" (DD) of a scaffold refers to the maximum diameter the scaffold attains just after being released from a catheter and self-expanding from a delivery or collapsed configuration in the patient's vasculature. The DD accounts for the effects of recoil. For example, an acute DD refers to the scaffold diameter that accounts for an acute recoil in the scaffold.

"delivered", compressed or collapsed diameter or length refers to the scaffold length or diameter when being delivered to the target site via a delivery catheter.

A "fabricated diameter" means an OD of a scaffold before it is compressed or collapsed to a catheter. The fabricated diameter can also be a diameter of the scaffold in a state post-fabrication with no external forces which can be referred to as a "free" or "unloaded" state in which the scaffold has a "free" or "unloaded" diameter. Similarly, a "delivery diameter" means the OD of the scaffold when collapsed to the catheter. The "fabricated diameter" can be 2, 2.5, 3.0, 2 to 2.5, 2 to 3, 2.5 to 3 times greater than the collapsed diameter and 1.0, 1.1, 1.3, 1.4, 1.5, 1.6. 1.7, 1.3 to 1.7, and 1-1.7 times higher than a deployed diameter.

A "braided diameter" means an OD of a scaffold made from polymer threads braided or woven together to form a tubular shape.

"Recoil" means a decrease in diameter of the scaffold from a deployed diameter. Thus, when a scaffold is deployed, the scaffold may tend to return towards a smaller diameter. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

The glass transition temperature (referred to herein as "Tg") is the temperature at which the amorphous domains of a polymer change from a brittle vitreous state to a solid deformable or ductile state at atmospheric pressure. In other words, Tg corresponds to the temperature where the onset of segmental motion in the chains of the polymer occurs. Tg of a given polymer can be dependent on the heating rate and can be influenced by the thermal history of the polymer. Furthermore, the chemical structure of the polymer heavily influences the glass transition by affecting mobility of polymer chains. A lower end of Tg is Tg-LOW, a midpoint is Tg-MID and upper end is Tg-HIGH.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e radial strength.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. As noted earlier, a scaffold or stent having a desired radial force can have an unacceptable crush recovery. And a scaffold or stent having a desired crush recovery can have an unacceptable radial force. Crush recovery and crush resistance aspects of scaffolds are described in greater detail in US20110190871.

The term "crush recovery energy" given in units of N*mm refers to the energy or work required to produce the stated amount of crush (as a percentage of the diameter of the scaffold, e.g., 10% crush means the scaffold diameter or height is reduced to 90% of its pre-crush height).

Noticeable changes in a coronary scaffold's mechanical properties are mostly attributed to a critical loss in molecular weight of the polymer composition forming the load bearing scaffold structure. The change in the peripheral scaffold mechanical properties is, in contrast, a response to the loading environment in which it is implanted.

A "radial strength test" measures the radial compressive pressure required to exceed the radial strength of the scaffold. Radial strength tests were conducted on scaffolds using an MSI RX550 Radial Force Tester. Using this machine the scaffold is compressed circumferentially to a specified end diameter and compression dies within the tester record the radial force/pressure as a function of diameter. The rate of compression is 0.02 mm/sec. The scaffold is received crimped to a balloon of a balloon catheter. The scaffold is deployed on the balloon to the rated burst pressure in water at body temperature. The scaffold is compressed in air at body temperature. The radial yield strength is found from a computed modulus vs. diameter curve, which is calculated and reported as the radial stiffness. The radial strength is then reported as the maximum pressure (e.g., in millimeters of Mercury, abbreviated as "mm Hg") between the start of compression and where a 0.1 mm offset to the modulus intersects the pressure vs. diameter curve.

A "ribbon" refers to a long, narrow or thin strip of material having a rectangular or rectangular-shaped cross-section with a width greater than a thickness. Single or double ribbons may be dispensed from a bobbin during a weave process, e.g., when making a full diamond braid. Unless stated otherwise, whenever there is disclosure of a scaffold made from ribbons, the disclosure applies equally to the same scaffolds made from a filament, braid or thread, the filaments, braids or threads having an elliptical, e.g., circular or oval, cross-section.

A "free-standing" property of a braided or woven scaffold refers to a physical property of a scaffold when no external forces are being applied to the scaffold. A braided scaffold placed on a table surface, for example, assumes a free-standing radius and a free-standing length because there is no axial or radial constraint imposed on the scaffold. When a radial and/or axial constraint, pressure or force is applied or imposed, or an enforced displacement radially and/or axial imposed the scaffold no longer exhibits one or more, or none of its free-standing properties. One might alternatively refer to a free-standing state or property as heat-set or as-woven shape.

A "deployed radius" and "deployed length" for a scaffold is a radius and length, respectively, of the scaffold where one or both of the deployed radius and length are different from their respective free-standing radius and length. The term "deployed" refers to the configuration the scaffold is intended to take when implanted in a vessel. Thus, a "deployed radius" and "deployed length" may be thought of as about the radius and length of the scaffold when implanted in the intended target. Unless stated otherwise, a "deployed radius" will always refer to a radius of a scaffold that is less than a free-standing radius of the scaffold. And a "deployed length" will always refer to a length that is greater than a free-standing length.

Substantially zero chronic outward force (COF) means that when a scaffold is implanted in a vessel there is about no COF imposed on the vessel due to the scaffold being radial compressed while axial restrained. Thus, for a scaffold having a free-standing radius and length, if axial constrained and radially compressed the scaffold will impose a COF up until it is allowed to return to its free-standing radius. COF refers to a radial outward force reaction to a scaffold being radial compressed within the elastic range.

A "residual strength," "residual stiffness" or "residual strength/stiffness" means a scaffold's or scaffold segment's respective strength or stiffness that has decreased with time to a selected residual strength or stiffness that persists for an indefinite time post-deployment, i.e., that persists for a length of time equivalent to a non-degrading or all metal stent. Thus, for a scaffold having a biodegrading portion and a radial strength of 0.5 N/mm at deployment, when it has obtained its residual radial strength, e.g., three months after deployment, its radial strength will be some fraction of 0.5 N/mm, which will not change to the same extent that a radial strength of a non-degrading stent does not change after deployment.

A "zero COF deployed length and radius" means a scaffold deployed length and radius pair such that the scaffold imposes an about zero or insubstantial radial outward force on a body that confines or restrains the scaffold to the deployed length and radius.

Figure 6A:
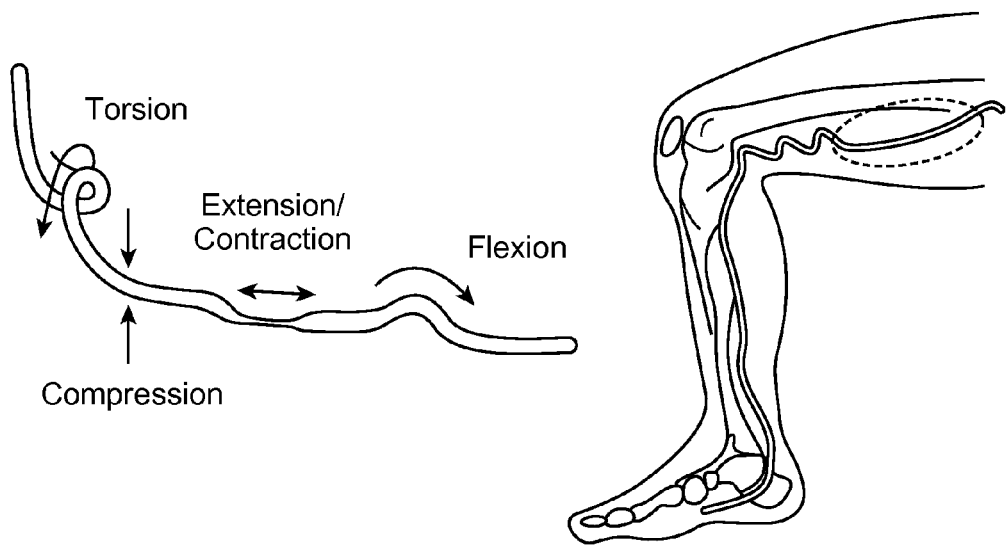
FIGS. 6A and 6B show the types of movement and/or loading of a superficial femoral artery (SFA) of the leg.
Figure 6B:
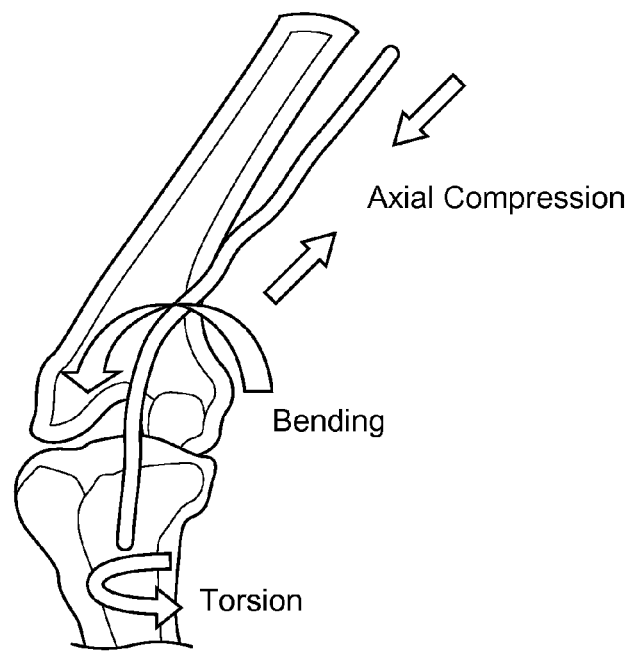

The loading on a coronary scaffold is mostly radial, reflecting the periodic contraction and expansion of blood vessels associated with blood flow through the vessels. The peripheral scaffold environment, however, is far more complex. FIGS. 6A and 6B show the types of movement and/or loading of a superficial femoral artery (SFA) of the leg. The vessel undergoes significant torsion, bending, axial contraction and extension and compression (crushing/pinching). For scaffolds implanted within this region, especially when the scaffolds are over about 40 mm in length, it is inevitable that fractures and breakdown of the scaffold begin to occur within the first month, or even within the first 1-2 weeks following implantation. In accordance with the disclosure, this process of breakdown of the scaffold's load bearing structure in a peripheral vessel, e.g., the SFA, however, can be controlled so that the supporting function of the scaffold is provided for only long enough that a neointimal layer has developed and the vessel has been restored to a state where structural support of the scaffold is no longer essential to proper vascular function. Indeed, a controlled reduction in mechanical properties (brought about by the breakdown of the scaffold structure) is believed more beneficial to restoring a more natural vascular function than, e.g., a scaffold or stent that retains its mechanical supporting properties beyond that needed to support the vessel. After the vessel has begun to repair its self, a scaffold that remains relatively radially and/or axial stiff is believed an impediment to the healing process.

According to some embodiments a peripherally-implantable braided scaffold may be made completely from a bioresorbable material or a hybrid where some braids are made from a bioresorbable material while other braids are made form a non-degrading material, such as Nickel Titanium (NiTi) or Nickel-Chromium. The Bioresorbable material may be poly(L-lactide) ("PLLA"), poly(L-lactide-co-glycolide) ("PLGA").

Accordingly, some embodiments of the present invention include a scaffold for treating peripheral vessels such as the superficial femoral artery (SFA). The scaffold includes a radially self-expandable, tubular structure formed by filaments braided or woven together. All, or at least some of the filaments are made partially or completely of a bioresorbable polymer. The scaffold is formed from filaments helically wound and interwoven into a braided configuration, which forms a tubular body capable of sustaining radial compression or providing radial support for a vessel when displaced from its free-standing state. Thus, the woven pattern provides a radial stiffness to the tubular body without there being a significant radial compression of the tubular body needed to produce the radial stiffness. In this sense the tubular body is different from self-expandable stents that provide a radial stiffness only when the body is under significant radial compression, which significant radial compression also produces a not-insignificant chronic outward force (COF) on a vessel.

Figure 2:
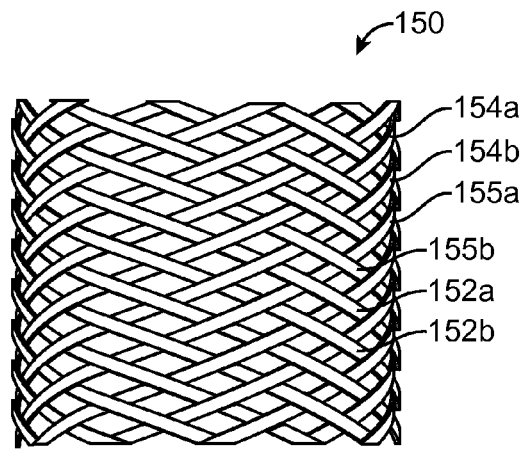
FIG. 2 depicts a herringbone pattern of braided fibers.

Referring to FIG. 1, there is depicted a portion of a braided or woven scaffold 100. Scaffold 100 includes filaments or ribbons woven together to form a tubular or substantially tubular configuration having a longitudinal dimension 130, a radial dimension 131, and first and second ends 132, 133 along the longitudinal dimension. As used herein, "woven" is used synonymously with "braided." For example, the tubular configuration may be woven to form a tubular structure including two sets of filaments 110 and 120, with each set extending in an opposed helix configuration along the longitudinal dimension of the implant. The weave pattern may be herringbone (FIG. 2), diamond full (FIG. 3A) or diamond half (FIG. 3B).

The scaffold assumes a tubular or substantially tubular form in the free-standing state. When subjected to compressive radial forces reducing its diameter, and without an axial constraint imposed the scaffold, the scaffold length will increase correspondingly and by an amount according to the type of weave and length of the filament, as now explained in greater.

For purposes of defining terms to be used in the following description reference is made to FIG. 19, which shows a single helical braid, ribbon or fiber (B). The braid has a free-standing diameter 2R (R is radius) and a corresponding free-standing length (Zi). The length (S) of B refers to the fiber length when straight. As shown, the braid B is wound into a helix of diameter 2R (note ends Ba and Bb of helix). There is a constant braid angle θ (measured with respect to horizontal axis) throughout. Also, the pics per unit length is 3/Zi (e.g., for Zi=1 inch 3 pics per inch). Referring again to FIG. 1 the same principles apply to each of the filaments shown in the scaffold. Unless stated otherwise, in the description that follows scaffolds described refer to a scaffold that has a plurality of fibers B woven together, such as shown in FIG. 1.

Figure 20:
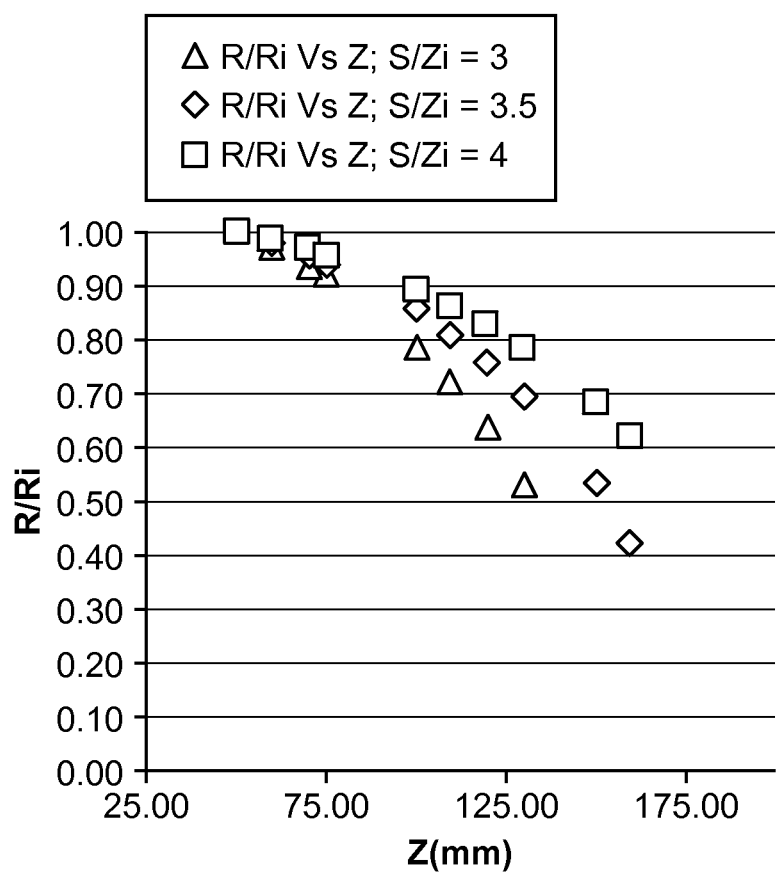
FIG. 20 is a plot showing changes in deployed length verses deployed radius for different ratios of braid length to free-standing length.

The FIG. 20 plots the radius R (normalized to a reference radius Ri) versus the increase in scaffold length. The reference radius (Ri) may correspond to the vessel radius at the scaffold distal end, midpoint or the average radius, or distal end. Or the reference radii may refer to a free-standing radius for the scaffold. For any braided scaffold according to this disclosure the radius R decreases when the length Z increases or R is inversely proportional to Z. The values for the parameter S/Zi dictate the rate of change in radius for a corresponding change in length.

Figure 19:
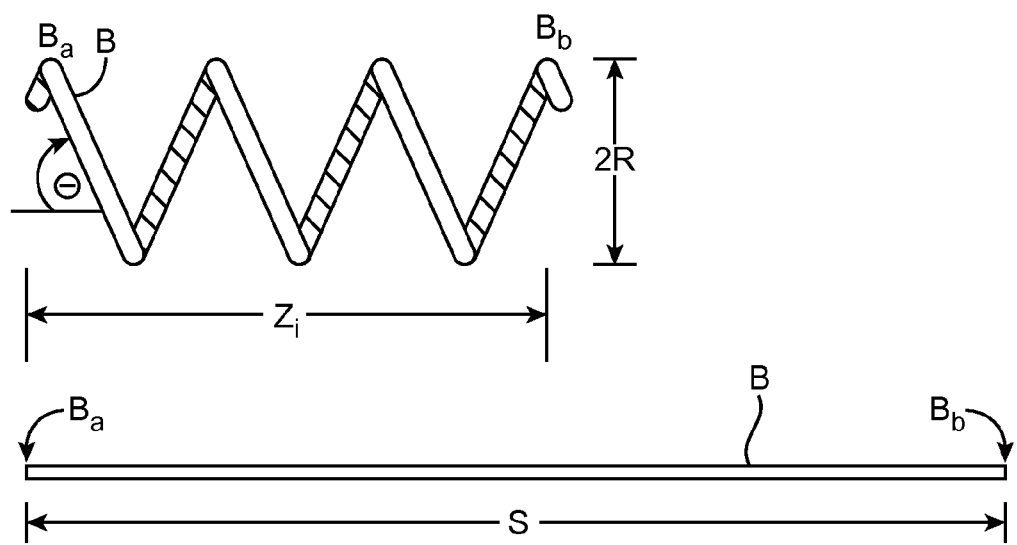
FIG. 19 illustrates aspects of a braid used for scaffolds according to the disclosed embodiments.

From FIGS. 19 and 20 it can be immediately seen the following characteristics of scaffold design according to the disclosure:

For the same free-standing length (Zi), an increase in fiber length (S) means less rapid a change in radius (R) per unit change in length (Z).

For the same fiber length (S), an increase in free-standing length (Zi) means more rapid change in radius (R) per unit change in length (Z).

The foregoing relationship is used to select scaffolds for treating vessels having narrowed or non-equal lumen spaces or openings over the treatment area. It is desirable to have implanted braided scaffolds that provide a radial support or resistance to vessel narrowing early after implantation. However, if the scaffold is not appropriately sized for the vessel, i.e., the scaffold radius (R) for a given deployment length (Z) is either too small or too large for the vessel then problems can ensure. IN the former case the scaffold can migrate in the vessel and the latter case the scaffold can impose excessive force on the vessel, i.e., a chronic outward force. What is needed is a selection of braid forming parameters that can be quickly translated into the dimensional support requirements for the scaffold. Additional relationships consistent with FIGS. 19-20 are shown in Equations 1-2:

$$Z^2 = S^2/(1+(R/Ri)^2(S^2/Zi^2-1)) \qquad \text{EQ.1}$$

EQ. 1 provides a relationship between Z and R/Ri for a given S/Zi from FIG. 20.

$$Zi^2 = S^2/(1 + 4\pi Ri^2/Zo^2) \quad \text{EQ. 2A}$$

From EQ. 2A we can solve for the picks/length:

$$1/Zo = (1/2\pi Ri) \ast (S^2/Zi^2 - 1)^{1/2} \quad \text{EQ. 2B}$$

EQS. 2A-2B therefore provides a relationship between S/Zi (FIG. 20) and the number of picks/length (1/Zo). From these relationships one can solve for the free-standing length (Zi), reference radius (Ri) and fiber length (S) to achieve a desired implant length (Z) and radius (R).

Figure 21:
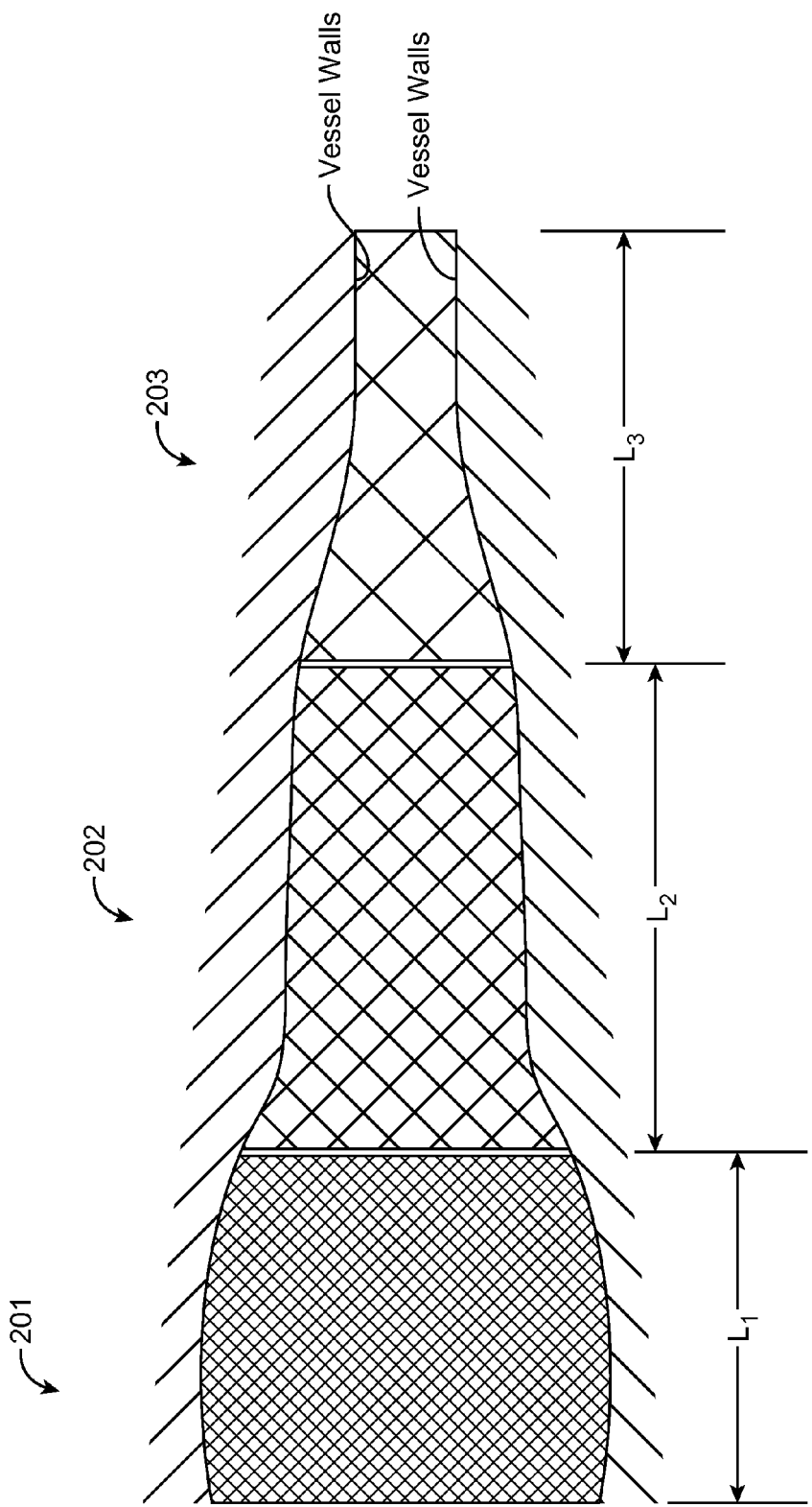
FIG. 21 depicts a narrowing vessel being supported by three scaffold segments.

FIG. 21 shows a cross-sectional view of three braided scaffold segments 201, 202 and 203 that are implanted in a narrowing vessel (note: the deployed radii are different for each scaffold). The reference or free-standing radius (Ri) for scaffolds 201, 202 and 203 is R1, R2 and R3, respectively.

The three scaffolds are placed on a catheter and delivered to the vessel and implanted as shown in FIG. 21. In this example, the three segments 201, 202 and 203 may represent three different designs each utilizing different values for S, Zi and/or Ri to achieve the desired wall coverage and radial force supporting the vessel while avoiding excessive chronic outward force (COF). The scaffolds 201, 202 and 203 may overlap each other at their ends or the ends may sit adjacent each other as shown. The scaffolds may be made from bioresorbable fibers or a combination of bioresorbable and non-degrading fibers in accordance with the other aspects of this disclosure described infra. In accordance with the objectives of avoiding excessive COF one can design the segments 201, 202, and 203 by choosing desired parameters, e.g., Z and R, or S and Ri, and then solving for the other parameters using EQS. 2, 3A, 3B arranged in the suitable algebraic form. Examples based on FIG. 21 follow.

As shown, FIG. 21 has the average vessel radius (V1, V2, V3) for scaffolds 201, 202 and 203, respectively, being such that V1>V2>V3. One wishes to support each vessel with producing a chronic outward force problem.

EXAMPLE 1

To achieve an appropriate fit for this type of vasculature, one may have the free-standing radii for scaffolds 201, 202 and 203 the same (i.e., R1=R2=R3) and equal to or greater than V3, V2, and V1, and the coverage lengths (Z) for the three scaffolds the same (i.e., L1=L2=L3, respectively, FIG. 21). With these dimensions selected, one can then, utilizing the above relationships, choose a suitable scaffold segment type for each vessel portion to avoid a chronic outward force condition for the narrowed parts of the vasculature.

One can adjust the fiber length (S) or the free-standing length (Zi) (or both) to achieve the same radial force acting on the vessel for the scaffolds 201, 202 and 203 compressed to different diameters. Thus, for Zi constant and V1>V2>V3 the fiber lengths are S1>S2>S3. Or, alternatively, for S constant and V1>V2>V3 the free-standing lengths are Z1<Z2<Z3.

EXAMPLE 2 for equal coverage lengths (Z1=Z2=Z3), increasing braid length (S1>S2>S3), and decreasing free-standing radius (R1>R2>R3) EQS. 2, 3A-3B yield the following:

Scaffold 201 values: S/Zi=4, Ri=6.5 mm, Zi=50 mm for L1,

Scaffold 202 values: S/Zi=3.5, Ri=6.0 mm, Zi=50 mm for L2,

Scaffold 203 values: S/Zi=3, Ri=5. mm, Zi=50 mm for L3.

EXAMPLE 3

For unequal coverage lengths (Z) for the three scaffolds (i.e., L1< >L2< >L3, respectively, FIG. 21) vary (S/Zi) to achieve the same radial force acting on the vessel for each scaffold having a different coverage length and deployed in vessel having variable radius.

EXAMPLE 4

Scaffold 201 deployed to only about 85% of its free-standing radius, the scaffold 202 radius deployed to only about 80% of its free-standing radius, and the scaffold 203 radius deployed to only about 70% of its free-standing radius to accommodate the respective vessel sizes in FIG. 21, and the desired deployed length of 100 mm (z=100) is the same for each of these scaffold, then FIG. 20 shows that S/Z1=4 for scaffold 201

S/Z2=3.5 for scaffold 202 and

S/Z3=3 for scaffold 203

As noted above, the ratios can be achieved by varying one or both of the fiber length S or free-standing length Zi.

In other embodiments all or a portion of a plurality of scaffold segments have the same or similar values for Ri, S, and Zi, or different values (as above) but there are a different number or types of fibers for the segments. These embodiments may be desired for one or several scaffolds where the deployed lengths and radii are such that the COF is not a substantially zero COF deployed length and radius. For example, for identical Ri, S, and Zi two scaffolds deployed in differently sized vessels, e.g., scaffold 201 and 203, can be formed to impose a similar radial force on the vessel by increasing the number of fibers in scaffold 201 or decreasing the number of fibers for scaffold 203. Or the fiber cross-sectional area (referred to as Ap-polymer, or Am-metal, below) for scaffold 201 is higher than scaffold 203. In either case by modifying the fibers in this way the segments can be deployed in a narrowed vasculature without creating a chronic outward force problem. For example, for vessel sizes that change by about 10%, 20%, 30% or 10-30% the number of fibers added to scaffold 201 deployed in the larger vessel space can be increased by about 5%, 15%, 20%, 30% or between about 10-30% or the number of fibers correspondingly decreased in scaffold 203 by these same amounts. By "similar radial force" is meant to say that the reaction force on the vessel at or near the deployment diameter is about the same. Thus, the sum of the force caused by COF at the deployed diameter plus the additional force when the vessel compresses the scaffold to less than the deployed diameter (first scaffold) is about the same as the force on the vessel when compressed at the deployed diameter for the other scaffold, which has substantially no COF at its deployed diameter. The two scaffolds may have the same or different deployment diameters.

In other embodiments all or a portion of a plurality of scaffold segments have the same or similar values for Ri, S, and Zi, or different values (as above) but a segment is a weave made with a variable braid angle or picks/inch, or is formed with tapered filaments to account for changes in the vasculature. For example a fiber is tapered so that a distal end of the scaffold has less radial stiffness than a proximal end thereof, i.e., the filament tapers to a smaller cross-sectional area from the proximal to distal end. For example, for a scaffold placed within a vessel that narrows from a proximal to distal end by 10% a fiber may be tapered to have an end cross-sectional area that is about 10-50% less than the cross-sectional area at the proximal end thereof. Or the picks/inch can be 20-30% higher (or the braid angle about 10-30%) higher at the distal end than the proximal end where the ends may each constitute about 5-10% of the entire length of the scaffold segment. A higher picks/inch or braid angle means more radial stiffness for that portion of the scaffold.

As the foregoing demonstrates, one can size scaffold segments for different vessel sizes and while avoiding a chronic outward force (COF) condition on the vessel. In view of the foregoing there are the following non-limiting examples of variations on a plurality of segmented scaffold designs for treating a vasculature having narrowed portions (e.g., FIG. 21):

Equal deployment lengths (L), freestanding lengths (Zi) and freestanding radii (Ri) and vary the fiber length (S) for all or a portion of the plurality of segments to account for changes in the vasculature and/or avoid COF.

Equal deployment lengths (L), fiber lengths (S) and freestanding radii (Zi) and vary the freestanding length (Zi) for all or a portion of the plurality of segments to account for changes in the vasculature and/or avoid COF.

Equal deployment lengths (L) and vary S/Zi for all or a portion of the plurality of segments to account for changes in the vasculature and/or avoid COF.

For all or a portion of the plurality of segments L, S, Zi, Ri are the same or vary, and additionally different numbers of filaments, or different cross-section filaments among the segments to account for the changes in vasculature and/or avoid COF.

For all or a portion of the plurality of segments L, S, Zi, Ri are the same or vary, and additionally different filament types having increased/decreased cross-sectional area to account for the changes in vasculature and/or avoid COF.

For all or a portion of the plurality of segments L, S, Zi, Ri are the same or vary, and additionally vary the picks/inch or braid angle from proximal to distal end to account for the changes in vasculature and/or avoid COF.

According to the embodiments a freestanding diameter may be between 6 to 15 mm, or more narrowly, 8 mm, 6.5 mm, 6 to 12 mm, 6 to 10 mm, 8 to 12 mm, or 8 to 10 mm. A free-standing length may be between 30 and 150 mm, or more narrowly, 30 to 100 mm, 30 to 70 mm, 30 to 50 mm, 40 to 100, 40 to 70 mm, 100 to 150 mm, 100 to 120 mm, or 50 to 80 mm.

A biodegradable braided scaffold or scaffold segment may degrade away to a point that it provides no or negligible radial stiffness or radial strength. The scaffold at deployment has a stiffness or radial strength which then decreases with time due to degradation of the filaments. The radial stiffness or radial strength continues to decrease and become negligible and then zero when the filaments degrade away.

In further embodiments, a scaffold may have radial strength or stiffness that decreases with time to a selected residual value that persists for an indefinite time post-deployment. This may be advantageous in treatments where it is desirable to have a residual stiffness in the treated vessel. For example, residual stiffness may be required or beneficial in the treatment of calcific lesions or eccentric lesions in peripheral vessel disease (PVD), highly musculo-fibrous lesions in dialysis access vessels, and fibromuscular dysplasia found in nearly every arterial bed in the body, the most common arteries affected are the renal and carotid arteries.

The residual radial strength or stiffness may be 5% to 50% of the deployed radial strength or stiffness, or more narrowly, 5 to 10%, 10 to 20%, 20 to 30%, 30 to 40%, or 40 to 50%. In some embodiments such as scaffolds for the SFA a desirable radial strength at the time of implantation is between about 0.4 N/mm and 0.75 N/mm (force-normalized by the scaffold length). For these embodiments the residual radial strength may be between about 0.02 to 0.04, 0.06 to 0.11, 0.04 to 0.08, 0.08 to 0.15, 0.12 to 0.23, 0.16 to 0.30, or about 0.20 to 0.38 N/mm.

A hybrid braided scaffold having a radial strength or stiffness decreasing to a residual value may include non-degradable filaments and degradable filaments woven to form a tubular configuration. At deployment, the scaffold has a radial stiffness or radial strength having contributions from the non-degradable and degradable filaments. The radial stiffness or radial strength of the scaffold decreases with time due to decrease in the contribution to the radial strength or stiffness of the degradable filaments. Eventually, the contribution of the degradable filaments becomes negligible or zero and the scaffold has a residual radial strength or stiffness provided by the non-degradable filaments.

Figure 22:
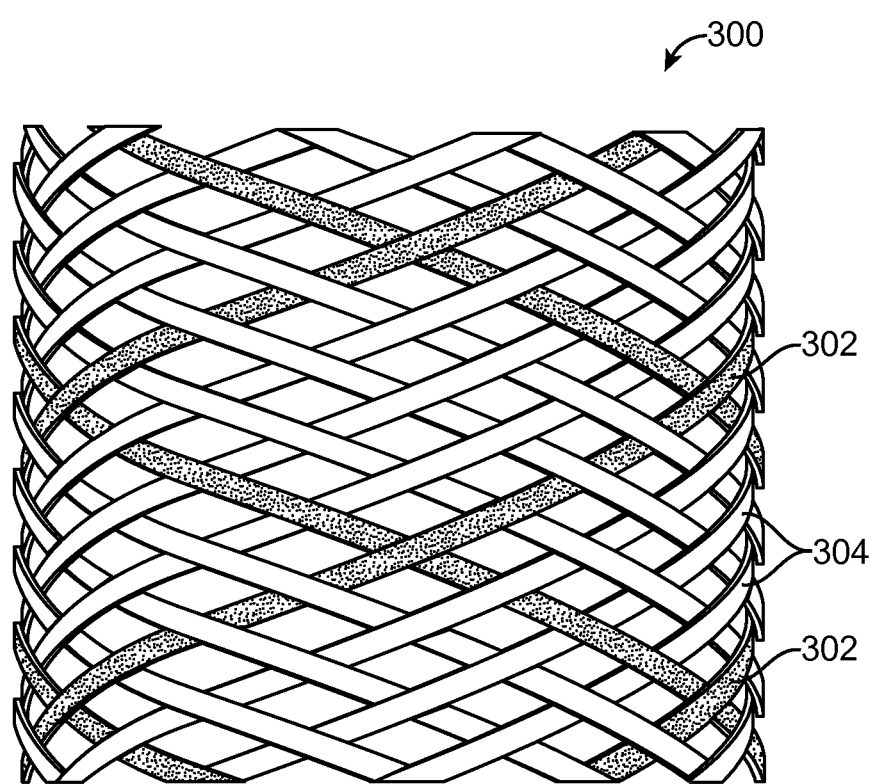
FIG. 22 shows a portion of a hybrid scaffold having a portion of the braids made from a biodegrading material and another portion made of a non-degrading material.

FIG. 22 depicts a section of an exemplary hybrid scaffold 300 including non-degradable filaments 302 and degradable filaments 304. Non-degradable filaments 302 are interwoven with degradable filaments 304.

A hybrid braided scaffold may include a plurality of non-bioerodible metal filaments braided or interwoven with a plurality of biodegradable polymer filaments. The metal filaments may be made of a metal having mechanical properties that are unchanged or stable during a time frame of treatment and beyond, for example, a lifetime of a treated patient. For example, the metal filaments can be Nitinol. The degradable polymer filaments may be made of a bulk eroding polymer or a surface eroding polymer. Polymer filaments made of polymer having bulk-eroding behavior may result in a radial strength of stiffness that is relatively constant for a period of time post-deployment, followed by a period of decrease to the residual value. Polymer filaments made of a polymers having surface eroding behavior may result in a radial strength or stiffness that starts to decrease shortly after deployment and continues to decrease to the residual value.

Exemplary bulk-eroding polymers include PLLA, poly (DL-lactide), poly(L-lactide-co-glycolide) (PLGA), or polyglycolide. With respect to PLGA, the polymer may have a mole % of GA between 1-99 mol %, or more narrowly, 5 mol % (95/5 PLGA), 15 mol % (85/15 PLGA), 25 mol % (75/25 PLGA), 35 mol % (65/35 PLGA), 50 mol % (50/50 PLGA), 75 mol % (25/75 PLGA), or 95% (5/95 PLGA). Exemplary surface-eroding polymer include polyanhydrides or polyorthoesters.

The sooner the scaffold loses stiffness, the vessel motion in all modes, pulsatile radial motion, axial motion, bending motion etc. achieves values for the native vessel. This will result in less stress on the vessel at earlier time points. However, this time point of a particular reduced stiffness, such as the time to reach the residual stiffness or a particular percentage decrease in stiffness, should be selected such that patency created by the scaffold is sustained after stiffness is reduced. Thus, the return to vessel behavior to the native state is balanced with requirement of sustained patency.

The hybrid scaffold may be designed or configured such that the radial stiffness or radial strength may decrease by a selected amount in the desired degradation time frame. In some embodiments, the biodegradable filaments degrade and a radial strength or stiffness of the scaffold decreases by at least 30%, 40%, 50%, or 60% at or by at least 3, 4, 5, or 6 months after deployment. The biodegradable filaments may degrade and a radial strength or stiffness of the scaffold decreases by 30 to 40%, 40 to 50%, or 50% to 60% at or by the end of the first 3, 4, 5, or 6 months after deployment.

In other embodiments, the biodegradable filaments degrade and a radial strength or stiffness of the scaffold decreases to the scaffold's residual strength or stiffness that is, or is less than 20%, 30%, 40%, 50%, 60% of the scaffold's deployed radial strength or stiffness at, or by at least 3, 4, 5, or 6 months after deployment. In other embodiments, the biodegradable filaments degrade and a strength or stiffness of the scaffold decreases to the scaffold's residual strength or stiffness that is 20 to 30%, 30 to 40%, 40 to 50%, 50 to 60% of the deployed scaffold's strength or stiffness at, or by at least about 3, 4, 5, or 6 months after deployment.

The degradation profiles described above may be achieved through selection of a material with lower (faster degrading) or higher (slower degrading) degradation time. For instance, PGA or 50/50 PLGA provides a fast degrading filament. The degradation profiles may also be achieved alternatively or additionally by adjusting the cross-sectional surface area of the filaments. For instance, decreasing the area decreases the degradation time.

The initial radial strength or stiffness, the residual radial strength or stiffness, and the decay profile of the radial strength or stiffness can be adjusted by hybrid braided scaffold parameters. The parameters of the hybrid scaffold may include scaffold geometry, filament geometry, and filament material properties. The scaffold geometry parameters include the density of the filaments, number of metal filaments (Nm), and number of degradable polymer filaments (Np). The filament geometry parameters include cross-sectional area of metal filaments (Am), cross-sectional area of degradable polymer filaments (Ap), and the lengths Zp and Zm of the respective metal and polymer filaments that are woven to make the hybrid scaffold.

The material properties of the polymer filaments include the tensile modulus of the polymer (Ep) and degradation rate. The radial strength and stiffness at deployment can be adjusted through selection of a polymer with higher or lower Ep. The amount of decrease in radial strength or stiffness over a particular time frame can be adjusted through selection of a polymer with a higher or lower degradation rate.

As an illustration, the properties of various polymers from the literature shown in Table 4 can be used to estimate the relative scaffold properties made from different polymers. The value of mechanical properties of a polymer filament will differ from the values in Table 4 since mechanical properties also depend on the processing of the filament. Also, the radial strength and stiffness are scaffold properties and depend on both scaffold geometry and material properties of filaments. The highest and fastest decaying radial strength or stiffness may be obtained with PGA filaments. As compared to PGA, PLLA filaments may provide a scaffold that has a lower and slower decaying radial strength or stiffness. PDLLA filaments may provide a scaffold with slightly less radial strength or stiffness than PLLA, however, the radial strength and stiffness may decays at a rate between PLLA and PGA. PLGA filaments with L-lactide content from 50 to 85 mol % may provide a scaffold with about the same stiffness as PDLLA, however, the degradation rate increases between 85 mol % and 50 mol % L-lactide content which may result in progressively faster decaying radial strength or stiffness.

TABLE 4

Properties of biodegradable polymers.

| Polymer | Modulus (Gpa) | Tensile Strength (MPa) | Degradation Time (months)[a] |
|---|---|---|---|
| PGA | 7.0[1]; 5-7[2] | 60-80[2] | 6-12[1,2] |
| PLLA | 2.7[1]; 3[2] | 60-70[2] | >24[1]; >36[2] |
| PDLLA | 1.9[1]; 2[2] | 2[2] | 12-16[1]; 12-15[2] |
| 85/15 PLGA | 2.0[1] | N/A | 5-6[1] |
| 75/25 PLGA | 2.0[1] | N/A | 4-5[1] |
| 65/35 PLGA | 2.0[1] | N/A | 3-4[1] |
| 50/50 PLGA | 2.0[1] | N/A | 1-2[1] |

[1]Medical Plastics and Biomaterials Magazine, March 1998.
[2]Medical Device Manufacturing & Technology 2005.
[3]The Biomedical Engineering Handbook, Joseph D. Bronzino, Ed. CRC Press in Cooperation with IEEE Press, Boca Raton, FL, 1995.
[4]Science, Vol. 297 p. 803 (2002)
[a]Degradation time also depends on part geometry.

A hybrid scaffold having a selected radial strength or stiffness at deployment and a selected radial strength and stiffness after selected degradation time can be designed by adjusting various scaffold parameters and measuring the radial strength or stiffness at deployment and various degradation times. The parameters of the polymer filaments may be adjusted independently of the metal filaments for a selected radial strength or stiffness at a selected degradation time. A hybrid braided scaffold may have an Np/Nm of 2 to 10, or more narrowly, 2, 4, 6, 10, 2 to 4, 4 to 6, or 6 to 10. The Ap/Am may be 1, 1 to 1.5, 1.5 to 2, or 2 to 4. The Np/Nm, Ap/Am, or both may be varied to provide the temporal radial strength or radial stiffness profiles described herein.

The hybrid scaffold may also be characterized by the relative mass of the metal filaments and polymer filaments or metal: polymer ratio, mass of metal filaments/polymer filaments. Exemplary ranges of the metal: polymer ratio are 1/2 to 1/10 or 1/4 to 1/20. The first range may applicable, for example, to Nitinol/PLLA and the second to Nitinol/PLGA, since from Table 4, PLLA is stiffer than PLGA copolymers.

The temporal profile of radial strength or stiffness can be varied additionally through adjustment of Ap. Decreasing the Ap increases the rate of decay to the residual radial strength or stiffness. Thus a scaffold or a portion of scaffold segments may degrade more rapidly than another scaffold portion of scaffold segment by using different Ap sizes for braids or by using a tapered braid for a scaffold portion of some of the segments.

The radial strength or stiffness of the hybrid scaffold can vary along the axial length of the scaffold through variation of the density of the filaments. The axial variation of the metal filaments and polymer filaments can be different by having different axial variation in metal and polymer filament density. Axial variation in radial strength or stiffness may be useful for lesions that have axial asymmetry.

There are various alternatives for the varying the radial strength or stiffness axially. The residual stiffness may be axially uniform due to uniform metal filament density; however, the stiffness at deployment may vary axially due to variation in the polymer filament density. One particular embodiment may include a higher initial radial strength or stiffness at the proximal and distal ends which decays to a residual radial strength or stiffness with time. The radial strength or stiffness of the ends (or end segments, e.g., segments 201 and 203 verses segment 202 from FIG. 21) may be 5 to 10% greater, 10 to 15% greater, 15 to 20% greater, or 20 to 30% greater. Proximal and/or distal end sections of a scaffold may be 10 to 30% of the total length of a scaffold or 5 to 10 mm, 10 to 15 mm, or 15 to 20 mm.

Another particular embodiment is a lower initial radial strength or stiffness at the proximal and distal ends which decays to a residual radial strength or stiffness with time. In another embodiment, the initial radial strength and stiffness at the ends may be the same as or different from the middle, but may decay faster to the residual radial strength or stiffness due to a lower density of polymer filaments at the ends which reduces compliance mismatch between the scaffold and the vessel at the ends throughout the degradation period. The radial strength or stiffness of the ends may be 5 to 10% greater, 10 to 15% greater, 15 to 20% greater, or 20 to 30% greater. In these and other embodiments, proximal and/or distal end sections of a scaffold (or end segments, e.g., segments 201 and 203 verses segment 202 from FIG. 21) may be 10 to 30% of the total length of a scaffold or 5 to 10 mm, 10 to 15 mm, or 15 to 20 mm.

In another alternative, the residual radial strength or stiffness is varied axially by varying the density of the metal filaments. For example, the scaffold may have a lower or higher radial strength or stiffness at the ends. The stiffness due to the polymer filaments may be uniform axially or nonuniform axially.

Further aspects include a segmented braided scaffold including a plurality of braided scaffold segments configured to be deployed end to end in a vessel. At least two of the braided scaffold segments are hybrid segments having non-degradable filaments and degradable filaments woven to form a tubular configuration. In some aspects, all of the segments are hybrid segments. The scaffold segments are self-expandable from a collapsed state to a deployed state and may be arranged end to end in the collapsed state for deployment in a vessel to the deployed state. In the collapsed state, the segments may be constrained over a catheter.

Upon deployment to the deployed state, the biodegradable filaments degrade and a radial strength or stiffness of the hybrid scaffold segments decreases with time after deployment. When the biodegradable filaments are completely degraded, a hybrid segment has a residual stiffness provided by the non-degradable filaments. The length of the scaffold segments may be 10 to 15 mm, 15 to 20 mm, 20 to 30 mm, or 30 to 40 mm, or 40 to 50 mm. The distance between the ends of adjacent scaffolds in the collapsed or deployed state may be 1 to 2 mm, 2 to 3 mm, 3 to 5 mm, or 5 to 10 mm. In some embodiments ends of the scaffold segments may overlap each other.

The hybrid segments may have the same or different stiffness at deployment and the same or different residual radial strength or stiffness. The residual radial strength or stiffness may be the same and the initial radial strength stiffness may be different. The rate of decrease to the residual stiffness may also be different by using different polymers, different filament density, or both.

As discussed in connection with FIGS. 19-21, the radial strength or stiffness along a deployed segmented scaffold may be varied by deploying segments with different radial strength and stiffness. In one aspect, selected hybrid segments have a higher stiffness at deployment than other segments while having the same or different residual radial strength or stiffness as the other segments. For example, a hybrid proximal end segment and a hybrid distal end segment have a higher initial stiffness than middle segments while having the same or different residual stiffness as the middle segments. The selected hybrid segments may have a radial strength or stiffness 5 to 10% greater, 10 to 15% greater, 15 to 20% greater, or 20 to 30% greater than the other segments, such as end segments stiffness compared to middle segments.

In another aspect, selected hybrid segments have a lower radial strength or stiffness at deployment than other segments while having the same or different residual radial strength or stiffness than the other segments. For example, a hybrid proximal end segment and a hybrid distal end segment have a lower radial strength or stiffness at deployment than middle segments while having the same or different residual radial strength or stiffness than the middle segments. The selected hybrid segments may have a radial strength or stiffness 5 to 10% less, 10 to 15% less, 15 to 20% less, or 20 to 30% less than the other segments, such as end segments stiffness compared to middle segments.

In another aspect, polymer filaments of selected hybrid segments have a higher degradation rate resulting in a faster decrease to the residual radial strength or stiffness that is faster than other segments. For example, polymer filaments of a hybrid proximal end segment and a distal end segment have a higher degradation rate than hybrid middle segments so that a decrease in the residual radial strength or stiffness is faster than in hybrid middle segments. The selected hybrid segments, for example, may have a selected decrease in radial strength or stiffness or reach the residual strength or stiffness 10 to 20% sooner, 20 to 30% sooner, 30 to 40% sooner, or 40 to 50% sooner than the other segments.

In another aspect, the rate of decay of radial strength or stiffness to the residual radial strength or stiffness can be controlled by the cross-sectional area of the polymer filaments. For example, the radial strength or stiffness of the proximal and/or distal end segments can decay faster or slower than the middle segments by having a lower or higher, respectively, filament cross-sectional area. For example, filament cross-sectional area (Ap) of the proximal and/or distal end segments can be 30 to 60% lower or 30 to 60% higher than the middle segments.

Scaffold Fibers According to Some Embodiments

The fibers of the scaffold may be made partially or completely of a bioresorbable polymer, such as aliphatic polyester. The fibers may have various cross-sections such as circular or square. The fiber cross-section may also be asymmetric, such as rectangular, oval, or more generally, a flat cross-section.

The fibers with asymmetric cross-sections may be woven so that the smaller dimension (thickness) is parallel with the radial direction and the larger dimension (width) is parallel with the circumferential direction. In a scaffold woven with flat filaments, the larger dimension surfaces forms an outer and inner surface of the scaffold.

A flat fiber/filament provides lower scaffold thickness, and lower overall crimp profiles leading to better product performance, including more flexibility and less material for the body to absorb. Less material to absorb in the body is believed to cause less inflammatory response than a scaffold made of thicker/larger mass of material. For example, the thickness of a scaffold with a solid round fiber of 0.007" OD can range from 0.007"-0.014" depending on the design of the scaffold. When a flat fiber/filament is used instead of round filament, for the same or similar surface coverage, the thickness of the filament can be made smaller than the width as the OD of round fiber. In addition, a scaffold made from flat fiber/filament has more surface contact between the fiber and the vessel leading to a more stable net providing support to a vessel wall. If the same amount material is used for both round and flat fiber/filament, more vessel area will be covered. The greater coverage additionally provides for better drug distribution for a drug-eluting scaffold.

The ratio of the width to the thickness of a flat fiber may be 1.1, 1.2, 1.5, 1.8, 2, 2.5, 3, 3.5, 4, or any range between any combination of a small and larger of these ratio values. The width may be 0.002 in, 0.005 in, 0.01 in, 0.012 in, 0.015, 0.017 in, 0.02 in, 0.022 in, 0.025 in, or any range between any combination a smaller and larger of these width values.

The filaments may be made in whole or in part of a bioresorbable amorphous polymer (e.g., <5% crystallinity) or a bioresorbable semicrystalline polymer. A semicrystalline polymer can include amorphous regions and crystalline regions with the degree of crystallinity ranging, for example, from 10 to 80%. The degree of crystallinity can be modified by processing of the polymer, for example, by annealing the polymer between the Tg and Tm of the polymer or by deforming the polymer at a temperature between Tg and Tm of the polymer. The degree of crystallinity of the polymer of the filaments can be 10 to 80%, 10 to 60%, 10 to 50%, 10 to 40%, 10 to 30%, 10 to 20%, 20 to 60%, 20 to 50%, 20 to 40%, or 20 to 30%.

The fibers may be made in whole or in part of polymer with a Tg above body temperature making them stiff and strong at body temperature which is approximately 37 deg C. Bioresorbable polymers include poly(L-lactide), poly(glycolide) (PGA), polycaprolactone (PCL), poly(trimethylene carbonate) (PTMC), polydioxanone (PDO), poly(4-hydroxy butyrate) (P4HB), poly(butylene succinate) (PBS), poly(D-lactide), poly(DL-lactide), and any combination thereof in any proportion. The bioresorbable polymer can be a combination of a polymer with a Tg greater human body temperature (e.g., 95-99 wt %) and a polymer with a Tg below human body temperature (e.g., 1 to 5 wt % or mol %). An exemplary combination is PLLA and PCL.

The filaments may have tensile modulus along the fiber axis of 2.5 GPa to 8 GPa, or more narrowly, 5 GPa to 8 GPa.

Weave Patterns

Scaffold filaments are woven together using methods into various weave patterns. Exemplary weave patterns include a full diamond (FDI), half diamond (HDI) and herringbone (HB) patterns. FIG. 2 depicts a portion of a scaffold having an HB braid formed from ribbons, including ribbons 152a, 152b, 154a, 154b, 155a, and 155b. Ribbons 152a and 152b are wound in an opposite direction from ribbons 154a, 154b, 155a, and 155b. The pattern 150 may be described as follows. Each ribbon, e.g., 152a, 152b, passes over two ribbons, then under two ribbons, etc. Thus, no ribbon passes over only one ribbon, then under only one adjacent ribbon, etc. Additionally, no adjacent ribbons pass over or under the same two ribbons. For example, ribbon 152a passes over the two ribbons 155a, 155b while adjacent ribbon 152b passes over 155a and under 155b. Ribbon 152b passes over both ribbons 155a and 154b while adjacent ribbon 152a passes under ribbon 154b.

Figure 3A:
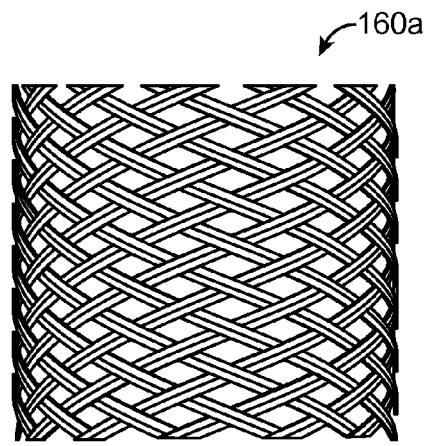
FIGS. 3A and 3B depict a diamond full and diamond half pattern of braided fibers.
Figure 3B:
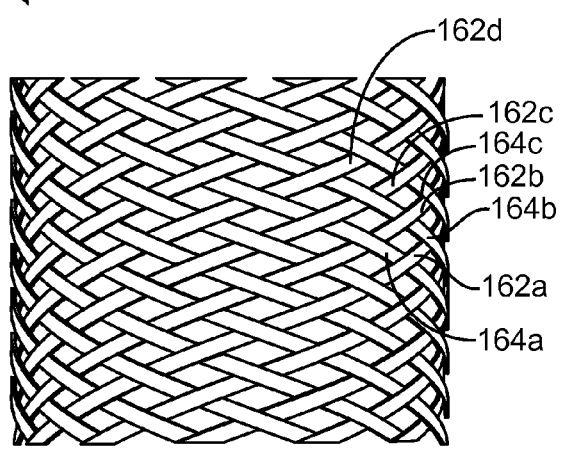

FIGS. 3A and 3B depict a FDI pattern 160a and a HDI 160b, respectively. The difference is whether a single or double ribbon is used to make the braid. A FDI pattern uses two ribbons adhered together, such as by using a solvent or adhesive. The ribbons are dispensed together as a single ribbon from a bobbin during the weave. The FDI and HDI patterns are the same. Every ribbon (whether a double or single ribbon) passes over then under crossing ribbons. Additionally, no adjacent ribbons pass over (or under) the same ribbon. And in contrast to the HB pattern, no ribbon passes over (nor under) two consecutive ribbons. Thus, for patterns 160a, 160b there are ribbons 162a, 162b, 162c and 162d that cross in one direction and ribbons 164a and 164b that cross oppositely from ribbons 162a, 162b, 162c and 162d. Ribbon 164a passes under ribbon 162a, over ribbon 162b, under ribbon 162c and over ribbon 162d. Ribbon 164b passes over ribbon 162a, under ribbon 162b, over ribbon 162c and under ribbon 162d.

The HB pattern is generally stiffer in torsion and has been used for making longitudinal flexible and torsionally stiff catheter shafts. It is presently preferred to use the HDI and/or FDI type braids. It is also preferred to use a flat ribbon (as shown) over a round wire because the flat ribbon provides better vessel coverage.

The density of the braided scaffold may be quantified by the braid pick count and the number of wraps. The braid pick count of a pattern is the number of crossovers of alternate endings in a given length of braid counting parallel to the longitudinal direction of the braid, for example, expressed in picks per inch (ppi). Cells per inch (cpi) is the same as the ppi. The pattern of a scaffold may have 10 to 80 ppi, or more narrowly, 15 to 60 ppi, 15 to 40 ppi, 15 to 25 ppi, or 16 to 20 ppi. The number of wraps is the number of crossing points around the circumference of the scaffold.

Drugs

Scaffolds according to some embodiments may be used not only for mechanical intervention but also as a vehicle for providing biological therapy. Biological therapy uses medicated scaffold to locally administer a therapeutic substance, active agent, or drug, terms that will be considered as synonymous. The therapeutic substance can also mitigate an adverse biological response to the presence of the scaffold. A medicated scaffold may be fabricated by coating the surface of the scaffold with a neat active agent or a polymeric carrier that includes an active agent. The polymeric scaffold may also serve as a carrier of an active agent which may be embedded within or dispersed within the polymer of the scaffold. The term scaffold may refer to the polymer scaffold without the drug coating or the polymer scaffold with a drug coating. The polymeric carrier may be any of the polymers disclosed herein or any combination thereof.

The drug may include an antiproliferative agent, anti-inflammatory agent, or a combination thereof. The polymeric carrier of the coating may be bioresorbable and can include any of the polymer disclosed herein. Exemplary active agents include everolimus, dexamethasone, zotarolimus, and rapamycin and any of its analogs.

Manufacturing

The steps for manufacturing a braided scaffold generally include fabricating filaments, braiding filaments into a scaffold pattern over a mandrel, optionally flaring ends of the braided scaffold, heat stabilizing the braided scaffold, fitting radiopaque markers on the braided scaffold, collapsing and loading scaffold on a catheter, and sterilization of loaded scaffold.

Steps for manufacturing a fiber or filament for a braided scaffold may include the following. Polymer filaments or fibers may be formed by a process involving several steps starting with a polymer resin. In extrusion, a polymer resin is fed to an extruder barrel, melting, and the polymer melt is conveyed through the extruder barrel to an exit port. The polymer resin is fed to an extruder barrel near its proximal end in solid form, for example, as a pellet from a hopper. The polymer in the extruder barrel is heated to temperatures near or above the melting temperature (Tm) of the polymer. The polymer melt exits the distal end of the extruder barrel into a die. The die has a cross-section that imparts a fiber geometry to the polymer melt exiting the die. A continuous fiber is made by pulling or drawing the fiber exiting the die, for example, at a rate of one to four feet per minute. The draw ratio may be from 2 to 30. The drawing rate may be set to produce necking in the fiber, so as to produce a tapered fiber type disclosed in the embodiments.

The continuous fiber may then cooled, for example, by passing the fiber through a bath of water. The fiber may be cooled to a temperature between room temperature (e.g., 20 to 30 deg C. or any temperature there between) and the Tg of the polymer. The fiber may also be cooled to room temperature or to below room temperature. The cooling process may result in the nucleation and growth of crystals in the polymer of the fiber.

The high temperature and high shear stress applied to the polymer tends to decrease its molecular weight. The pre-extrusion number average molecular weight (Mn) may be 150 KD to 350 KD and the post-extrusion Mn can be 100 to 200 KD.

Representative examples of extruders include single screw extruders, intermeshing co-rotating and counter-rotating twin-screw extruders, and other multiple screw masticating extruders. Exemplary processing can be performed with a ¼" or a ¾" single screw extruder.

Any desired cross-sectional shape and dimension of the fiber may be formed through selection of the die dimensions and shape, for example, a round or ribbon cross-section. A round fiber may have an extruded diameter of 0.018 to 0.025 in. A flat fiber/filament or ribbon can be produced by extrusion process by designing or using a die similar to a film or tap process.

In some embodiments, a round fiber can be fabricated from extrusion and then is subjected to a flattening process to produce a ribbon at some point between extrusion and braiding. The flattening process can be performed at a temperature between room temperature and Tg of the polymer or between Tg and Tm of the polymer. In one embodiment, a flat fiber/filament can be produced by a compression roller over a round fiber stream after it exits the die before it is solidified.

In some embodiments, the fibers can be made from extrusion that includes drug impregnated or dispersed within the polymer. In these embodiments, the drug and polymer can be fed into the extruder. The drug can be fed into the extruder in pelletized form, for example, 3 to 4 mm pellets. The drug is mixed with the polymer in the extruder which results in a fiber with drug mixed through the polymer.

In other embodiments, a drug impregnated fiber can be formed from a solution or gel extrusion process in which a polymer solution or gel mixed with the drug is extruded to form a fiber. The polymer is dissolved in a solvent to form the gel or solution. The solutions or gel extrusion process is particularly advantageous for drug that are sensitive to degradation at temperatures of polymer melt extrusion. Extrusion of the solution or gel allows an extrusion temperature much lower than extruding a polymer melt since the solution or gel has a lower viscosity than the melt. For example, the solution or gel extrusion temperature can be between room temperature and a Tg of the polymer. Some or all of the solvent is removed from the extruded fiber upon exiting the die. Residual solvent can be removed from the fiber by heating the fiber, for example during an annealing or hot draw process.

Following formation of a fiber by extrusion, the fiber may be annealed to modify the crystallinity of the polymer. The fiber may be heated to a temperature between Tg and Tm of the polymer for 5 min to 1 hr, 1 hr to 5 hr, 5 hr to 20 hr. The increase in crystallinity increases the tensile strength and modulus of the fiber. The fibers may be under tension during the annealing process to prevent shortening of the fibers. The crystallinity may be increased by the annealing from less than 10% or 20% to 20% to a higher crystallinity within any of the ranges disclosed herein.

Fibers formed from extrusion may be subjected to a hot drawing process for selectively increasing the tensile modulus and strength of the fibers along the fiber axis. Drawing involves applying tension along the fiber axis which increases the length and decreases the cross-sectional area. The hot draw process may be performed in addition to the drawing performed as part of the extrusion process after fiber exits the die. Drawing tends to pull the molecular chains together and orient them along the fiber axis, creating a considerably stronger and rigid fiber along the fiber axis. The fiber may be at temperature between Tg and Tm of the polymer during the hot drawing process. The draw ratio which is the ratio of the final fiber length to the original fiber length prior to drawing may be 2 to 10, or more narrowly, 4 to 8. The hot drawing may also increase the crystallinity of the fiber from a post annealing crystallinity or less than 10% or 20% to 20% to any of the ranges disclosed herein. The annealing may be performed before, after, or simultaneous to the drawing process. Since the hot drawing process decreases the cross-section of the fiber, an extruded cross-sectional size must be larger a final desired post-drawing size.

Flat fibers may be formed from round fibers by several methods. In one method, the fiber is flattened during the annealing process into the desired fiber thickness and width. The flattening of the fiber may be performed at a softening temperature that is below the melting temperature under tension during the drawing step.

In another embodiment, the fiber flattening step is done prior to annealing during the extrusion fiber drawing process. The flattening step can be accomplished with a heated block.

In a further embodiment, the flattening of the fiber is done after the hot drawing process. In this case, the polymer is first extruded to a desired OD. The polymer then undergoes a hot drawing process with a draw ratio ranging from 2 to 30. At this stage, the fiber is round. The round fiber is then transferred to a flattening machine with heat applied to the fiber with a temperature between Tg and Tm of the polymer. The flattening step is done by a roller pressed over the round fiber. The flat fiber/filament may then be annealed.

The finished fibers can be collected on a spool or bobbin and stored in a freezer (e.g., less than 20 deg C.) until the braiding process.

Fibers constructed for embodiments of the disclosed scaffolds may be braided into the desired scaffold patterns with commercially available braiding machines, for example, Steeger K 80/16 braiding equipment obtained from Steeger USA of Spartanburg, S.C. The fibers can be braided on a mandrel having an outer diameter (OD) that provides a scaffold with a desired inside diameter (ID). The mandrel may be made of a plastic such as PTFE. The characteristics of the pattern may be selected on the machine such as the type of pattern (e.g., diamond or HB), ppi, and braid angle.

Encapsulated Ends

In some embodiments it may be desirable to cap, cover or encapsulate the terminal ends of filaments that form a braided scaffold. Braided scaffolds/stents made from weaved metal, metal alloy or polymeric filaments will have at least two ends where the filament was cut or severed from the remainder of the spool. The ends represent a beginning and end of the filament. Cut ends, especially when forming a relatively sharp edge, can lead to poor clinical outcomes due to constant tissue irritation or tissue trauma. Moreover, the ends can potentially cause problems with respect to the delivery system. The ends may scratch the delivery system resulting in corrosion and/or introduction of foreign particles into the blood stream.

FIGS. 18A-18B are views taken of the scaffold 10 near its distal end 10a. The scaffold body is formed by woven filaments 110, 120 that cross each other at a braid angle, as discussed earlier in connection with FIG. 1. Shown are uncovered terminal ends 110a, 120a of the filaments and ends 110b, 120b, respectively, which are covered or encapsulated by a coil 40 connecting an end 120b to an end 110b. The coil 40 may be radiopaque. The coil 40 joins the ends 110b, 120b to thereby prevent the ends 120b, 110b from interacting with either a delivery device or tissue (FIGS. 18A-18B show ends 110a, 120a not capped or encapsulated by a coil 40 only for the sake of illustration. In a preferred embodiment all ends 110a, 120a are covered or connected by a coil 40 encapsulating ends of filaments 110, 120).

The coil 40 may be welded, glued or swaged to the ends 110b, 120b to prevent detachment. Or, when the inner diameter of the coil is close to the outer diameter of the wire, the wire can be press-fit into the coil and friction relied upon to hold the coil on the end of the wire. The coil 40 can be made of any suitable material to enhance Radiopacity. Examples of such materials are Platinum, Gold, Silver, Tungsten, Tantalum or combination of such material with other alloys to allow a shape memory effect.

FIG. 18C illustrates a hybrid concept of end termination/encapsulation. A polymeric tube 42, which may be radiopaque as well (e.g., by having small radiopaque particles blended into a shape-memory polymer) are inserted onto the terminal ends 110b, 120b of the filaments 110, 120 respectively. The tube 42 may then be reduced in diameter by heating (if heat shrink properties are present) or glued to secure in place. This method would be suitable for polymeric scaffolds, while a radiopaque coil may be used for a stent formed by metallic filaments. If there is a need to boost the radial outward force of a polymeric scaffold at its ends to prevent prolapse, then a radiopaque and/or bioresorbable/biodegradable metal coil may be used as well.

In one embodiment all ends of a polymeric, braided scaffold are encapsulated in tubing made from polycaprolactone (PCL). The scaffold is woven from flat ribbons made from PLLA and the weave pattern is half diamond or full diamond.

In general, the body, e.g., coil 40 or tube 42, used to cap, connect cover or encapsulate a pair of ends is tubular having a shape memory property. The ends of the first and second filaments 120a, 110a are fit within the opposing ends of tube after the scaffold is made. When the ends are securely held within the ends of the tubular body there is formed a continuous segment connecting the ends 110a to 120a.

Migration Reduction

Scaffolds according to some embodiments have modified ends to reduce migration when implanted within a vessel. A scaffold tends to change shape in response to applied forces such as inward radial forces that can cause a decrease in the diameter and a pinching or crushing force that can cause crushing or pinching of the scaffold. The decrease in diameter or crush is accompanied by an increase in length in the absence of external forces that reduce of prevent the length increase. When the scaffold is implanted, the radial inward forces and crushing forces imposed by the vessel may cause axial sliding of the scaffold due to the change in length. The sliding can be reduced or prevented by a higher radial force between the scaffold and the vessel wall by features which selectively modify properties of the scaffold at its ends. In such embodiments, a scaffold may have variable radial strength along the its length with both ends of the scaffold having a higher radial strength than the middle axial section of the scaffold between the ends to reduce or prevent scaffold migration.

In some embodiments, the diameter at the ends of the scaffold in the free standing state can be higher than a middle axial section of the scaffold. In such embodiments, the ends of the scaffold can be flared. When the scaffold is expanded, the flared ends have a higher radial force on the vessel wall which reduces or prevents migration. A scaffold with flared ends can be by cutting a section of braid on a mandrel (e.g., PTFE) and heat set or heat stabilize at a temperature between Tg and Tm of 5 to 10 minutes or 10 minutes. Tapered sleeves (e.g., high density polyethylene) with a tapered portion are placed over the Teflon mandrel on either end of the braid and worked into the braid so that the ends of the braid are flared. An annealed wire or elastic film can be used to hold the braid tightly against the tapered sleeves.

In other embodiments, the scaffold may be designed to have higher radial strength at the ends, however, the diameter of the scaffold may not vary with length in the free state. In one embodiment, a braided scaffold may have higher picks per inch at the ends of the scaffold to increase the radial strength at the ends. The ends will also have a higher braid angle. The fibers may be wound onto the bobbin/spools and the scaffold may be braided using a braiding machine. The pitch or picks per inch for the working length of the scaffold may be predetermined by using the appropriate gear dimension in the braiding machine to produce certain of picks per inch. Once the working length of the scaffold has been braided, the gear may be changed to accommodate fabrication of the higher picks per inch for the ends of the scaffold. The length of the ends of the scaffold having the higher picks per inch may be 1 to 5 mm, or more narrowly, 1 to 3 mm. The OD of the mandrel used in the braiding process may be constant throughout the process. At the end of the braiding process, the scaffold may be heat stabilized. FIG. 6B depicts a scaffold having a constant picks per inch along its working length and ends having greater picks per inch. In some embodiments, the picks per inch at the ends may be 5% to 10%, 10% to 20%, or 20 to 30% higher than the middle axial section. The ends referred to may cover in sum total (i.e., both ends combined) be about 1%, 2%, 5%, 10%, 15%, 20%, 30% of the total scaffold length when free-standing of when at its delivered diameter within the catheter sheath.

Another embodiment is a scaffold having loops in fibers at both ends to reduce or prevent scaffold migration. When expanded, the loops at both ends of the scaffold will expand to a higher OD compared to the middle axial section of the scaffold. The ends have a higher radial strength than the middle axial section and serve as anchors resulting in the reduction or prevention of scaffold migration.

Loops in a scaffold can be formed after annealing or heat stabilization. The scaffold may be cut to a predetermined length and the ends of fibers at the scaffold ends may be formed into a loop. The loops may be welded using thermal forming processes such as laser bonding.

Heat Stabilizing

The braided scaffold may then be heat stabilized by annealing to relax or reduce residual stresses in the fibers. Such stress may be a result of the braiding process. The scaffold-mandrel-sleeve assembly may be heated, for example, by placing in an oven and heat setting at a temperature between Tg and Tm of the polymer for 5 to 10 minutes or 10 minutes. The ends of the braid are trimmed to length. The diameter of the scaffold does not change during stabilization.

Fit with RO Markers

Figure 4:
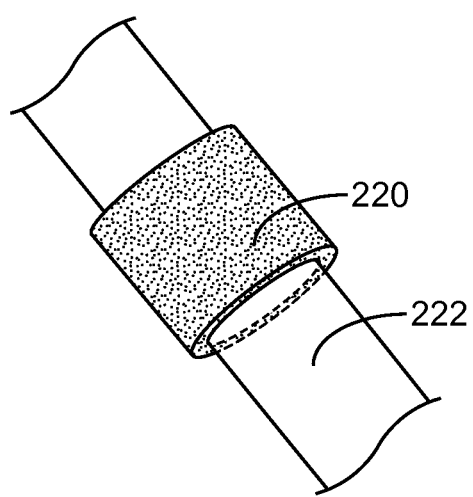
FIG. 4 depicts a marker ribbon wrapped around a fiber of a braided scaffold.
Figure 5:
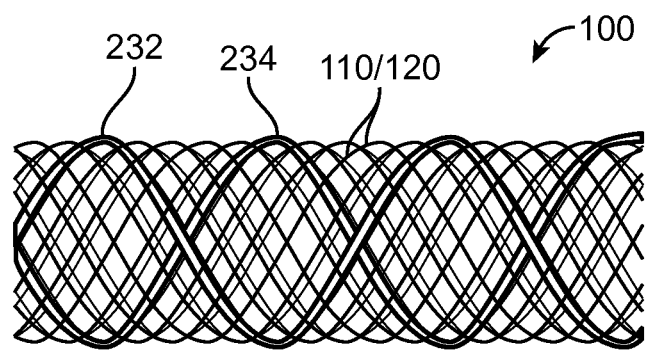
FIG. 5 depicts a braided scaffold with marker ribbons wrapped helically around the scaffold.

Disc-shaped markers made of a material having a high degree of radiopacity such as tungsten, gold, or platinum/iridium ribbon may be folded around fibers so that the scaffold position can be monitored when inside a patient using x-ray visualization techniques. FIG. 4 depicts a marker ribbon 220 wrapped around a fiber 222 of a scaffold. Two markers are placed on each end of the scaffold and are 1 mm from the end of the fiber. In another embodiment, a marker ribbon may be helically wound around the scaffold as shown in FIG. 5. Marker ribbons 232 and 234 are helically wound around the scaffold. The ribbon may have dimensions of 0.003 in×0.0025 in. Friction holds the marker in place and a drug coating can provide adhesion of the ribbon to the fibers of the scaffold. FIG. 5 depicts the scaffold 100 formed from fibers 110/120 showing marker ribbons 232,234.

Drug Coating

A polymer and drug coating may be formed over a scaffold using methods such as spraying or dipping. A coating material including a polymer dissolved in a solvent and drug may be applied to the scaffold using known techniques. For example, the coating material may be sprayed on the scaffold in multiple passes with an intervening drying step between passes to remove solvent from the applied coating material. In the drying step, the solvent may be removed through evaporation at room temperature or by heating the scaffold.

The ratio of drug to polymer may be 1:1, 1:3, 1:5, 1:1 to 1:10, or 1:1 to 1:5 by weight. The ratio of drug or polymer to solvent by weight in the coating material may be 1:35 to 1:60.

As an example, a drug (everolimus, zotarolimus) and polymer (PDLLA) at a given ratio (D:P=1:1, 1:3, 1:5, and up to 1:10) are mixed into a solvent (e.g., acetone) in which the polymer is dissolved and the drug is dissolved or dispersed. For example, a ratio of 1:1:48 by weight is applied to the scaffold. Alternatively a solvent mixture (acetone/hexanone) is used at a desired concentration (2% solid).

One challenge in coating braided scaffolds is that the deposited polymer coating may glue fibers together and as a result prevent the fibers from moving which limits the scaffold flexibility in different directions. Moreover the coating may crack when it is crimped onto the delivery system. Also, once implanted the fiber structures are constantly moving and pieces of drug coating may shed from the scaffold, which could result in thromboembolic hazards.

A coating method disclosed herein is designed for fiber-based scaffold designs to result in a coating that is conformal and does not prevent the fibers from easily moving against each other. Therefore, the coated drug-eluting scaffold retains the mechanical advantages of the braided and woven scaffold designs. The coating method includes compressing the scaffold in the axial direction after each spray pass and prior to the drying step. It is preferred to build up the final coating slowly by using a relatively large number of passes (15-30) rather than a few (<5).

The drug release mechanism of a drug-coated scaffold can either be diffusion or percolation controlled or polymer degradation controlled (slower degradable polymer for slow release or faster degradable for faster release). If a diffusion controlled system is used, the release will be controlled by the drug/polymer miscibility, the polymer glass transition temperature, and the drug to polymer ratio. The drug to polymer ratio will also control the release rate in percolation and degradation controlled systems.

A coating process may include applying the composition by spraying the composition on the scaffold as it rotates on a supporting mandrel. In one embodiment the scaffold is supported between a first member and a second member. The second member is configured for moving toward and away from the first member while the scaffold rotates and the composition sprayed on the scaffold. This relative axial motion between the first and second members, which varies the scaffold between axial compressed state and free standing state by periodic squeezing by or compression between members via contact with member walls and the scaffold ends, is intended to cause movement between overlapping threads of the scaffold. And this movement between overlapping threads causes changes to the surface areas of threads covered by other threads during the spraying process. In other words, changing the axial length of the scaffold during spraying causes threads to slide over each other and expose different parts to the sprayed composition. By continuously or periodically changing the covered surface areas of threads in this manner, more consistent coverage of composition over the threads is achieved, less coating defects and/or less adherence between threads caused by the dried composition.

Figure 12:
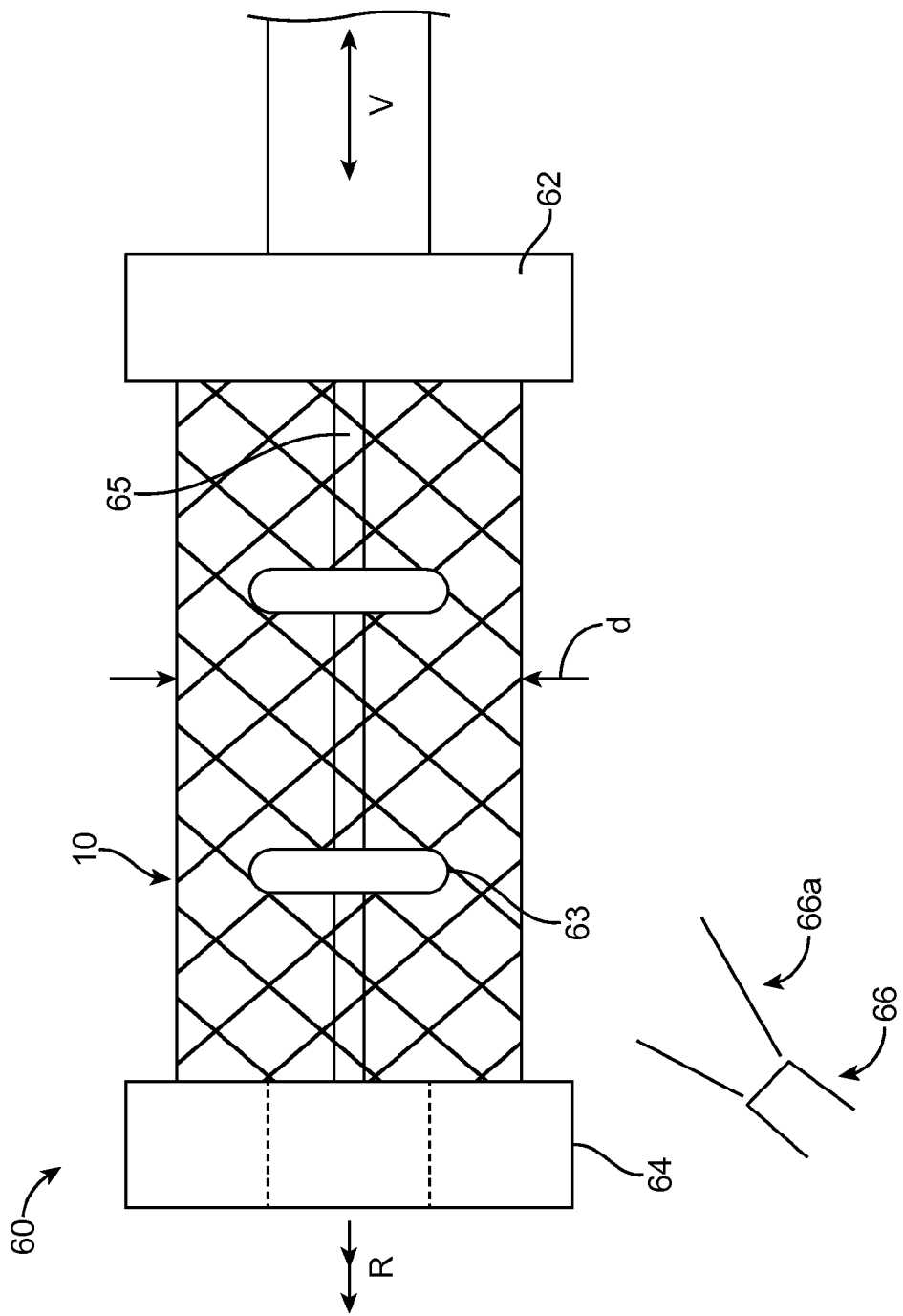
FIG. 12 illustrates a method for applying a coating composition to a braided scaffold.

Referring to FIG. 12 there is schematically shown the braided polymer scaffold 10 on a spraying apparatus 60. A composition 66a is being applied by a sprayer 66. The scaffold is supported upon one, two or more collars 63 intended to minimize contact area between the scaffold and the support. The scaffold is orientated horizontally (gravity acts normal to mandrel 63 axis) but could alternatively be orientated so that mandrel 63 axis is parallel to direction gravity acts. The scaffold is disposed between two blocks, members or collars 62, 64. The apparatus shown is coupled to a rotary that rotates the apparatus and scaffold about the mandrel 63 axis. The member 62 can be moved left to right with a velocity "V." a secondary or coupled drive to the rotary drive may be used to combine or sequence the axial movement at velocity V and rotary rate R. In operation the scaffold rotates by rate R and the member 62 moves towards and away from block 64 at a rate V. The rate V may about 1, 3, 5 or 10 cycles per second. The amount of member 62 displacement towards and away from member 64 may SD' ½ of SD' or ½, ⅕, ⅙, ⅓, or ¼ of the change in axial length of the scaffold between stowed states in the catheter and free standing state.

Collapse and Loading on Catheter

Scaffolds according to disclosed embodiments may be reduced to a collapsed state or delivery configuration using a stent collapser or crimper that imparts a radially inward force on the scaffold which reduces its diameter. An example is a sliding wedge or iris crimper with adjacent pie-piece-shaped sections that move inward and twist, much like the leaves in a camera aperture.

Since the length the scaffold increases as the diameter decreases, the collapsed length, Lc, will be greater than the free-standing length, Lf or Zi. The ratio Lc/Lf may be 1.5 to 2.5, or more narrowly, 1.8 to 2.2, 1.9 to 2.1, 1.9, 2, or 2.1.

Table 1 depicts the changes in scaffold length for two braided scaffolds with different free lengths in vessels of different diameters. Both scaffolds are made from PLLA fibers (0.006"×01017").

TABLE 1

Lengths of two scaffolds deployed in vessels of different diameters.

| Free Length (mm) | Length in 7F Delivery System | Length in 5 mm Vessel | Length in 6 mm Vessel |
|---|---|---|---|
| 25 | 50 | 46 | 42 |
| 50 | 96 | 90 | 84 |

Delivery Device and Scaffold Deployment

A delivery assembly includes the scaffold, an inner tubular member, and an outer tubular member including a restraining sheath. The scaffold in a collapsed state is disposed over the inner member and is within and radially constrained by the sheath. The collapsed OD of the scaffold may be the ID of the sheath. Once the delivery assembly is positioned at an implant site in a vessel, the scaffold may be deployed by pulling on the outer member to move it towards the catheter proximal end while the inner member, e.g., a tube, which includes a stop in abutting contact with a proximal end of the scaffold, is held stationary or pushed towards the catheter distal end (the inner member is disposed within the bore scaffold, while the outer member sheath circumscribes the scaffold).

The inner member may include a proximal stop in abutting contact with the scaffold proximal end. The stop may be pushed towards the catheter distal end (thereby also pushing the scaffold in this direction) as the outer member is moved towards the catheter proximal end (thereby withdrawing the sheath from the scaffold to allow it to radially expand). That is, the outer member is pulled (towards the catheter proximal end) while the inner member (with stop) is pushed (towards the catheter distal end). It has been found beneficial for treatment of different lesion types, e.g., varying degrees of calcification, to provide a device by which the amount of "push" of the inner member distally can be increased or decreased relative to the amount of "pull" of the outer member proximally. No push or less push of the scaffold, or push or more push of the scaffold distally can increase or decrease, respectively, the deployed scaffold length, which varies inversely with the radially unrestrained diameter of the scaffold. As such, by controlling the length of the scaffold when deployed from the scaffold (by the amount of push of the inner member compared to pull of the outer member) the doctor can control the amount of radial force the scaffold will impose on the vessel. This is advantageous as a means for improving patency when encountering hard lesions since a higher radial stiffness may be required to open and support such lesions. Additionally, a push/pull control facilitates more control over placement of the scaffold.

Examples of catheter systems for a desired push-pull capability on deployment, for accurate placement at a target vessel and treatment of lesions, and/or deployment systems addressing the unique challenges in deployment of braided scaffold (as opposed to a braided stent) follow.

Figure 7A:
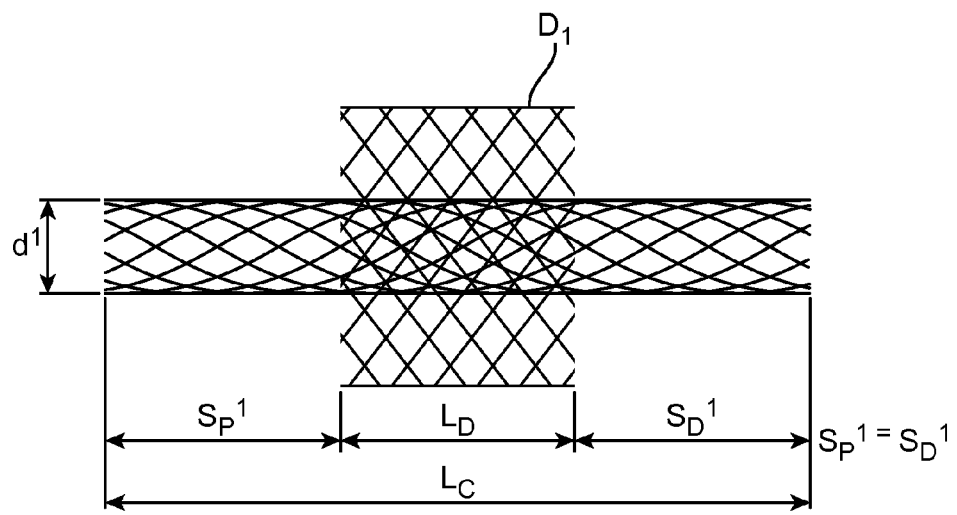
FIGS. 7A and 7B depict expanded and collapsed or compressed states of a braided scaffold according to the embodiments, the expanded states describing a free-standing state, i.e., no axial or radial restraint imposed on the scaffold.
Figure 7B:
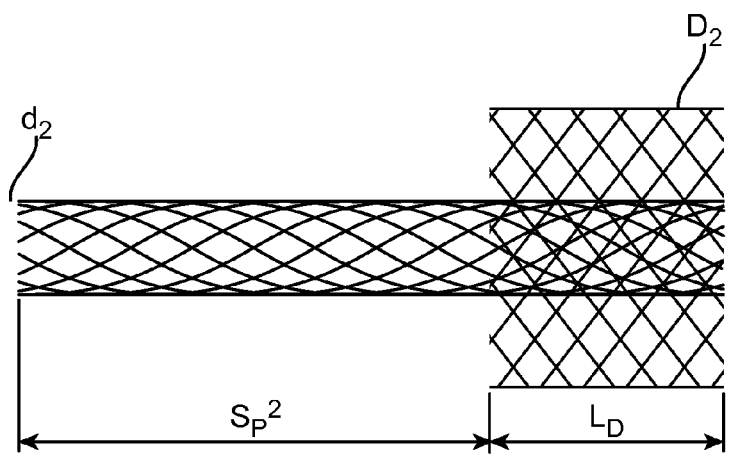

Referring to FIGS. 7A and 7B, there is shown two views of a braided scaffold configured at different diameters. The smaller diameter d', d2 would correspond to the scaffold diameter when constrained radially within an outer member at a catheter distal end. The larger diameter D1, D2 would be the scaffold diameter if removed from the outer member lumen and allowed to expand freely, i.e., without axial or radial constraints. It would be desirable to have the scaffold positioned at the far right (i.e., distal end) when deployed, which is FIG. 7B. However, when the braided scaffold deployment mechanism has only a restraining sheath withdrawn or rolled back to the catheter proximal end, the scaffold will also move significantly axially as its diameter changes unless there is an axial restraint imposed. These different axial positions are a byproduct of axial shortening at proximal and distal ends. The degree of shortening is in proportion to an increase in diameter, as shown. When it possess the diameter D2 or D1, the scaffold may have a certain degree of increased radial stiffness when the ends are not axial restrained, but generally this stiffness is rather small. However, when the ends are axial restrained, either partially or fully by vessel walls the radial stiffness can be quite high. A scaffold deployed within a vessel varies between these two extremes depending upon the amount of axial movement occurring (i.e., slippage) between the scaffold and vessel walls axially and axial compliance of the vessel.

What is needed is a suitable delivery system that predictively controls the distal location of the braid during deployment and/or its radial force imposed on the vessel walls. According to some embodiments this delivery system, now described in detail and as disclosed below, may be configured deploying one or more braided scaffolds on a single catheter. The scaffolds include those embodiments discussed in connection with FIGS. 19-21. Thus, the following discussion also applies to the previously disclosed scaffold segments deployed in narrowed vasculature or having differently sized areas requiring consideration of scaffold size so as to avoid creating a COF condition on the vessel.

Figure 8A:
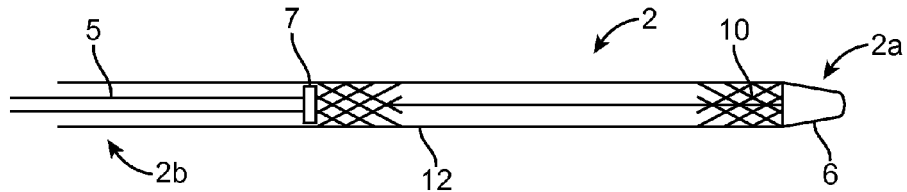
FIGS. 8A-8D describe a first sequence of deployment associated with the scaffold of FIG. 7A.
Figure 8B:
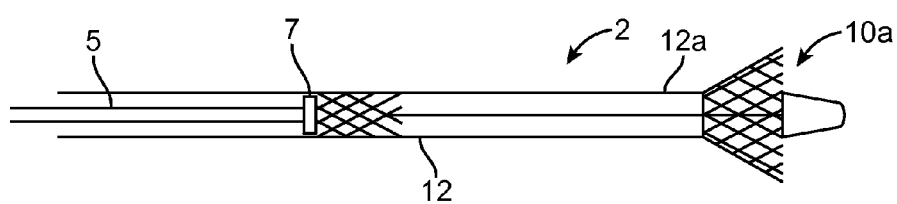
Figure 8C:
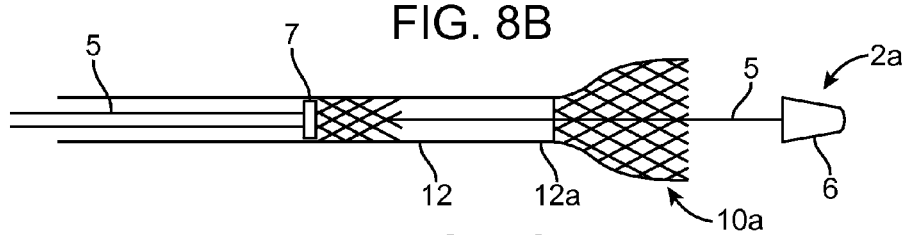
Figure 8D:
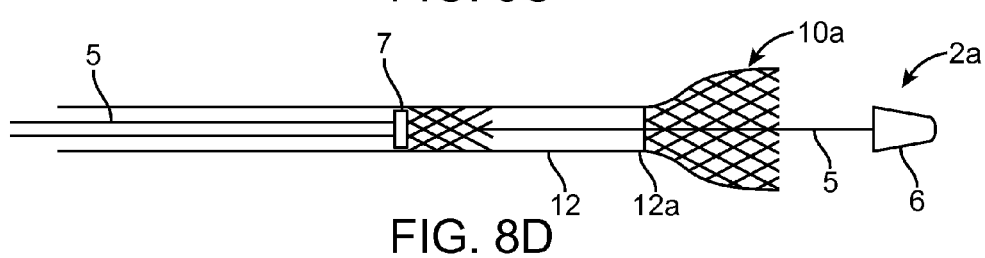

Referring to FIGS. 8A through 8C there is shown a typical sequence of deployment of a braided scaffold 10 from a catheter 2 distal end 2a. The scaffold 10 is stowed within an outer sheath 12, which constrains the scaffold to a diameter $d^1$ (FIG. 7A). A stop 7 is fixed to an inner member 5, which may extend from a catheter proximal end 2a to distal end 2b where member 5 is connected to a conical or tapered tip 6. The member 5 may include an inner lumen for passage of a guide wire (not shown) that exits from an opening of the tip 6. The deployment sequence begins with a retractable sheath of the outer member 12 being withdrawn by pulling, pealing-back or rolling back the member 12 towards the catheter proximal end 2b. As shown when the distal end 12a is withdrawn the scaffold begins to open up to its larger (unrestrained) diameter (FIG. 8B). As member distal end 12a continues to be removed from the scaffold and the scaffold opens radially, the scaffold 10 length will correspondingly start to decrease in about the same proportion as it radially expands. The scaffold distal end 10a moves towards the catheter proximal end 2a as its diameter is allowed to increase starting from the scaffold distal end 10a. The end result is that shown in FIG. 7A—i.e., the scaffold 10 is displaced axially. It would be preferred to have the scaffold axial position remain unchanged during this deployment, or to be able to predictably control the axial movement when separated from a delivery catheter.

If the catheter is moved distally in proportion to the outer member being pulled towards the catheter proximal end 2a, then the axial position of the scaffold 10 as it deploys may be controlled. However, note that the tip 6, which is connected to the inner member 5 also moves distally. This may not be desirable in cases where there is inadequate artery length or diameter to accommodate the advancing tip. Also, it may be difficult to obtain accurate placement by this type of adjustment.

Figure 8E:
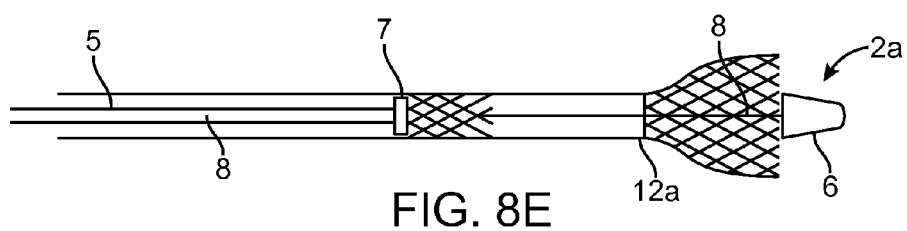
FIGS. 8E-8F describe a second sequence of deployment associated with the scaffold of FIG. 7B. The sequence described may be adapted for use with a single braided scaffold (as shown) or multiple scaffold segments loaded on a catheter.
Figure 8F:
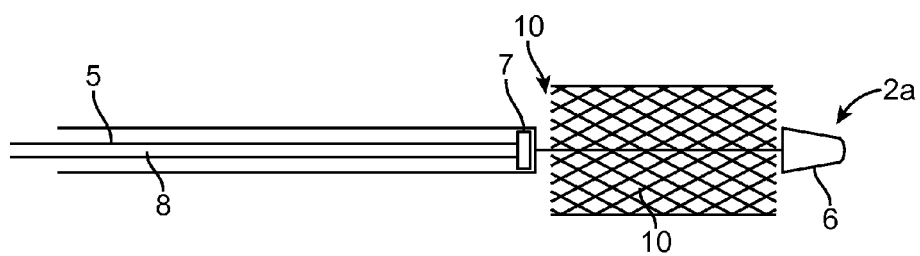

FIG. 8E shows an alternate delivery where the inner member is made of two concentric tubes—an outer tube 5 located proximally of the stop 7 and inner tube 8 located within the scaffold 10 bore. The inner tube 8 is attached to the tip 6 and has a lumen for receiving a tracking guide wire. The stop 7 is attached to the inner member outer tube 5 and lies in abutting contact with the scaffold proximal end 10*b*. For delivery in this case the outer member 12 may be moved proximally, the inner member outer tube 5 is pushed distally, or a combination of movement of 5 and 8 to control the axial location of the scaffold when deployed. Additionally this type of adjustment allows the tip 6 (which may come with a radiopaque marker for guidance) to maintain its position. FIG. 8F shows the deployed braid using the FIG. 8E technique. Note the distal end of the braid 10 and the tip 6 has not moved axially during delivery. The tube 8 moves within the lumen of tube 5. Tube 8 may be held in place at the proximal catheter end 2*b* (thereby holding tip 6 in place) while tube 5 is pushed towards the catheter distal end 2*a*.

Figure 9:
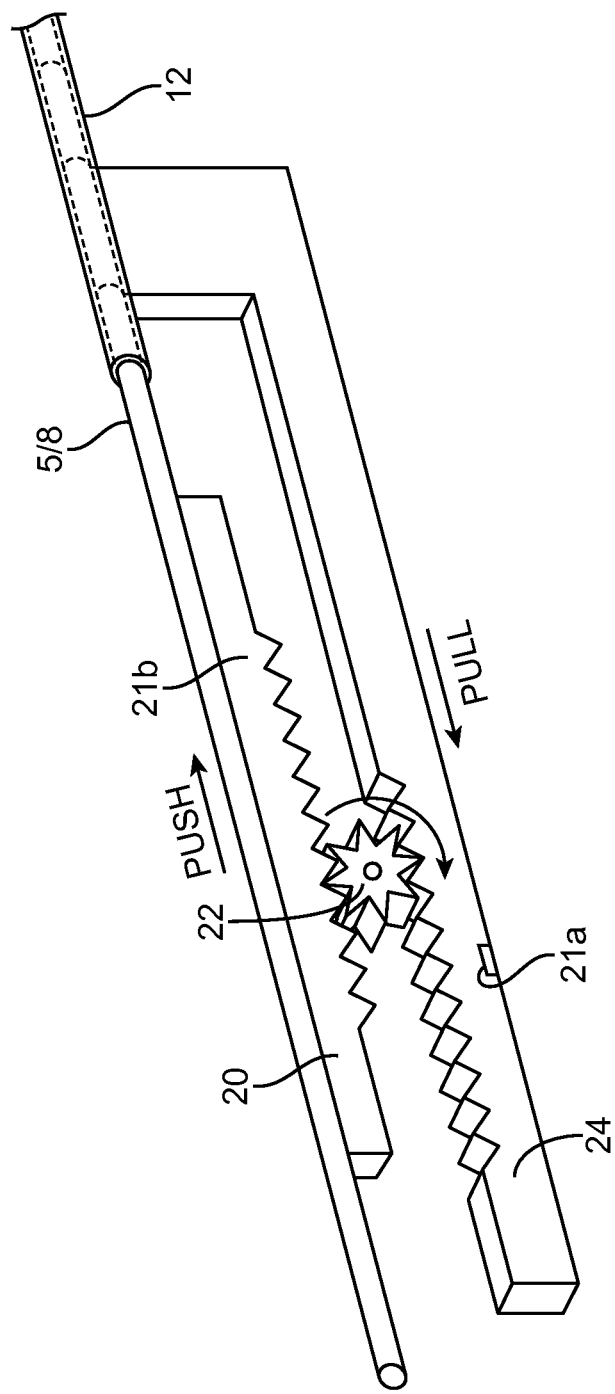
FIG. 9 is a perspective schematic of a proximal end of a catheter showing a mechanism for applying a % 50 pull and %50 push when deploying the scaffold of FIG. 7B. The mechanism may be adapted for deploying a single braided scaffold or multiple scaffold segments loaded on a catheter.

FIG. 9 shows a first embodiment of a mechanism that may be used to advance the stop 7 towards the distal end 2*a* (while the tip 6 is kept stationary) as the outer member 12 is moved towards the proximal end 2*b*. There is a rack at the catheter proximal end, which may be incorporated as a separate handle fitting or integrated into the catheter handle that includes an inflation lumen and/or guide wire lumen. The rack includes an inner member rack 20, connected to the inner member 5, an outer member rack 24, connected to the outer member 12, and a gear 22 intermeshing with threading or teeth formed on the respective racks 20, 24. The teeth produce axial displacement of the upper and lower members, respectively, when the gear is rotated. When the gear is rotated, e.g., clockwise, the outer member 12 is pulled proximally and the inner member 5 and stop 7 are pushed distally. When the gear is rotated counterclockwise the two racks return to their original positions. The gear may include a handle portion or knob, which would allow an operator to turn the gear 22 so as to initiate movement of the outer and inner members. In this example the rack produces equal amounts of push and pull of the members. That is, in this embodiment there is a 50% pull and 50% push or equal amounts of push and pull. By having an equal pull to push the scaffold 10 axial location, after the scaffold 10 is separated from the catheter, can be the distal end 2*a* adjacent tip 6, which may be a preferred location (i.e., the location relative to the stowed scaffold in FIG. 7B).

Alternatively, the amount of push can be different from pull by using different gear diameters intermeshing the teeth on the respective racks 20, 24. These alternatives are illustrated in FIGS. 10A through 10D Referring to the embodiment of FIG. 10A, a knob 23 is used by an operator to displace members 20, 24 linearly and in opposite directions (in other words, push and pull). The knob rotates two gears 22*a*, 22*b* at the same rotation rate. When one of the gears 22*a*, 22*b* has a diameter larger or smaller than the other of gears 22*a*, 22*b* the amount of push can be increased or decreased relative to the pull. For example, if the diameter of the gear 22*a* intermeshing with teeth on the upper rack 20 is larger than the diameter of the gear 24 intermeshing with teeth on the rack 24 then when the knob 23 is turned (thereby rotating both gears 22*a*, 22*b*, which are connected to each other in rotation) the inner member stop 7 will be pushed towards the distal end by a greater distance than the outer member 12 is pulled towards the proximal end 2*a*.

Figure 10A:
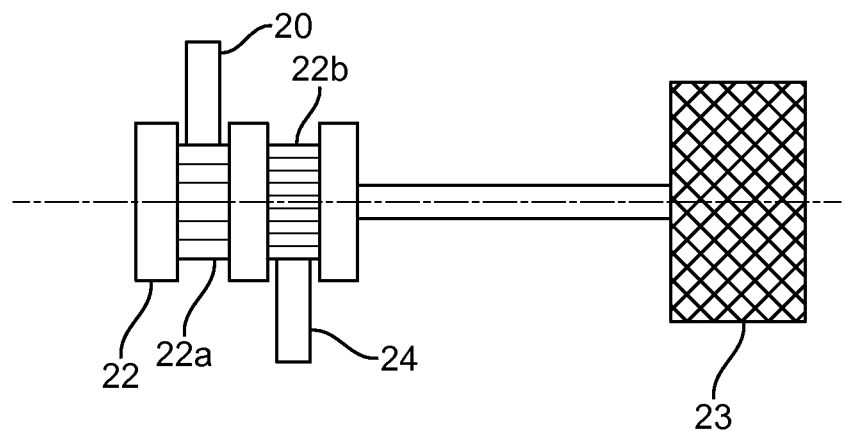
FIGS. 10A-10D are alternative embodiments of mechanisms for applying an equal or unequal push to pull when deploying the scaffold of FIG. 7B. These embodiments showing various combinations of gears coupled to racks. The mechanisms may be used with catheters for deploying a single braided scaffold or multiple scaffold segments loaded on the catheter.
Figure 10B:
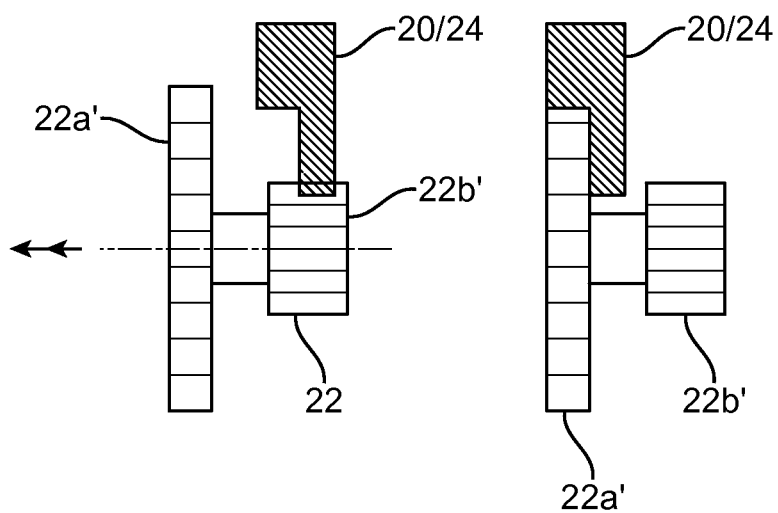

Referring to the embodiment of FIG. 10B, in this embodiment one or both racks may be selectively engaged with two gears 22*a*', 22*b*' of different sizes to increase or decrease, respectively, the amount of push or pull relative to the other rack. For example the rack 20 may be engaged with either gear 22*a*', 22*b*' through a clutch mechanism (not shown) or stepped edges for forcibly displacing the rack towards one or the other gear, whereas the lower rack 24 is engaged with only the lower gear 22*b*'. A rack may also be disengaged with a gear so that there is only a push or pull. This may be necessary where observed movement or a particular condition calls upon more frequent pushing/pulling adjustment to achieve the desired axial placement (or radial force). Thus, both racks may be engaged with their respective gears and the knob turned, then it may be noticed that the scaffold is being held in place by the vessel (no more push, continue with only pull) or there is excessive axial movement (no more pull, continue only with push).

In addition to racks' teeth selectively engaging with gears of different sizes, the one or more gears available for one rack may be rotationally de-coupled from each other. Or the gears engaged with racks may be selectively rotational decoupled by a finger-actuated lock located on the knob 23 or between knobs for separate control of each rack. This will allow separate control of movement of the members 5, 12. This may be desired in order to have greater control when needed in a particular situation, such as fine tuning one of push and pull relative to the other of push and pull; for example, to better control axial position, or to have greater control over the degree of axial restraint or radial expansion (so as to increase radial force on the vessel walls) or manage axial movement better in response to removal of a sheath of the outer member 12. In these cases one can switch to a larger or smaller diameter gear (for changing the push-pull ratio as above), or to temporarily stop a push and continue a pull or visa-versa. In those cases gear(s) intermeshed or associated with the rack 20 movement may be rotationally decoupled from the gear intermeshed or associated with the rack 24. As such, with the gears decoupled rotation of the knob turns only the selected rack while the other rack remains stationary.

Figure 10C:
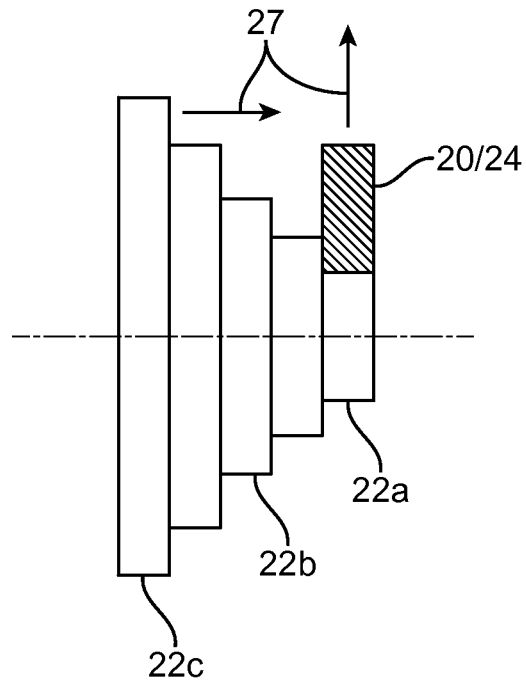

Referring to the embodiment of FIG. 10C, there is a shown an example of a rack 20 or 24 selectively movable between a plurality of gears 22*a*, 22*b*, 22*c* by a clutch mechanism or manually displacing the rack along the rotation axis so that it can engage with different gears (as indicated by 27).

Figure 10D:
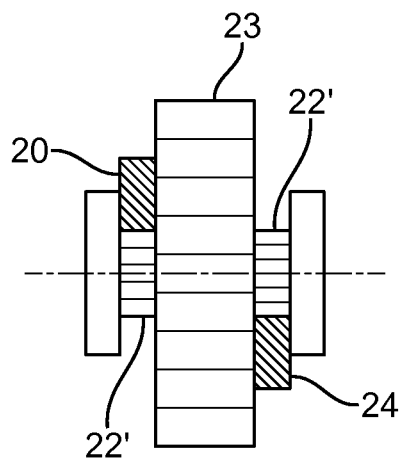

Referring to the embodiment of FIG. 10D, in this embodiment a thumb screw is disposed between a gear 22' for rack 20 and a gear 22' for rack 24 (of larger or smaller diameter than gear 22 for rack 20). The thumb screw 23 is turned to pull and push simultaneously by the gear mechanism. In this example a rotation of the thumb screw 23 displaces the outer member greater than the inner member since the outer member gear is larger.

Figure 11:
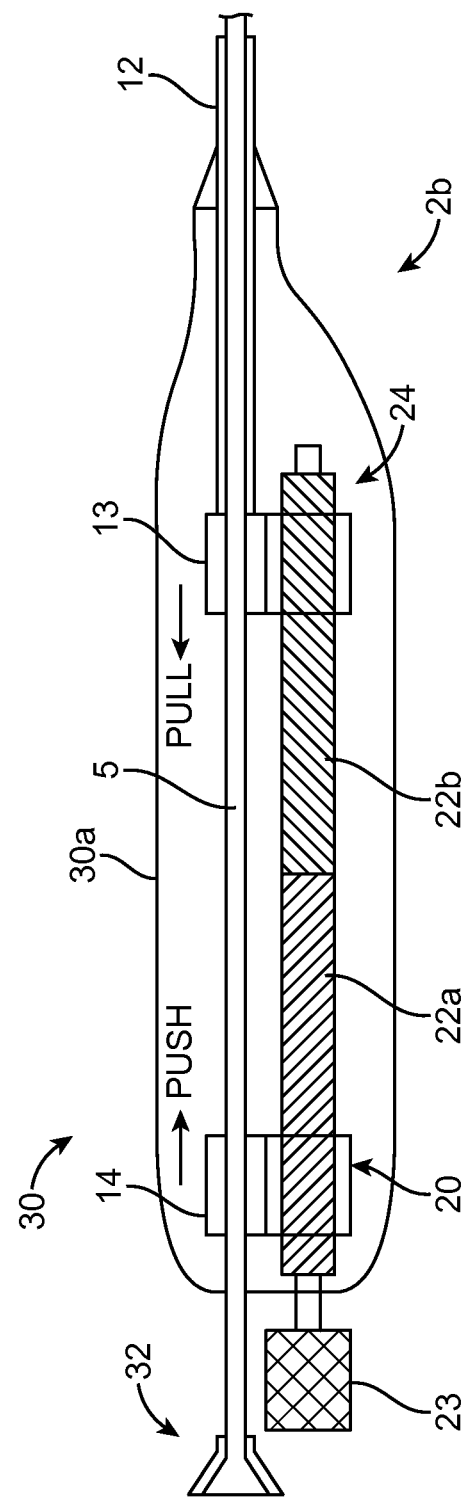
FIG. 11 is a side partial cross-sectional view of a handle portion of a catheter showing an alternative embodiment of a mechanism for deploying the scaffold of FIG. 7B. The mechanism may be adapted for deploying a single braided scaffold or multiple scaffold segments loaded on a catheter.

FIG. 11 illustrates an assembly in the handle portion according to another embodiment of a mechanism for a push and pull. In this embodiment a pair of worm gears 22*a* and 22*b* having a respective left and right handed threading are received within a matching threaded collar portion of member 14 connected to member 5 and threaded collar portion of member 13 connected to member 12, respectively, as shown. The worm gears 22*a*, 22*b* are co-linear with each other and actuated by a knob 23. When the knob 23 is turned the worm gears 22*a*, 22*b* both rotate at the same rate. The collars 5*a*, 12*a* then move toward or away from each other depending on whether the knob is turned clockwise or counterclockwise. For example, when the scaffold 10 is being deployed the knob 23 is turned clockwise, which causes the collar 13 to move towards the knob 23 (thereby causing the member distal end 12*a* to move towards the catheter proximal end 2*b* and a sheath portion to withdraw from the scaffold 10) and the collar 14 to move away from the knob 23 (thereby moving the stop 7 towards the catheter distal end 2a).

Referring once again to FIG. 11 the worm gear system described may be replaced by a turnbuckle. In this embodiment the turnbuckle has a left handed threading on a proximal end, and a right-handed threading on the distal end (or the thread types may be switched). The opposed ends receive respective left and right handed shanks that are coupled to the respective members 13 and 14. When the turnbuckle is rotated the members move towards or away each other, thereby displacing the member 5 distally (push) and member 12 proximally (pull).

In another embodiment the gears described above may be replaced by belts. For example, in FIG. 9 or 10A, rather than use the gears 22 and racks 20, 24, the members 5 and 12 may be coupled to each other by a belt. The belt is wrapped around one or more posts, one of which is connected to a knob that can be operated by the user. When the knob is turned the belt-system operates to simultaneously pull the member 12 towards the proximal end while the member 5 is pushed towards the distal end.

The percentage of push and pull may be 50% each, in which case the same gear sizes can be used. For variable push to pull multiple gear choices for coupling to one or both racks can be used, such as in the examples described above. Moreover, two gears of the same size, but selectively de-coupled to each other can allow for different push-pull protocols. It is understand that 50% push (or pull) means that there is also pull, namely %100−%50=%50 pull. Thus when the scaffold is being deployed by only withdrawing a sheath of member 12 from the scaffold there is %100 pull and no push.

In embodiments it is contemplated that the push % for the member 5 can be about 10%, 20%, 30%, 40%, 50%, 60%, 70%, 80%, 90%, or 20-40%, 40-80%, 30-60%, up to 50%, up to %80% or between about 30% and 70% push. Thus, in these cases the remaining part of the deployment is pull, e g., if 20% push then 80% pull and between about 30% and 70% push means between about 70-30% pull. Moreover, it is understood that the different percentages of push and pull may occur by different gearings engaged by the racks, or it can be incremental pulling while push stays constant or no push, etc.

With respect to having different push to pull, the embodiments include one or more gears associated with a rack, where gear sizes for the rack 13 can be the same size, greater than, or less than the gear size(s) for rack 14, a gear for rack 13 can be 0.5, 0.3, 0.7, 1.5, 2, 2.5, 1.2, 1.3, or 3 times the size of a gear for rack 14.

Loading Scaffold into Device and Deployment

In some embodiments the braided scaffold is radially compressed and inserted into the outer member 12 just prior to the medical procedure, as opposed to having the scaffold placed within the outer member 12 and compressed to a smaller diameter for weeks to months awaiting use. By loading the scaffold just prior to use, creep of the polymer material or a cold set in the collapsed or compressed state is avoided.

Loading the scaffold prior to delivery, according to one embodiment, includes using a funnel tube to load the scaffold within the outer member. A funnel tube provides a doctor with a means for funneling the scaffold down to a compressed diameter so that a doctor may then slip the scaffold within the outer member.

According to some embodiments, the medical professional receives the packaged sterile goods including the catheter 2 contained within a protective tubing or coil (not shown). At the catheter distal end there is the funnel tube 52, which holds the scaffold 10 within. The funnel tube 52 is included with the packaged medical device and holds the scaffold in a free expanded state within its tubular container. The funnel tube 52 has a narrowed proximal tip 52a with opening sized for passing the scaffold in a compressed state into the outer member 12 lumen. The opening 52a is the passage for loading the scaffold 10 onto the catheter in a compressed state. The scaffold 10 may be pulled through the opening 52a using tube 8 when loaded on the catheter 2.

The following steps may be practiced by a medical professional, or instructions included with the medical device kit, for loading the braided scaffold on the catheter. Using the catheter handle mechanism, e.g., one of the decoupled gears embodiments above, begin to move tube 5 towards narrowed tip 52a and over tip end 52a so that tip 52a sits within tube 5 or tube 8, or the medical device may be configured this way when received, i.e., a portion of the tip 52a is already inserted into the tube lumen. Then retract or pull the tube 5 towards the catheter proximal end 2b when the scaffold has been funneled down and inserted through the tip 52a. This brings the scaffold 10 within the outer member 12, thereby loading the scaffold on the catheter. Finally, remove the funnel tube from the distal end. A loading mandrel or insertion tool may be included with the kit to assist with pulling the scaffold 10 through the opening 52a and within the outer tube 12. Additionally, the inner tube should be able to radially expand to a certain degree so that a medical professional can easily insert the scaffold therein without risk of damaging either the catheter or scaffold. In particular, the inner tube would be compliant for this loading process as well as to support the scaffold and prevent buckling, as explained more below. Once the scaffold is at least partially within the tube 5 or 8, the tube with scaffold may be pulled towards the catheter proximal end, thereby loading the scaffold on the catheter.

In other embodiments inner member 8 or 5 may include a balloon. According to this embodiment the balloon is used to assist with expansion of the scaffold when outer member is moved towards the catheter proximal end 2b (e.g., sheath portion of member 12 is pulled, pealed, or retracted back to allow the scaffold to expand into the vessel). The balloon may be used both to help fully deploy the scaffold and assist with anchoring it to the wall of the vessel. A balloon may be necessary when cold-setting or creep has set in for a scaffold compressed for a long period of time before use.

Moreover, unlike a metal braid, there is greater concern over failure or weakened threads, such as at the ends of the scaffold, due to the lower Young's modulus and more brittle behavior. This difference in material of the scaffold (verses a stent) can result in buckling of scaffold threads at ends, such as during a push-pull procedure where the radial force of the scaffold is being increased to treat a narrowed artery having a high degree of calcification, which may require a high degree of radial force to open the lumen and maintain patency.

If one wishes to increase the scaffold radius, radial force or stiffness to treat such a lesion, a relatively significant axial compressive force may be needed to overcome a radial resistance to expansion imposed by the native, calcified vessel walls. The axial compressive force at the ends of the scaffold during deployment would be imposed by, e.g., the stop 7 being pushed distally and the tip 6 being held in place (FIGS. 8E-8F). Indeed in some embodiments it may be desirable to compress the scaffold length to less than Ld (FIG. 7A) to achieve a higher radial force to impose on the narrowed vessel wall.

For the above reasons, it is desirable for the delivery system to include supporting surfaces that will help prevent ends of the scaffold from buckling when the scaffold is being deployed with a constrained axial expansion. This may be done by incorporating an inner member 8 that has an outer diameter surface that is relative close to the inner diameter of the outer member. With this narrowed space for the scaffold the opposed outer surface of the member 8 and inner surface of the member 12 (e.g., inner surface of a restraining sheath) may support the polymer threads to prevent buckling at the ends. For example, the inner tube 5 may be soft or complaint (as discussed in connection with FIG. 11) so that the scaffold 10 may be pressed into the inner tube 8 when contained within the sheath of the outer member 12. Or the inner tube may include a balloon portion that may be partially inflated when the scaffold is being deployed. The balloon pressure can help to support the ends of the threads as the scaffold is subjected to compressive axial forces needed for increased radial force on native vessel, as the case may be. For example the balloon pressure may be inflated as the scaffold is being deployed. The combination of the compliant inner tube 8 or balloon portion of the tube 8 with the scaffold, wherein the material can find its between threads, can give an effective composite beam-like structure during deployment. The composite beam increases the effective axial strength of the polymer threads and reduces chances of buckling at the ends.

Distal Anchor or Cage

As discussed earlier, one challenge to using braided scaffolds is delivery and deployment. Some earlier disclosed embodiments use a push and pull mechanism to achieve the desired placement when the scaffold is deployed at the target vessel. The embodiments disclosed earlier include a mechanism that allowed an operator at the proximal end to control the amount that the scaffold was "pushed" out of a sheath verses the rate or amount that a radially-constraining sheath was also "pulled" back from the scaffold. Too much "push" displaces the scaffold too far distal and away from the desired location in the vessel. Too little "push" causes the scaffold to move proximally when the sheath is pulled away (as explained in connection with FIGS. 7A-7B). Depending on vessel anatomy and lesion types, a simultaneous control of push and pull can be difficult in practice to implement.

It is desirous to simplify a scaffold deployment process. In some embodiments this is achieved by placing on the catheter distal end an expandable anchor or cage distal of the scaffold. The anchor/cage prevents the scaffold, when being removed from the sheath, from displacing to the right in FIGS. 8A-8F (distally or towards the catheter tip 6). As such, the scaffold may be deployed by essentially pushing it against an anchor/cage, or placing a distal end of the scaffold in contact with the anchor/cage as a sheath is withdrawn.

The anchor/cage may be collapsed in the same sheath as the self-expanding scaffold. When the device is placed at the desired location the anchor/cage is deployed at a position immediately distal to a target location in the vessel (e.g., a lesion). The sheath is then deployed with the anchor/cage in place to limit distal movement of the scaffold. In this way the scaffold may be essentially only pushed to remove it from the sheath (without having the scaffold shift distally of the target) because the scaffold is restrained from moving distally by the anchor/cage.

In some embodiments, catheters described earlier in connection with FIGS. 8A-8C include a deployable anchor/cage. For these embodiments the same description as before applies to the same numbered elements in the following description, except as where noted or clearly understood from the context of the description.

Figure 13A:
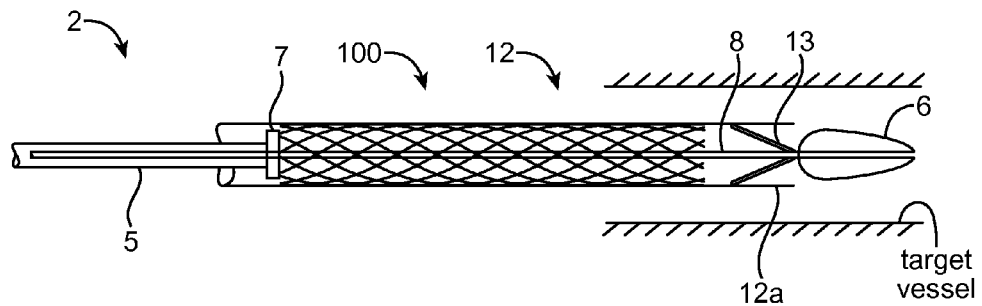
FIGS. 13A-13C show a sequence of deployment and a configuration for a catheter having a distal anchor for preventing or limiting distal movement of a scaffold when the scaffold is released form a sheath. The sequence described may be used for a single braided scaffold (as shown) or multiple scaffold segments loaded on a catheter.

Referring to FIG. 13A therein is described the catheter 2 having the tip 6 and lumen 8 for passage of a guide wire (not shown). The scaffold 100 (or scaffold 10) is mounted near the catheter distal end 2a and radially compressed within a retractable sheath 12. The member 5 with pusher 7 for pushing the scaffold 100 out of the sheath 12 is located proximal of the scaffold 100. The catheter distal end 2a is delivered to the target vessel.

An anchor 13 may be made from a super elastic shaped-memory material such as a Nitinol. The anchor 13 may include one, two, three, four or more arms that are configured to radially extend outward when the sheath 12 is withdrawn. The arms are connected to the external surface of the tube 8, e.g., by welding or adhesive. The ends of the arms may be straight, gently curved or straight having a circular-like end so that the extended arm when contacting the vessel wall does not cause irritation to, or damage the vessel. The arms may be coated with, or contain a radiopaque substance so that its position in the vessel may be readily identified by imaging. For example, the tips of the arms of the anchor 13 may be made of material capable of being detected under X-ray.

Figure 13B:
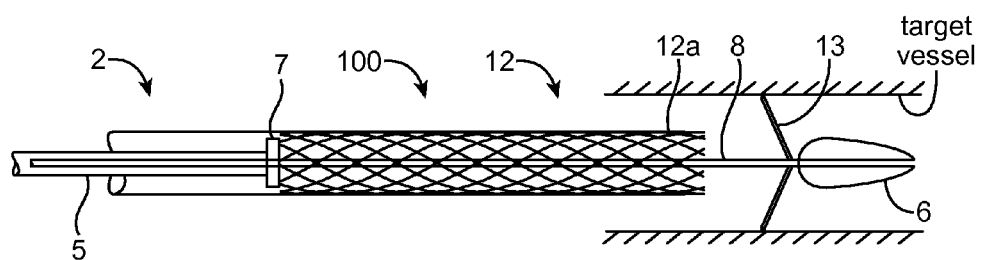

Referring to FIG. 13B, the sheath distal end 12a is withdrawn from the anchor 13, causing the anchor 13 to deploy outwardly and contact walls of the vessel. In this position the anchor 13 will resist distal movement of the scaffold 100 when the sheath 12 is withdrawn.

Figure 13C:
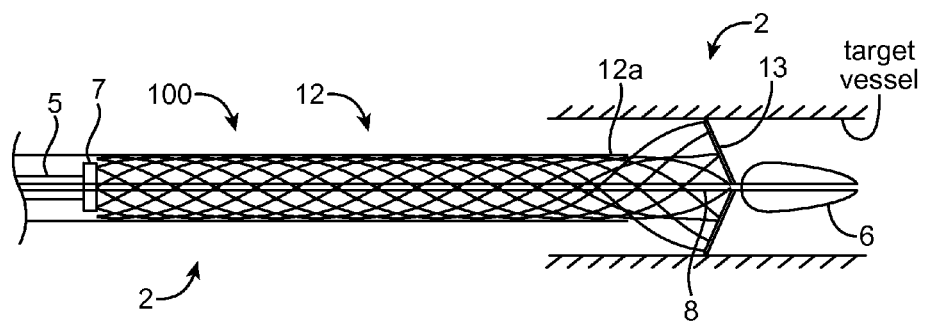

Referring to FIG. 13C, with the anchor 13 deployed the sheath 12 is next withdrawn from the scaffold 100, which action would cause the scaffold 100 to shift to the left in FIG. 13B or proximally if the member 5 were not also used to push the scaffold 100 forward (as discussed earlier). Utilizing the anchor position 13 as the desired most distal location for the scaffold 100, the sheath 12 is rolled or pulled back and the member 5 pushes the stopper 7 into the scaffold 100, out of the sheath 12 and against the anchor 13. After the sheath 100 is fully removed, the scaffold 100 is deployed and located as desired at the target vessel.

Figure 13D:
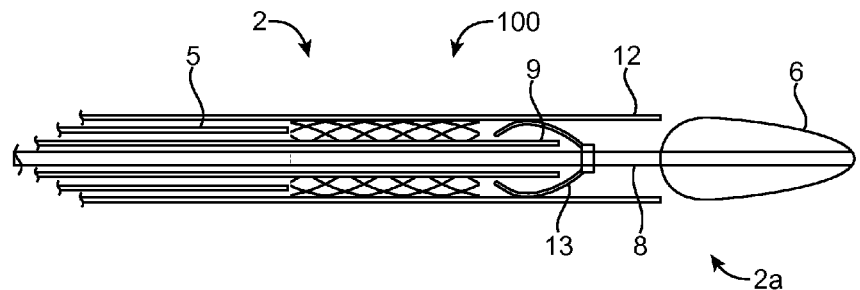
FIG. 13D shows the catheter of FIGS. 13A-13C and with a retrieval mechanism for collapsing and retrieving the anchor. The sequence described may be adapted for use with a single braided scaffold (as shown) or multiple scaffold segments loaded on a catheter.

FIG. 13D shows the catheter 2 with an additional retrieval mechanism. The retrieval mechanism includes a tubular member 9, which is pushed distally and through the lumen of the deployed scaffold 100 after the scaffold 100 has been deployed. The member 9 is used to collapse the anchor 13 after the scaffold 100 is deployed, so that the anchor 13 (contained within the member 9) and tip 6 can be safely pulled to the left in FIG. 13D or proximally through the deployed scaffold 100 lumen without getting caught on the scaffold 100. The catheter 2 may then be fully removed from the body.

Figure 14A:
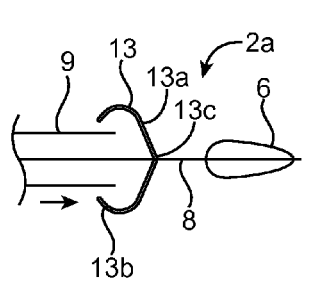
FIGS. 14A-14C shows a distal portion of the catheter of FIG. 13D and sequence for collapsing the anchor using the retrieval mechanism. The sequence described may be adapted for use with a single braided scaffold (as shown) or multiple scaffold segments loaded on a catheter.
Figure 14B:
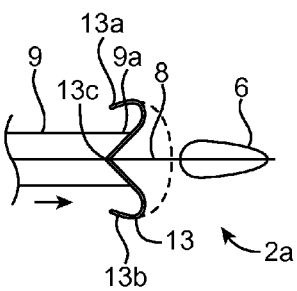
Figure 14C:
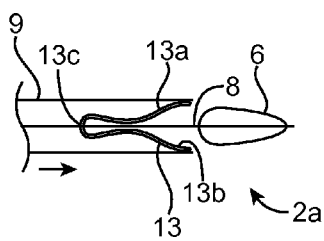

The aforementioned collapsing of the anchor 13 by member 9 is illustrated in FIGS. 14A-14C. The member 9 distal end 9a moves distally (as shown), approaches and makes contact with arms 13a and 13b. The member 9 continues to move distally, thereby causing the anchor 13 to deflect distally (FIG. 14B). Eventually the anchor 13 arms 13a, 13b become fully contained within the distal end 9a. As the anchor 13 is deflected backwards the distal tip 6 may also move proximally in response to the applied forces on the arms 13a, 13b. The two arm 13a, 13b are connected to the tube 8 outer surface at connection 13c. After the anchor 13 is fully collapsed and contained within the lumen of member 9, the distal end 2a including tip 6 and guidewire may be withdrawn proximally through the lumen of the deployed scaffold 100.

The arms 13a, 13b in FIGS. 14A-14C may have an inwardly-angled curvature (as drawn), or the arms may be straight (FIG. 13B). As for the former arm shape, which may cause problems of entanglement with the deployment scaffold 100, in an alternative embodiment a cage, as opposed to an anchor, may be used as a distal stop for scaffold deployment.

A distal balloon (as opposed to deployable arms) may instead be used to halt or resist distal movement of the scaffold 100. The balloon (not shown) may be placed where anchor 13 is located, between the scaffold 100 and tip 6 in FIG. 13D. Before releasing the scaffold 100 from the sheath 12, the balloon, which may or may not also be contained within the sheath 12, is inflated to present an obstacle or barrier preventing the scaffold 100 from displacing distal of the target location. After the scaffold 100 is deployed the balloon is deflated (if necessary a vacuum drawn to reduce down the diameter) and the distal end 2a (as before) withdrawn through the lumen of the deployed scaffold 100.

Figure 15A:
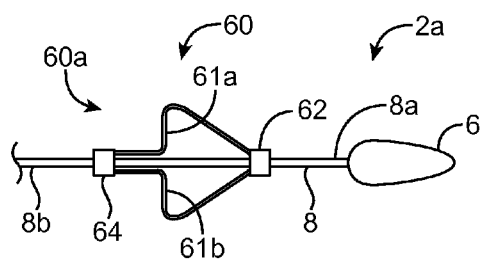
FIGS. 15A-15E show collapsed and deployed configurations of a first disclosure of a distal cage for preventing or limiting distal movement of the scaffold when the scaffold is released from a sheath. The cage has a side view profile resembling an arrow-head. The cage described may be adapted for use with a single braided scaffold (as shown) or multiple scaffold segments loaded on a catheter.
Figure 15B:
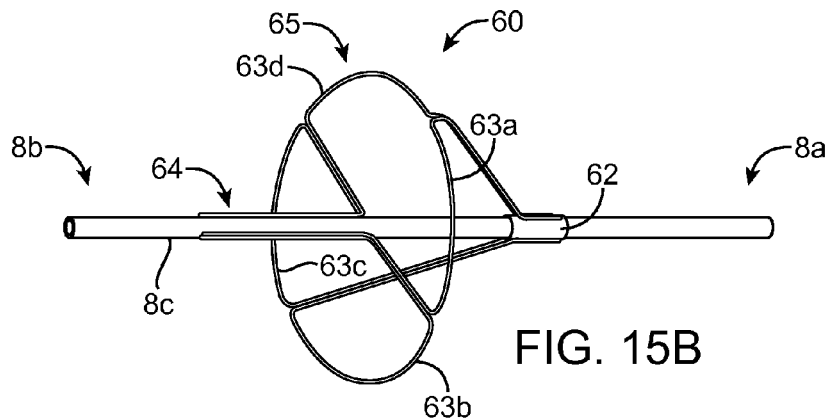
Figure 15C:
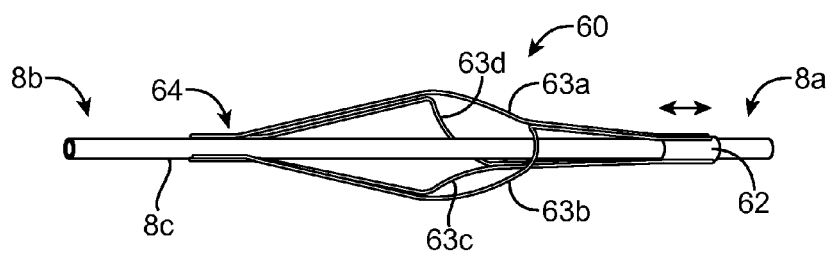

Referring to FIGS. 15A-15C there is shown a collapsible cage 60 alternative to the anchor 13. The locations 8a, 8b in the drawings refer to proximal and distal locations on the tube 8 or a guidewire 8 for the catheter (thus, element 8 is a tube holding a guidewire or the guidewire itself). The cage 60 may be located at the same location as the anchor 13.

A cage 60 when deployed may present a flat frontal or proximally-facing profile 60a and tapered distally-facing profile 60b. Thus, the cage 60 may resemble an arrow-head, as shown in FIG. 15A. Or a cage 70 may resemble more of a rectangle structure, as shown in FIG. 16C. In either case there may be a flat profile 60a configured to come into contact with the scaffold 100 when the scaffold 100 begins to displace distally.

The profiles 60a, 60b are formed by upper and lower portions 61a, 61b of shape-memory wires. Proximal and distal portions of wire portions 61a, 61b may be directly affixed to tube 8 proximal end 8b and a sliding distal collar 62 mounted upon the tube 8 distal end 8a, respectively. Alternatively, both proximal and distal ends of wires may be fixed to sliding collars 62 and 64. These embodiments are shown in FIGS. 16A-16D.

Referring to FIGS. 15A, 15B the cage 60 may be made from four similarly shaped wires 63a, 63b, 63c and 63d arranged to form a circular body 65. Ends of wires 63a-63d are attached directly to the tube at proximal end 8b and sliding collar 62 at the distal end 8a. Collar 62 may freely slid from right to left so that cage 60 can be configured between a deployed configuration (FIG. 15A) and collapsed or stowed configuration (FIG. 15B). The wires 63a and 63d are paired together to form one half of the circular body 65 and the wires 63b and 63c are paired together to form the other half of the circular body 65. The shape-memory of the wire material causes the wires 63 to form the cage 60 shape of FIG. 15A when there is no external force applied to the wire, i.e., when the sheath 12 is not radially constraining the wires 63). A similar wire structure is shown in U.S. Pat. No. 7,037,320, which has the same assignee as the present application.

In the same manner as described earlier in connection with FIGS. 13A-13D a scaffold 100 is deployed from a catheter 2 having the cage 60 by removing the sheath 12 from the cage 60. The scaffold 100 is deployed. Then the cage 60 collapsed and removed using the member 9.

Figure 15D:
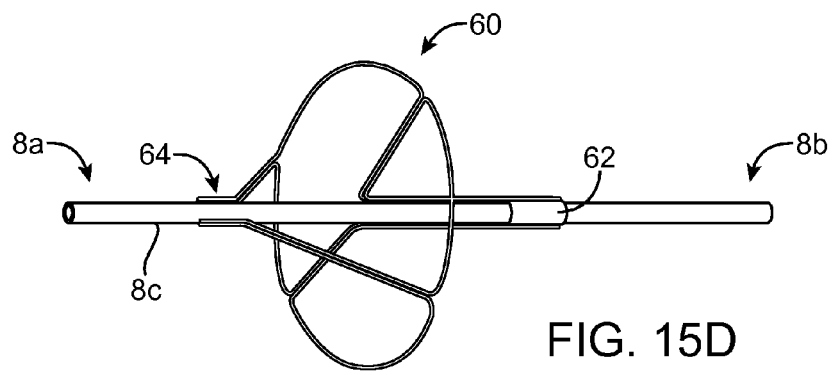
Figure 15E:
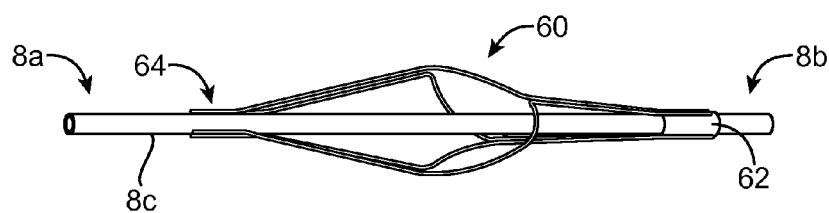

FIGS. 15C-15D show a second embodiment of the cage 60. In this embodiment the cage 60, wires 63a-63d, lumen 8 and operation thereof when implanting the scaffold 100 is the same as described in connection with FIGS. 15A-15C except that the sliding collar 62 is now located on the proximal end 8b as opposed to distal end 8a in FIGS. 15A, 15B.

Figure 16A:
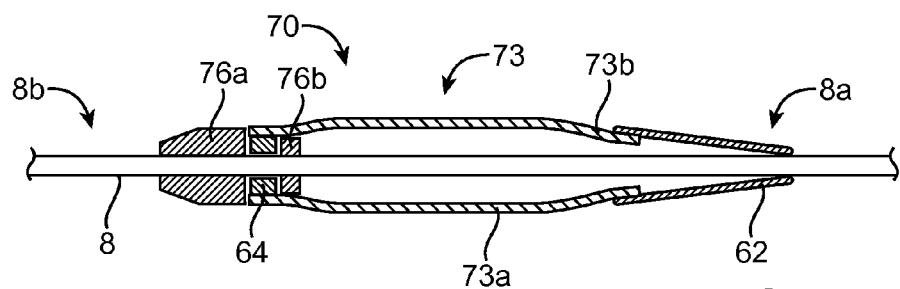
FIGS. 16A-16C show collapsed and deployed configurations of a second disclosure of a distal cage for preventing or limiting distal movement of the scaffold when the scaffold is released from a sheath. The cage has a side view profile resembling an arrow-head. The cage described may be adapted for use with a single braided scaffold (as shown) or multiple scaffold segments loaded on a catheter.
Figure 16B:
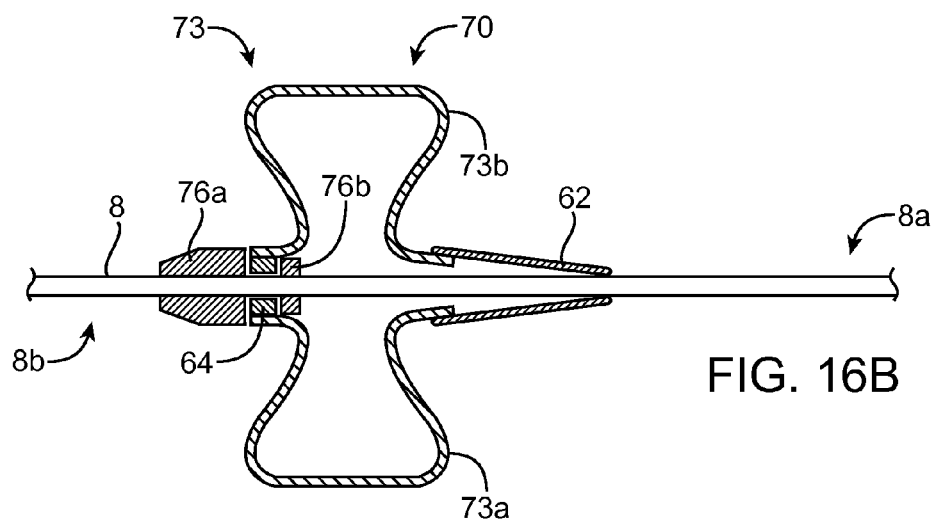
Figure 16C:
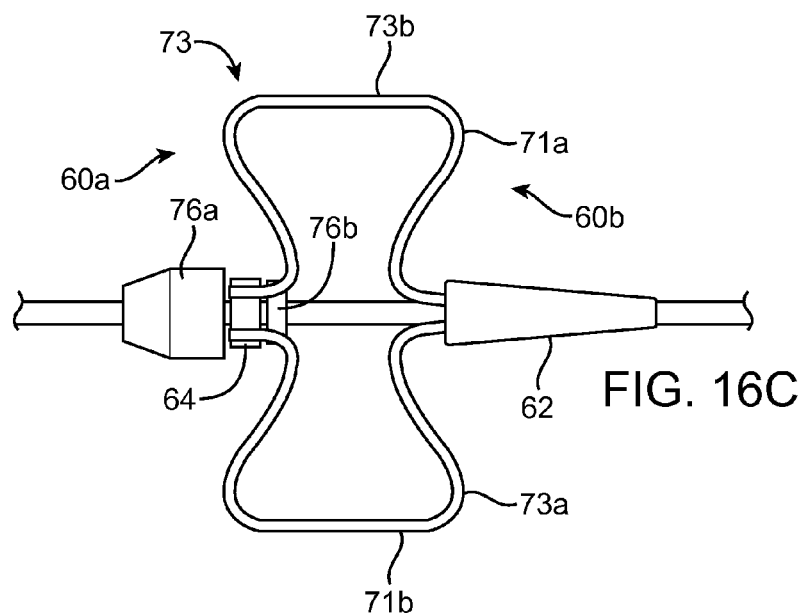
Figure 17:
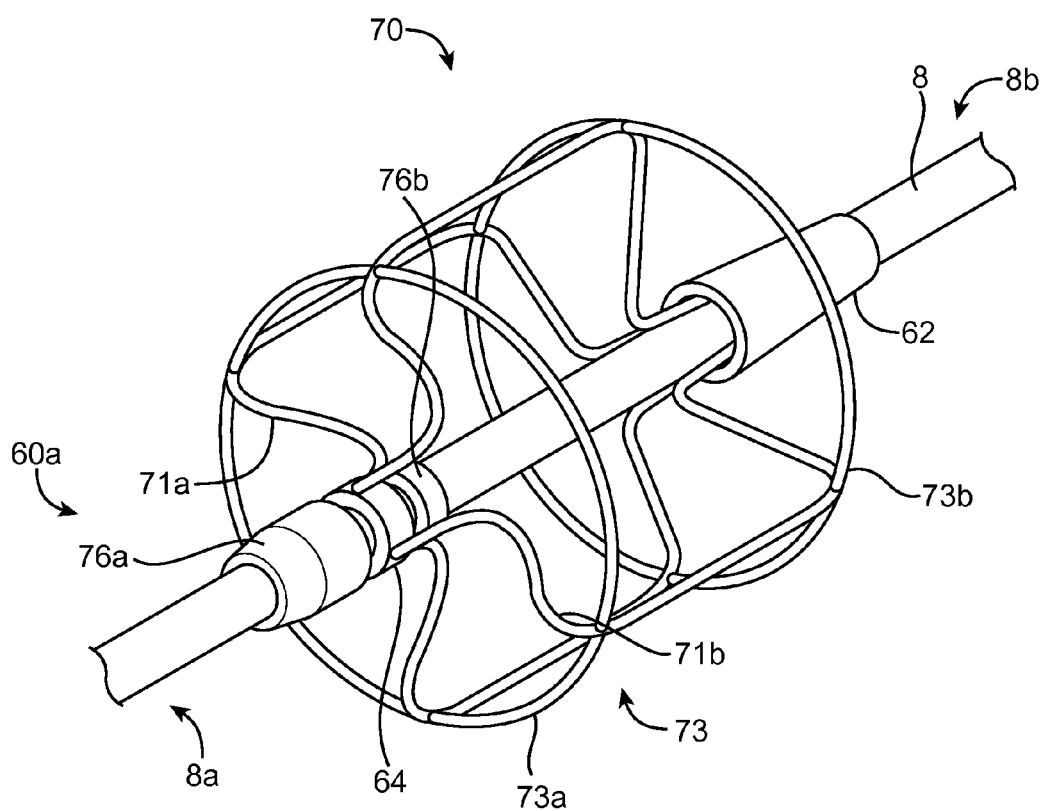
FIG. 17 is a perspective view of an alternative cage for use in the manner described for the anchor and cage of FIGS. 13, 14, and 15 and 16. The cage has a side view profile resembling an arrow-head. The cage described may be adapted for use with a single braided scaffold (as shown) or multiple scaffold segments loaded on a catheter.

Referring to FIGS. 16A-16D there is shown a cage 70 having some of the same characteristics as the cage 60. FIGS. 16A, 16B are cross-sectional views. FIG. 16C is a side view. Memory-wires 73 are used to configure between a collapsed configuration (FIG. 16A) and a deployed configuration (FIG. 16B). One embodiment of a deployed cage 70 forming the side-view of FIGS. 16B-16C is illustrated in FIG. 17. Other arrangements are contemplated. The expanded structure of cage 70 takes a different shape from the arrow-head in FIG. 15A yet may have a flat frontal profile 60a opposing distal scaffold movement.

Unlike the cage 60 which has only one end of the wires 63 connected to a sliding collar 62, both distal and proximal ends of wires 73 are connected to sliding collars 62, 64 in FIGS. 16A-16C. It is preferred to have both ends of wires 73 unconnected in axial rotation to the tube 8, i.e., both may freely rotate about the longitudinal axis of the tube 8. The cage 70 is coupled to the tube (or guidewire) 8 in this way so that the deployed cage 70 will not impose any torque upon the tube longitudinal axis when deployed. For example, if upon deployment the anatomy causes the cage to rotate about the longitudinal axis, this can impose a twisting of other components of the catheter 2 or otherwise make it difficult to make adjustments in position or orientation about the longitudinal axis given the torque on the tube 8. Similarly, if it is necessary or desired to rotate the guidewire or tube 8 about the longitudinal axis, then any resistance to this rotation, e.g., the portions 71a, 71b of wires 73 engaged with vessel walls resisting rotation will make these adjustments difficult to perform.

While allowing free-rotation about the tube 8, it is also necessary to restrict or limit longitudinal movement of the case 60 relative to the tube 8 otherwise the cage 60 would not be able to resist distal movement of the scaffold 100. This may be done (without inhibiting rotation about tube 8) by placing stops or barriers 76a, 76b on both sides of one of the collars 64. In this way both collars 62, 64 may freely rotate about the tube 8 but only one may also translate. Translation along the longitudinal axis of tube 8 for one of the collars, i.e., collar 62 in the drawings, allows the cage 70 to move between collapsed and deployed states when the sheath 12 is withdrawn (deploy) or member 9 moved over the cage 70 (collapse). The distal cage 62 may be tapered. The stops 76a, 76b may be welded to the tube 8 outer surface of guidewire 8.

FIG. 17 shows a front profile 60a formed by wires 73 connected to form a forward circular body 73a and a rearward circular body 73b.

Medical Procedure

A medical procedure using one or more of the embodiments of a delivery system and braided scaffold may proceed as follows. In some embodiments a doctor may be guided in part to deploy a scaffold based on a target supporting force or pressure on the vessel. In preferred embodiments the doctor seeks to achieve a target diameter for the deployed scaffold, i.e., the doctor wants to deploy to a diameter 2R (EQ. 1)

A. Doctor determines artery length and diameter at and near the lesion

B. Doctor determines lesion hardness and expected radial force needed to hold the lesion open. This could be done by pre-dilating the lesion with high balloon pressure and then reducing the balloon pressure until the lesion starts to reduce lumen diameter. The radial force needed is above that provided by the reduced pressure balloon. Calcifications will require more balloon pressure to hold open the lumen. Alternatively and preferably the doctor chooses the appropriate deployed diameter based on patient images or pre-dilation using a balloon.

C. From the above information and a pre-calculated chart, as described below, a selection of the required braided scaffold diameter and % push-pull ratio can be made.

D. The delivery system can then be set to the correct push-pull ratio and the intervention preformed.

With respect to Step C, the chart can have listed, as column one, the force or range of forces, or balloon pressure or equivalent balloon pressure (in mm Hg) required to hold open the lumen, or the target/recommended deployed diameter for the scaffold based on the lumen size. This may be the initial reference point for the doctor to choose the appropriate push-pull and scaffold type (or only the push-pull may be needed when the scaffold is pre-selected) to achieve the desired radial force or stiffness to hold the lumen open. Alternatively, or as an additional reference point on the chart (or table), reference may be made to the radial force imposed by the scaffold as a function of scaffold diameter for a given lumen size, e.g., for a 8 mm free-standing scaffold placed within a 5 mm lumen the radial force is 0.5 N/mm (when multiplied by scaffold length Ld gives force or divide by circumference gives approximate radial pressure to compare to balloon pressure). From the force or pressure values the doctor then finds the push-pull ratio to use.

Thus, for a significantly narrowed lesion compared to normal vessel size (e.g., a lesion narrowed to 3 mm for a normal 6 mm lumen diameter) the doctor would, after estimating the force required to hold open the lumen using balloon pressure, find the diameter scaffold corresponding to vessel diameter, e.g., 8-10 mm free-standing diameter for a 5 mm vessel, to use that will also give, as per the chart data for the scaffold, the required length and axial force (at deployment) needed to hold open the lumen at the lesion by setting a deployed length.

The chart(s), which may be included with other indications for use, may include the following information. For each scaffold, differentiated by the free-standing diameter and/or lengths, or deployed diameter and length, the chart gives:

I. Force or pressure (in mm Hg) applied on vessel as a function of vessel lumen diameter, and/or force/stiffness of scaffold and diameter as a function of deployed length and may also give the equivalent balloon pressure, and II. push-pull ratios to achieve I. Force may predominate over length for a small lesion or length may be equally important for a long lesion. The chart may indicate different combinations of the length and force applied with appropriate % push-pull ratio for a given scaffold having a free-standing radius/diameter X and length Y.

III. More preferably the push-pull ratio is given to achieve a target diameter. When there are segments on the catheter the push-pull ratio may be adjusted for each deployed segment based on the target diameter for each segment (e.g., referring to FIG. 21 a different push-pull ratio may be desired for deploying each of scaffolds 201, 202 and 203 to the target deployed diameters).

Scaffold properties such as radial strength, radial stiffness, and crush resistance of the braided scaffold depend on and can be modified by fiber properties and the braid properties to obtain desired scaffold properties. Fiber properties include fiber geometry, mechanical properties, and cross-sectional size. Fiber geometry can be varied from circular cross-section to asymmetric cross-sections and the degree of asymmetry (width: thickness ratio) to change the scaffold properties. The radial strength, radial stiffness, and crush resistance can be increased by increasing the cross-sectional dimensions of the filament, i.e., diameter, width and thickness). Modifying the pattern type, such as diamond of herringbone will change the scaffold properties. These embodiments apply equally to the embodiments discussed in connection with FIGS. 19-21.

The radial strength, radial stiffness, and crush resistance increase as the density of the pattern increases as quantified by the ppi and the number of wrappings. However, the ppi can be high enough that that the scaffold cannot be collapsed to a desired collapsed delivery diameter. Therefore, to maximize the radial strength, a ppi of the scaffold can be selected which is the maximum ppi or ppi range that allows the scaffold to be crimped to a desired collapsed diameter. This maximum ppi or ppi range will depend on other properties of the scaffold such as fiber properties and type of braid. For a scaffold having filaments (0.006"×0.017") with a HB or diamond pattern, the preferred range is 16 to 20 ppi.

Additionally, radial strength, radial stiffness, and crush resistance vary with the axial extension or compression from the scaffold length in the free state. The scaffold can be deployed with a length between the collapsed length and the minimum length of the scaffold.

A bench measured or clinical (or pre-clinical) radial strength, radial stiffness, or crush resistance at a given scaffold length depends of the degree of resistance to axial length change in response to an external force. When a braided scaffold is subjected to an inward radial force or pinching force that deforms the scaffold, the scaffold response is an axial force directed axially towards its ends. The minimum radial strength, radial stiffness, or crush resistance will be obtained when the ends of the scaffold are unrestrained and the scaffold is free to lengthen without restraint. The maximum radial strength, radial stiffness, or crush resistance will be obtained when the ends of the scaffold are 100% restrained and no increase in scaffold length is allowed.

The radial strength of the braided scaffolds when axially unrestrained may be 0.05 to 02 N/mm, 0.1 to 0.4 N/mm, 0.1 to 0.3 N/mm, or 0.1 to 0.2 N/mm. The radial strength of the braided scaffolds when 100% axially restrained may be 0.7 to 2 N/mm, 1 to 2 N/mm, 1 to 1.5 N/mm, or 1.2 to 1.5 N/mm. The radial strength of the braided scaffolds when 50% axially restrained may be 0.3 to 1.5 N/mm, 0.3 to 1 N/mm, 0.4 to 0.8 N/mm, or 0.5 to 0.8 N/mm.

When a scaffold is deployed in a bench setting within a tube or in a pre-clinical or clinical setting in a blood vessel the restraint on the ends will be between the two extremes of unrestrained and 100% restrained. A deployed scaffold in a vessel uses the vessel's axial stiffness to resist braid lengthening and this significantly enhances radial strength. For bench testing, a tube that is placed in the tester jaws of a radial force tester (e.g., MSI Corporation) a tube that resists a scaffold axial lengthening can give an approximation to the clinical radial strength of a deployed braid.

As noted earlier the radial stiffness of a deployed scaffold will be between the stiffness amount when the scaffold is prevented from lengthening and the stiffness value when the scaffold is axially unrestrained. One may adopt the average between these two extremes as an effective radial stiffness; hence a value to use in determining the magnitude of a COF. Thus, when a scaffold is radially compressed, the COF on the vessel may be based on about 50% of the radial force that the scaffold would impose on the vessel if the scaffold was completely prevented from lengthening in response to the radial compression.

The crush recovery of the braided scaffolds disclosed herein may be greater than 95% or 99% or 100% of a deployed diameter after being crushed by a pinching load 50% or 80% from a deployed diameter and is similar to Nitinol self-expanding stents such as the S.M.A.R.T. or ABSOLUTE™ stents.

TABLE 2 braided bioresorbable scaffolds made and evaluated.
Summary of braided scaffold dimensions made and evaluated

| Material | Design | # of picks/ inch | Drug coat | Tungsten | Ribbon cross sections |
|---|---|---|---|---|---|
| PLLA38 | HB | 16 | Zotarolimus | YES | 0.017" × 0.006" |
| PLLA38 | HB | 29-30 | No | NO | 0.017" × 0.006" |
| PLLA38 | HB | 25 | NO | NO | 0.017" × 0.006" |
| PLLA38 | HB | 20 | NO | NO | 0.017" × 0.006" |
| PLLA38 | HB | 16 | NO | YES single | 0.017" × 0.006" |
| PLLA38 | HB | 16 | NO | YES double | 0.017" × 0.006" |
| PLLA38 | HB | 14 | NO | NO | 0.017" × 0.006" |
| PLLA38 | Di | 30 | NO | NO | 0.017" × 0.006" |
| PLLA38 | Di | 25 | NO | NO | 0.017" × 0.006" |
| PLLA38 | Di | 20 | NO | NO | 0.017" × 0.006" |
| PLLA38 | Di | 18 | NO | NO | 0.017" × 0.006" |
| PLLA38 | HB | 16 | NO | NO | 0.020" × 0.006" |
| PLLA38 | HB | 16 | NO | NO | 0.025" × 0.006" |

HB: Herringbone
Di: Diamond

Everolimus impregnated braided bioresorbable scaffold: a manufacturing process for an Everolimus impregnated braided bioresorbable scaffold may use a cold solution extrusion manufacturing process to preserve integrity of the drug. The finished fiber had approximately 20% of the tensile strength of PLLA extruded and hot drawn fiber. The polymer used was PLLA/PCL copolymer (95 mol %/5 mol %). The intrinsic viscosity (IV) of 3.89 dl/g of the polymer is similar to PLLA. The polymer resin is mixed with 2% Everolimus in chloroform (15% polymer everolimus/chloroform) and agitated for about 2 days. The theoretical amount of drug in the polymer is 10.2% if chloroform is completely dried off. Approximately 3.5% of chloroform remained. The fibers were extruded at 45° C. and braided. The braided scaffolds were vacuum dried for 3 days at 40 deg C.

Table 3 shows the total content of everolimus in drug impregnated braided scaffolds.

TABLE 3

| Scaffold ID | Weight of Scaffold (mg) | Amount Everolimus Determined (μg) | As a % of Scaffold Weight |
|---|---|---|---|
| Scaffold # 1 | 85.08 | 5384 | 6.3 |
| Scaffold # 2 | 82.88 | 5117 | 6.2 |
| Scaffold # 3 | 87.03 | 5292 | 6.1 |
| Scaffold # 4 | 82.49 | 5634 | 6.8 |
| Scaffold # 5 | 82.14 | 5449 | 6.6 |
| Average | 83.92 | 5375 | 6.4 |

Dexamethasone Impregnated Braided Bioresorbable Scaffold

Pelletize Dexamethasone procedure: a mixture of 5% dexamethasone (AK scientific) and PL38 (Purac) is pelletized in a single 1" screw extruder at 440-460 deg F. to 3-4 mm pellets. The pellets were dried at 50 deg C. in a vacuum oven overnight. The PLLA/dexamethasone pellets were extruded into PLLA/dexamethasone ribbons in a ¾" single screw extruder at temperature of 430-465 deg F. (zone 1 die temperature) to the size of 0.0017"×0.034". The fibers were collected on a large spool and kept in a freezer for the next step. The extruded fibers are thawed to room temperature and subjected to starching on a draw wind machine. The ratio of the godet1/godet2 was 1:3 and the hot zone temperature was 125 deg C. The drawn fiber after this process had a size of 0.006"×0.017". The fibers then were spooled on a large spool and were transferred on 16 bobbins (200 ft on each bobbin) for braiding. Next, the bobbins were mounted on a Steeger K 80/16 braiding equipment and the fibers were braided on a PTFE mandrel (OD 8 mm) and 48" length with herringbone design. The number of crossed fibers was 15-16 ppi.

Flair Ends and Heat Stabilize

A section of braid is cut on the Teflon mandrel and heat set at 120 deg C. for 8 minutes. HDPE plastic tapered sleeves are placed over the Teflon mandrel on either end of the braid and worked into the braid so that the ends of the braid are flared. Zip ties, annealed wire, or elastic film can be used to hold the braid tightly against the tapered sleeves. The assembly is then placed in an oven and heat set at 120 deg C. for 10 minutes. The ends of the braid are trimmed to length.

Fit Radiopaque Markers

Gold or Platinum/Iridium ribbon of dimensions 0.003"× 0.0025" are folded around fibers as shown in FIG. 4. Two markers are placed on each end of the braid and are 1 mm from the end of the fiber. Friction holds the marker in place. Drug coating may add adhesion for retention.

Collapse and Load into Catheter—The braid is placed into the jaws of a Nitinol stent collapser which reduces its diameter to that of the distal sheath into which it will be placed. The collapsed braid is then pushed into the distal sheath of the delivery system.

The finished fiber had approximately 80% of the tensile strength of extruded and hot drawn PLLA fibers without drug impregnation.

Dexamethasone+PLLA Esterification Reactions—in consideration of the chemical structure of dexamethasone, the lactide undergoes a catalytic and thermolytic ring-opening polymerization to PLLA polymer chain. The lack of free dexamethasone acetate in the scaffold sample is attributed to the trans-esterification reaction between dexamethasone acetate or dexamethasone that is generated during the extrusion process and polymer chains at high temperature used in the pelletizing and extrusion processes.

It has been hypothesized that the backbone of polymer chains is reacted with hydroxyl groups of dexamethasone or dexamethasone acetate during the hot melt directly or due to some small amount of moisture or monomer that exists in the polymer. Dexamethasone acetate first is hydrolyzed to dexamethasone and then dexamethasone is reacted with the polymer backbone. To confirm this hypothesis, a solution of dexamethasone impregnated scaffold in methylene chloride was reacted with 0.1N NaOH overnight. Reacting with NaOH causes hydrolysis of ester bonds created between dexamethasone and PLLA polymer chains. An aliquot of this solution was tested by HPLC.

Zotarolimus coated braided bioresorbable scaffold: the process for making also applies to Everolimus, dexamethasone, or other drugs. The scaffold fibers are made from PLLA and the drug coating is a 1:1 drug to PDLLA polymer ratio which can be varied. PLLA ribbons are extruded from in a ¾" one screw extruder at temperature of 430-465 deg F. (zone 1 die temperature) to the size of 0.0017"×0.034". The fibers are collected on a large spool and kept in a freezer for the next step. The extruded fibers are thawed to room temperature and subjected to starching on a draw wind machine. The ratio of the godet1/godet2 was 1:3 and the hot zone temperature was 125 deg C. The drawn fiber after this process had a size of 0.006"×0.017". The fibers then were spooled on a large spool and were transferred on 16 bobbins (200 ft on each bobbin) for braiding. The bobbins are mounted on Steeger K 80/16 braiding equipment and the fibers are braided on a PTFE mandrel (OD 8 mm) and 48" length with herringbone design. The number of crossed fibers was 15 to 16 ppi.

Flared Ends and Heat Stabilized scaffold: a section of braid is cut on a Teflon mandrel and heat set at 120 deg C. for 8 minutes. HDPE plastic tapered sleeves are placed over the Teflon mandrel on either end of the braid and worked into the braid so that the ends of the braid are flared. Zip ties, annealed wire, or elastic film can be used to hold the braid tightly against the tapered sleeves. The assembly is then placed in an oven and heat set at 120 deg C. for 10 minutes. The fibers at the ends of the scaffold are trimmed to length.

Fit Radiopaque Markers: Gold or Platinum/Iridium ribbon of dimensions 0.003"×0.0025" are folded around fibers as shown in FIG. 4. Two markers are placed on each end of the braid and are 1 mm from the end of the fiber. Friction holds the marker in place and drug coating adds adhesion for retention.

Zotarolimus+PDLLA Coating: A zotarolimus+PDLLA+acetone mixture in the ratio of 1:1:48 by weight is applied to the braid. The scaffold is placed over a mandrel and the mixture is applied with a spraying machine. The drug loading of the coated scaffold is 100 μg/cm².

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A self-expanding stent for treating a peripheral vessel, comprising:
   a segmented braided scaffold including a plurality of braided scaffold segments configured to be deployed end to end in a vessel, and
   at least three of the braided scaffold segments are hybrid segments, each of which comprising non-degradable filaments and degradable filaments woven to form a tubular configuration,
   wherein upon deployment of the scaffold from a collapsed state to a deployed state in a body cavity, the degradable filaments degrade and a radial strength or stiffness of the hybrid segments decreases with time,
   wherein when the degradable filaments are completely degraded, each hybrid segment comprises a residual stiffness provided by the non-degradable filaments, and
   wherein a hybrid proximal end segment a hybrid distal end segment of the scaffold have a higher radial strength or stiffness at deployment than a middle hybrid segment thereof, while having the same residual radial strength or stiffness as the middle hybrid segment, and
   wherein a first degradable polymer filament of the proximal and distal hybrid end segments has a higher degradation rate than a second degradable polymer filament of the middle hybrid segment so that a rate of decrease to the residual strength or stiffness is faster for the proximal and distal hybrid end segments than the middle hybrid segment.

2. The stent of claim 1, wherein the non-degradable filaments are nitinol.

3. The stent of claim 1, wherein the degradable filaments comprise a polymer selected from the group consisting of poly(L-lactide), poly(L-lactide-co-glycolide), poly(DL-lactide), and polyglycolide.

4. The stent of claim 1, wherein the degradable filaments comprise a bioabsorbable polymer.

5. The stent of claim 1, wherein the radial strength or stiffness of at least one of the hybrid end segments decreases by no greater than 60% during the first 3 months after deployment.

6. The stent of claim 1, wherein the radial strength or stiffness of at least one of the proximal and distal hybrid end segments decreases by at least about 50% during the first 3 months after deployment.

7. The stent of claim 1, wherein the stiffness of at least one of the proximal and distal hybrid end segments decreases to 40 to 60% of a stiffness at deployment during the first 3 months after deployment.

8. The stent of claim 1, wherein the stiffness of at least one of the proximal and distal hybrid end segments decreases to a residual stiffness that is less by 40% to 60% of a deployed stiffness, by at least 3 months after deployment.

9. The stent of claim 1, wherein a combined length of the distal and proximal hybrid end segments are 10% to 30% of a total length of the scaffold.

10. The stent of claim 1, wherein one of the hybrid proximal end segment and hybrid distal end segment comprises a metal filament having a cross sectional area (Am), and a degradable filament having a cross-sectional area (Ap), wherein the ratio Ap/Am is 2 to 4.

11. The stent of claim 1, wherein one of the hybrid proximal end segment and hybrid distal end segment comprises a number of metal filaments (Nm) and a number of polymer filaments (Np), wherein the ratio Np/Nm is 2 to 10.

* * * * *